(12) United States Patent
Debreczeny et al.

(10) Patent No.: US 9,752,974 B2
(45) Date of Patent: Sep. 5, 2017

(54) PARTICLE SENSOR WITH INTERFERENT DISCRIMINATION

(71) Applicant: BugLab LLC, Concord, CA (US)

(72) Inventors: Martin P. Debreczeny, Berkeley, CA (US); Joseph A. Christman, San Jose, CA (US); Gerald P. Coleman, Marysville, CA (US)

(73) Assignee: BugLab LLC, Concord, CA (US)

( * ) Notice: Subject to any disclaimer, the term of this patent is extended or adjusted under 35 U.S.C. 154(b) by 27 days.

(21) Appl. No.: 14/691,421

(22) Filed: Apr. 20, 2015

(65) Prior Publication Data

US 2015/0300938 A1 Oct. 22, 2015

Related U.S. Application Data

(60) Provisional application No. 61/982,087, filed on Apr. 21, 2014.

(51) Int. Cl.
*G01N 15/06* (2006.01)
*G01N 15/14* (2006.01)
(Continued)

(52) U.S. Cl.
CPC ............ *G01N 15/06* (2013.01); *G01N 21/51* (2013.01); *C12M 41/36* (2013.01); *G01N 2015/0693* (2013.01)

(58) Field of Classification Search
CPC ................. G01N 15/06; G01N 21/51; G01N 2015/0693; G01N 15/1434; G01N 2021/4709; G01N 2201/0221
See application file for complete search history.

(56) References Cited

U.S. PATENT DOCUMENTS 5,137,693 A 8/1992 Mawhirt et al.
5,483,080 A 1/1996 Tam
(Continued)

FOREIGN PATENT DOCUMENTS

WO WO 81/01467 A1 5/1981

OTHER PUBLICATIONS

International Search Report dated Sep. 16, 2015, in corresponding International Application No. PCT/US2015/026702.
(Continued)

*Primary Examiner* — Sang Nguyen
(74) *Attorney, Agent, or Firm* — Quine Intellectual Property Law Group P.C.; Gary Baker, Esq.

(57) ABSTRACT

This invention provides methods and devices to measure particle suspension concentrations in the presence of potential interferents. Particle back-scatter readings are taken at light wavelengths that are absorbed by the medium before interacting with surrounding objects. Source-detector spacings are minimized compared to the mean absorbance path length of light, thereby maximizing the range of sensitivity to particle concentration. Discrimination against potentially interfering particles, such as bubbles, is provided by mapping the signal distribution against the central signal value and/or by the use of statistical measures with reduced dependence on outliers. The methods and devices allow accurate particle concentration readings over a wide range of concentration in environments crowded with potentially interfering objects and in the presence of variable concentrations and sizes of potentially interfering particles.

30 Claims, 46 Drawing Sheets

(51) Int. Cl.
  *G01N 21/51* (2006.01)
  *C12M 1/34* (2006.01)

(56) References Cited

U.S. PATENT DOCUMENTS

| | | | |
|---|---|---|---|
| 5,532,605 | A | 7/1996 | Dimmick et al. |
| 5,583,635 | A | 12/1996 | Miura et al. |
| 5,632,388 | A | 5/1997 | Morrison et al. |
| 5,779,983 | A | 7/1998 | Dufresne et al. |
| 6,046,814 | A * | 4/2000 | Karlsson ............... G01N 21/255 250/339.13 |
| 6,573,991 | B1 * | 6/2003 | Debreczeny ....... G01N 15/0211 356/336 |
| 7,100,462 | B2 | 9/2006 | Gronvall |
| 8,405,033 | B2 | 3/2013 | Debreczeny |
| 8,603,772 | B2 | 12/2013 | Debreczeny et al. |
| 2005/0173635 | A1 * | 8/2005 | Smith ................ G01N 21/3504 250/339.13 |
| 2008/0061237 | A1 * | 3/2008 | Franz .................... G01J 5/0014 250/339.01 |
| 2008/0204716 | A1 * | 8/2008 | Trainer .............. G01N 15/0205 356/73 |
| 2008/0221711 | A1 * | 9/2008 | Trainer .............. G01N 15/0205 700/54 |
| 2009/0075248 | A1 | 3/2009 | Debreczeny et al. |
| 2012/0194800 | A1 * | 8/2012 | Debreczeny ........... G01N 15/06 356/51 |

OTHER PUBLICATIONS

Arnold, et al. (2002) "Use of At-Line and In-Situ Near-Infrared Spectroscopy to Monitor Biomass in an Industrial Fed-Batch *Escherichia coli* Process." *Biotechnol Bioeng.*, 80(4): 405-413.

Beuermann, et al. (2012) "On-line carbon balance of yeast fermentations using miniaturized optical sensors." *J Biosci Bioeng.*, 113(3): 399-405.

Cervera, et al. (2009) "Application of Near-Infrared Spectroscopy for Monitoring and Control of Cell Culture and Fermentation." *Biotechnol Prog.*, 25(6): 1561-1581.

Crowley, et al. (2005) "Monitoring a high cell density recombinant Pichia pastoris fed-batch bioprocess using transmission and reflectance near infrared spectroscopy." *Enzyme Microb Technol.*, 36: 621-628.

Ge, et al. (1994) "Noninvasive Spectroscopy for Monitoring Cell Density in a Fermentation Process." *Anal. Chem.*, 66(8): 1354-1362.

Kensy, et al. (2009) "Validation of a high-throughput fermentation system based on online monitoring of biomass and fluorescence in continuously shaken microtiter plates." *Microb Cell Fact.*, 8: 31 (1-17).

Kiviharju, et al. (2008) "Biomass measurement online: the performance of in situ measurements and software sensors." *J Ind Microbiol Biotechnol.*, 35: 657.665.

Kunze, et al. (2014) "Pitfalls in optical on-line monitoring for high throughput screening of microbial systems." *Microb Cell Fact.*, 13:53.

Landgrebe, et al. (2010) "On-line infrared spectroscopy for bioprocess monitoring." *Appl Microbiol Biotechnol.*, 88(1): 11-22.

Lourenço, et al. (2012) "Bioreactor monitoring with spectroscopy and chemometrics: a review." *Anal Bioanal Chem.*, 404(4): 1211-1237.

Schmidt-Hager, et al. (2014) "Noninvasive online biomass detector system for cultivation in shake flasks." *Eng. Life Sci.*, 14: 467-476.

Ude, et al. (2014) "Application of an Online-Biomass Sensor in an Optical Multisensory Platform Prototype for Growth Monitoring of Biotechnical Relevant Microorganism and Cell Lines in Single-Use Shake Flasks." *Sensors*, 14(9): 17390-17405.

Zimmermann, H. and Raebiger, T. (2006) "Evaluation of the applicability of backscattered light measurements to the determination of microbial cell densities in microtiter plates." *Anal Bioanal Chem.*, 386(7-8): 2245-2247.

\* cited by examiner

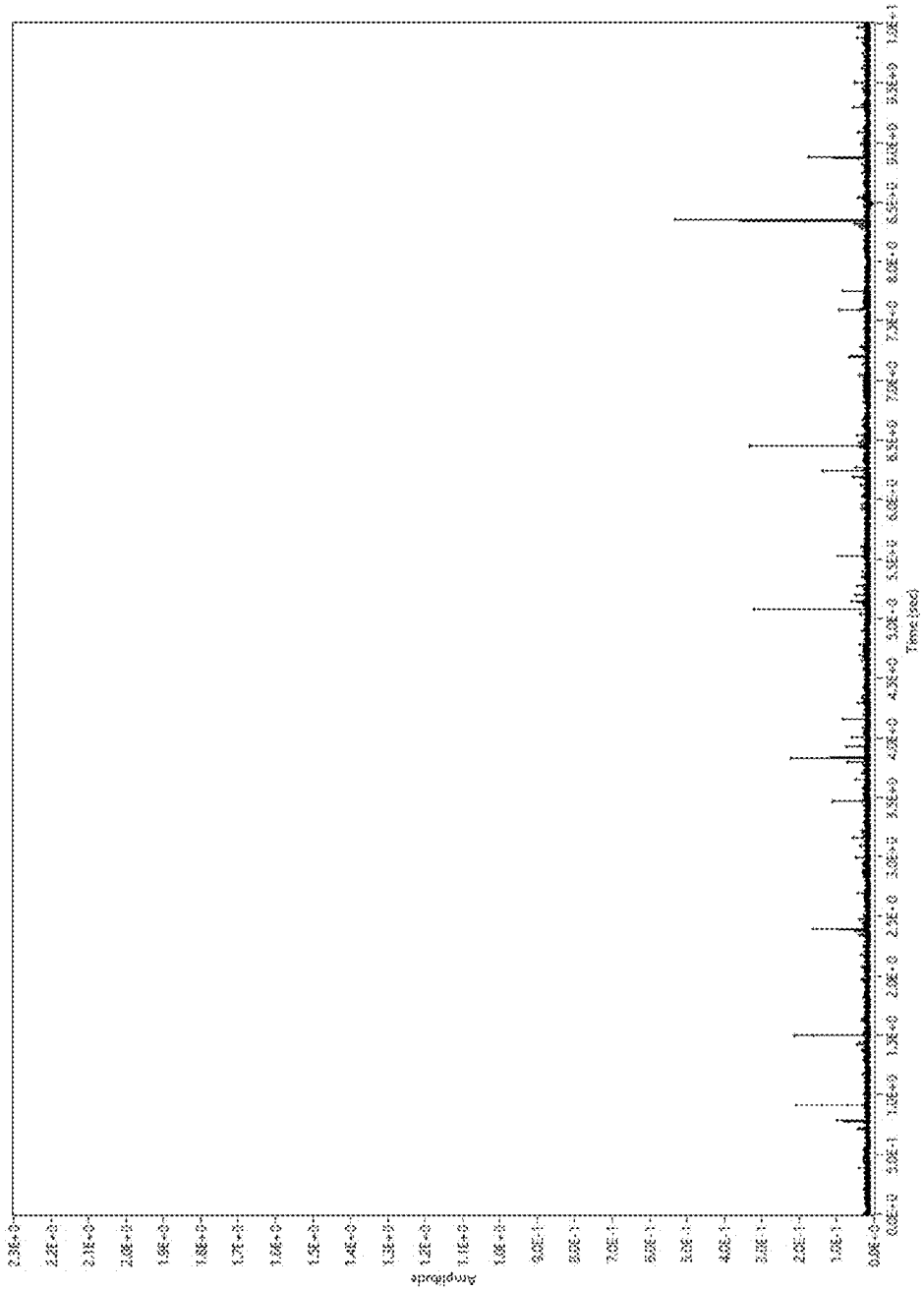

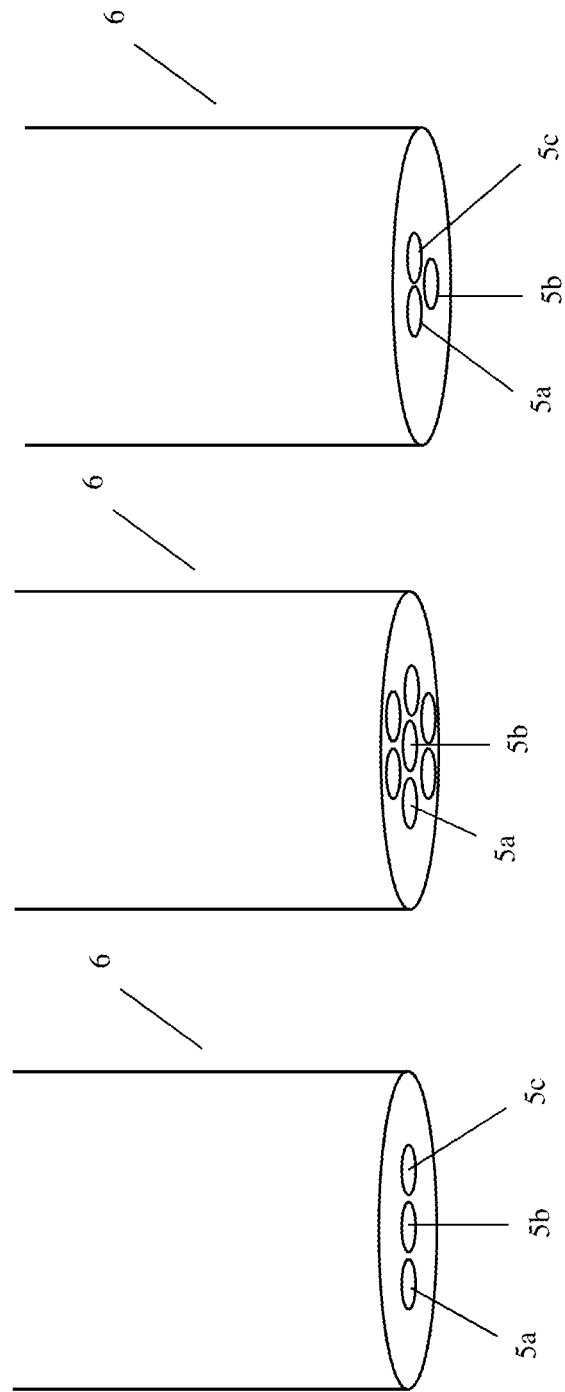

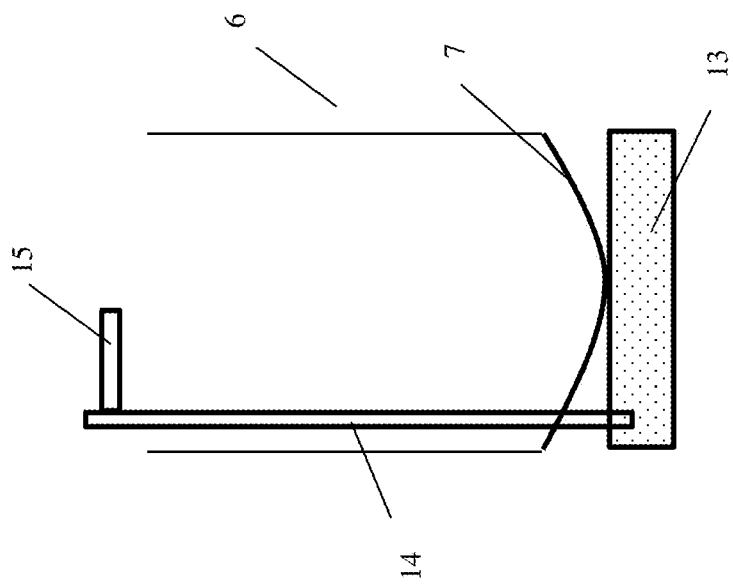
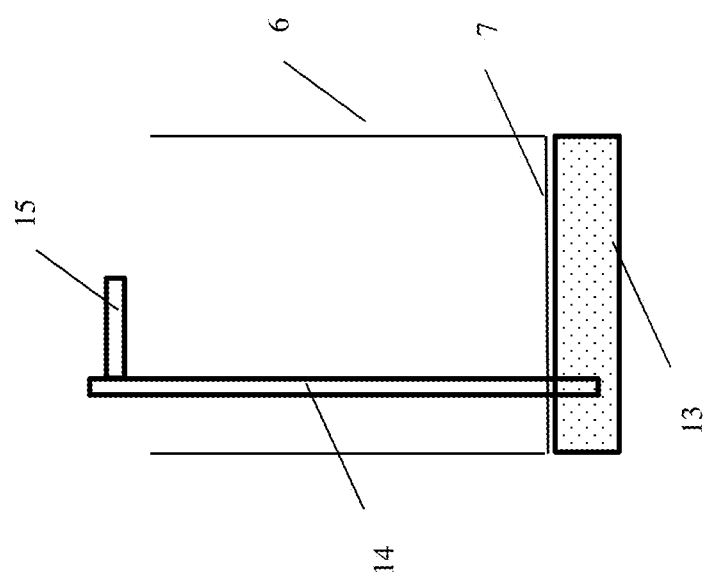
Fig. 12A
Fig. 12B

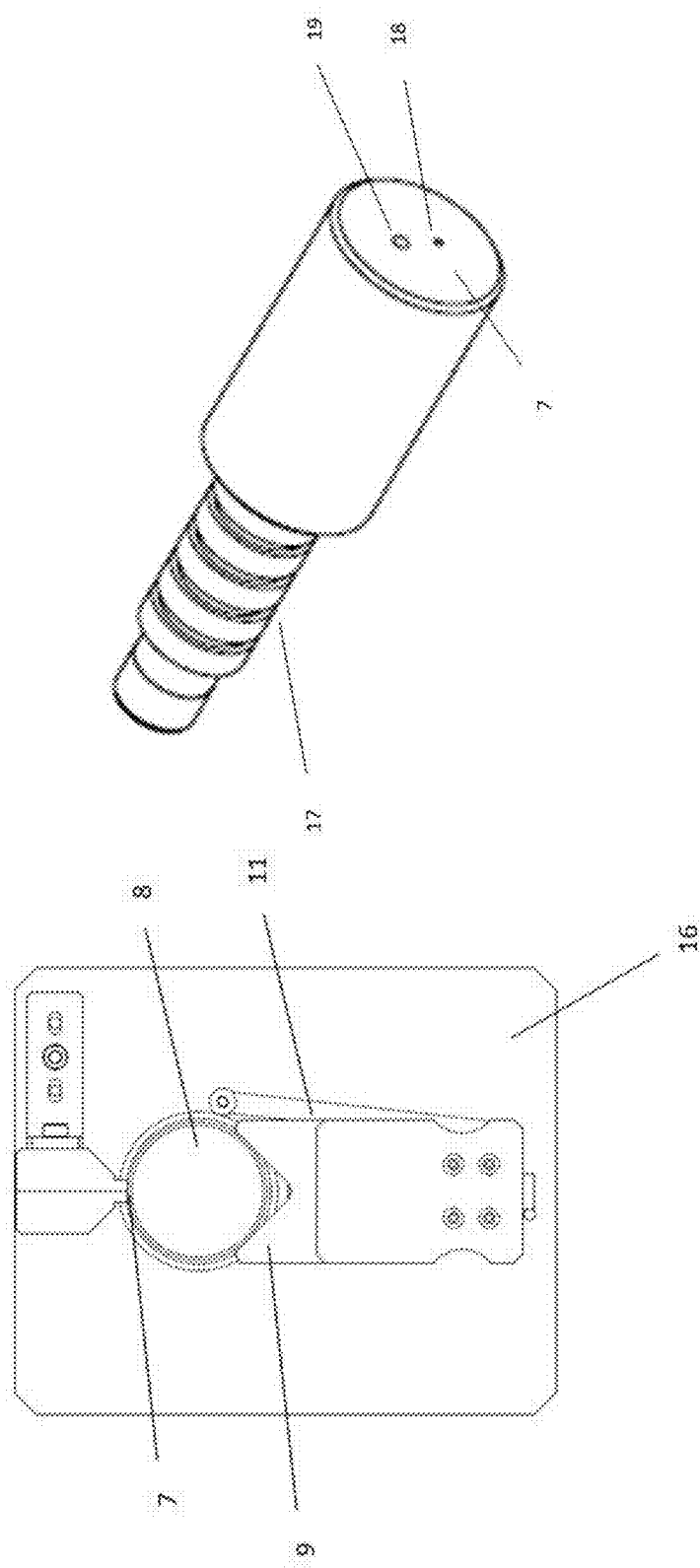

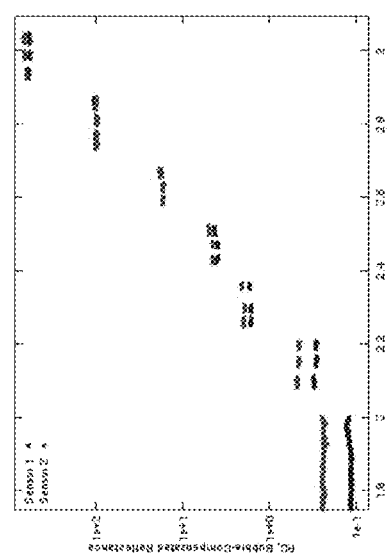
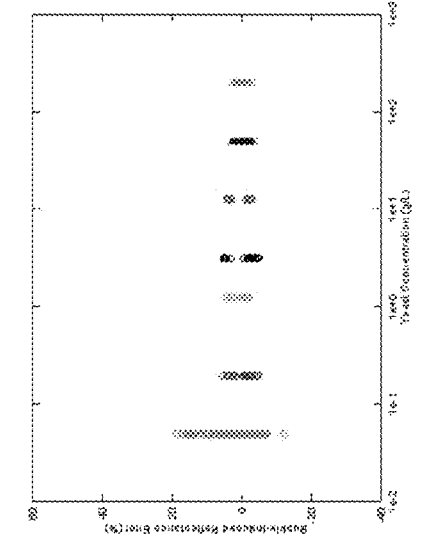
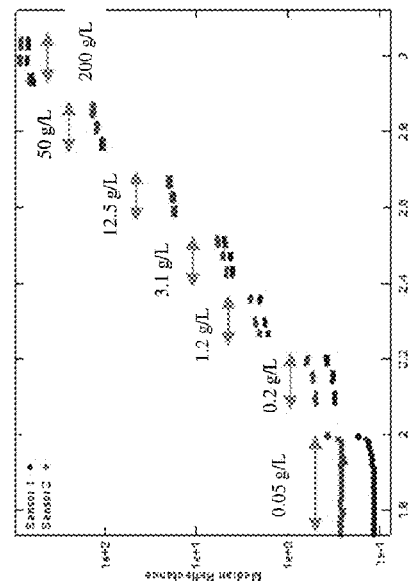
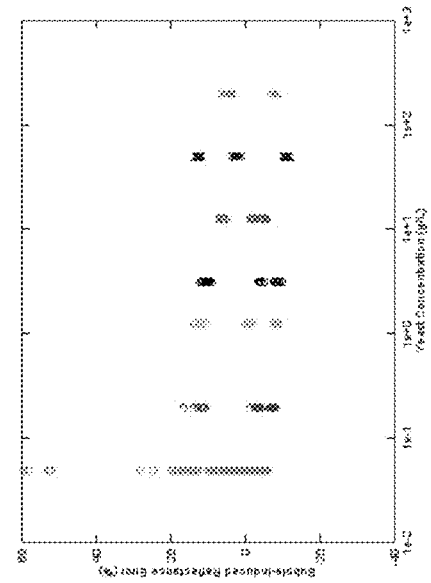
Fig. 16

After bubble correction:
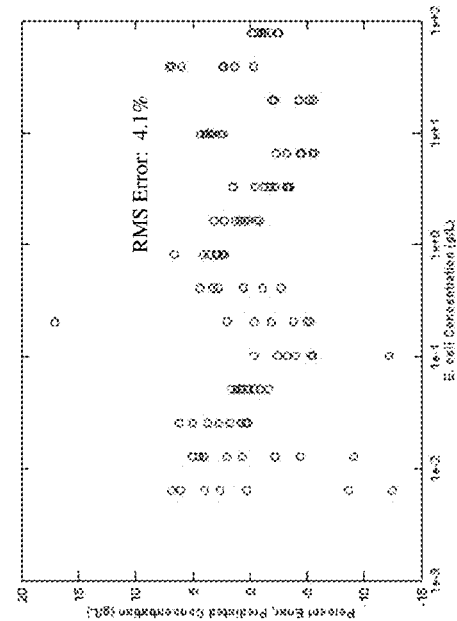
Before bubble correction:
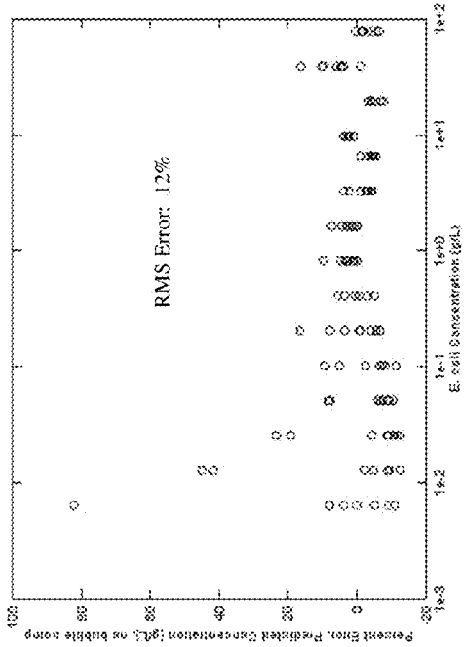
Fig. 20

PARTICLE SENSOR WITH INTERFERENT DISCRIMINATION

CROSS-REFERENCE TO RELATED APPLICATIONS

This application is related to, and claims benefit of, U.S. Provisional Patent Application Ser. No. 61/982,087 filed Apr. 21, 2014, the disclosure of which is incorporated herein by reference in its entirety for all purposes.

FIELD OF THE INVENTION

Methods and devices for accurately measuring particulate concentrations in a suspension, e.g. biomass in a liquid cell culture, that may include moving interfering objects, such as bubbles, and stationary interfering objects, such as immersed sensors. Measurements of particle concentration are made, e.g., by detection of near infrared (NIR) back-scattered light. Detected signals can be related to, e.g., particle concentration, biomass, or standard O.D. 600 nm values.

BACKGROUND OF THE INVENTION

Measurement of particle concentration is important in many industrial and research applications. For example, monitoring cell density (e.g. biomass) in liquid cell cultures is used: to determine the growth phase or rate; as a feedback signal for adjusting growth conditions (e.g. dissolved oxygen, pH, media constituents); and/or as an indicator of when to induce expression of genes, harvest cells, or inoculate cells into a larger media volume. The growth rate of many cultures, particularly microbial organisms (e.g. yeast, bacteria), is limited by the concentration of dissolved oxygen in the medium. The culture of such organisms is often performed in vessels (e.g. fermenters, bioreactors) in which gases are bubbled ("sparged") and the medium is stirred or otherwise agitated, often at such high rates that the bubbles constitute a significant fraction ("gas hold-up") of the total volume. The presence of such a high concentration of bubbles presents a challenge to many techniques for cell growth monitoring.

Many biomass monitoring techniques take advantage of the scattering of light by cells. For example, one of the most common laboratory techniques for monitoring cell growth is to extract a sample, dilute it, and measure it's absorbance (e.g. at 600 nm) in a fixed path length (e.g. 1 cm) cell in a spectrophotometer. Absorbance is typically limited to about 0.5 in order to remain in the linear range of Beer's Law. The measured absorbance multiplied by the dilution factor is referred to as the optical density (e.g. "OD(600 nm)"), and used as an indication of biomass. Despite its prevalence, this technique has numerous limitations: it requires opening the culture, with the attendant risk of contamination; the dilution step is subject to volumetric error; the extracted sample is expended, of particular concern in small volume cultures; and it is labor-intensive.

In an effort to overcome these limitations and provide continuous ("on-line") monitoring, much work has gone into the development of invasive sensors for measuring optical density directly in the cell culture. Unfortunately, such sensors are subject to the same limitation of narrow linear range as are off-line techniques: in order to measure biomass over a wide range, the use of multiple sensors, having different optical transmission path lengths, is frequently required. Immersible sensors that measure back-reflected light (instead of transmission) typically have a somewhat wider but still limited linear range of response to biomass, and may suffer, particularly in the low biomass range, from a sensitivity to reflections from nearby non-biological objects within the vessel, such as impellers, pH sensors, etc. This can render the sensors inaccurate, in an unpredictable way.

Methods for monitoring biomass non-invasively, through the vessel wall, or through an optical window, have been developed in recent years. In U.S. Pat. No. 7,100,462 "Self Adjusting Sensor Mounting Device", methods and devices are described for reproducibly mounting a sensor to a wide variety of cylindrical and flat surfaces in a manner that automatically compensates for the curvature of the mounting surface.

In U.S. Pat. No. 8,603,772, "Particle sensor with wide linear range", methods and devices are described for measuring particulate concentration in vessels, where the response from multiple source-detector pairs is combined to provide a linear response over a wide range of particle concentrations. Also described, are methods and devices for confining the measurement to a specific volume within the medium, as methods and devices for performing rapid sequential measurement of particle concentration in multiple vessels.

In U.S. Pat. No. 8,405,033 "Optical sensor for rapid determination of particulate concentration", methods and devices are described for limiting the optical penetration depth of measurements of particle density by the use of light at wavelengths that are strongly absorbed by the medium, and matching the source-detector separation to the absorbance path length.

In view of the above, a need exists for devices that can read particulate concentrations accurately in the presence of bubbles as well as other nearby reflective objects, that is not prone to fouling, and that is linear over a wide range of biomass. Benefits could also be realized from methods and devices capable of reading particle concentrations in shallow samples and without the need to dilute the sample, or employ multiple sensors. The present invention provides these and other features that will be apparent upon review of the following.

SUMMARY OF THE INVENTION

An optical sensor for accurately measuring the concentration of particles suspended in a medium while mitigating interference from other objects in the medium is disclosed. The sensor consists of one or more light sources and one or more detectors contained in a housing. The light sources and detectors are selected to emit and detect light in a spectral region that is substantially absorbed by the medium, thereby confining the measurement to a restricted volume within the medium. In some embodiments statistical measures of the central value and distribution of the detected light signal are combined to provide discrimination between particle types. Additionally described are methods and devices for accurately determining the particle concentration over a wide range of particle concentrations.

Methods of the invention can include selecting the source wavelength to have a mean absorption path length in the medium that is substantially greater than the separation between the central optical axes of the light source and detector at the interface with the medium, while at the same time being substantially smaller than the distance between the optical interface with the medium and the nearest potentially interfering stationary object falling within the emission cone of the light source.

In specific embodiments in which the medium is aqueous and the suspended particle to be measured is biological (i.e. cells, micro-organisms, etc.), selection of source wavelength(s) having sufficient absorbance by water so that the emitted light is substantially attenuated before interacting with non-biological objects in the container prevents these objects from influencing measurement of the biological particles. By also selecting the source-detector separation to be substantially less than the mean absorption path length, a wide range of sensitivity to changes in biological particle concentration is allowed.

In certain embodiments the medium includes more than one type of particle, and discrimination between the particle types is enabled. In some such embodiments the detection bandwidth and measurement volume are restricted so that signal fluctuations due to a second particle type of particle are observed, whereas the signal due to a first particle type is substantially constant at a given concentration. In some embodiments, the medium is aqueous and the first particle type is a biological particle and the second particle type is a gas bubble. The measurement volume and detection bandwidth are selected so that the fluctuations due to gas bubbles are detected as the number or size of the bubbles within the measurement field varies. The biological particles within the same measurement volume may be substantially smaller and more numerous than the gas bubbles, so that the detected fluctuations due to the biological particles is substantially less than that of the bubbles.

In some embodiments the detected signals as characterized according to their central value. In further embodiments, the method for determining the central value has reduced sensitivity to outliers compared to the mean. Examples of such methods are the median, mode, and trimmed mean. Such methods may provide the ability to discriminate between different particle types, particularly in situations where the particle types have different signal distributions. In other embodiments, the detected signals are further characterized according to their distribution. The central value and distribution estimates may be combined to determine the concentration of a particle type, while being substantially insensitive to the concentration of another particle type.

The methods can further include a means of detecting the position or orientation of the sensor relative to the container, or providing means of reducing the sensitivity of the measurement result to variations in the thickness of the window. The method can include providing means of detecting the position and orientation of the sensor relative to the container. For example, one or more position switches can provide means to determine the position or orientation of the sensor relative to the container. Optionally, one or more capacitance switches can provide a means to determine the position or orientation of the sensor relative to the container. For example, the capacitance switches can be used to determine that a sufficient volume of medium is present in the vicinity of the sensor for a particle concentration measurement to be made accurately. Alternately, the position or orientation can be determined using optical components, such as a light source and detector.

In certain embodiments, radiation sources and sensors are positioned symmetrically about their counterpart. For example, at least two sources can be positioned symmetrically with respect to a detector component, or vice versa. Such devices can reduce inconsistent detections or detect positioning errors during analysis of a sample. For example, the two symmetrically positioned optical elements can provide a means of determining whether sufficient medium is present in order to make an accurate measurement of particle concentration. Comparison of the two or more measurements may also provide a means of detecting obstructions or interferences at or near the optical interface. For example a stationary bubble or debris in the vicinity of the optical elements may have different effect on the measurements at different locations. Such comparison may be useful for excluding or reducing the influence of measurements made under conditions where such interferents are present.

In preferred embodiments, the radiation is detected as back-scattered light and the result is converted to an optical density readout. In many embodiments, absorbing components of the medium being analyzed include water.

In many embodiments of the methods, a means is provided for subtracting a measurement of blank media from a measurement of media containing particulate matter. In preferred embodiments, coefficients can be input or determined relating detected signals to the particle concentration measurement. In the methods, it is beneficial to provide a means of checking for or correcting for proper instrument performance, e.g., by providing duplicate measurements, measurements from different light paths, comparison to standard references, comparison to controls, etc.

In certain methods, a guide is provided for guiding the sensor into a desired alignment with the container. In preferred embodiments, the guide includes a U or V-shaped feature in one dimension and a substantially flat feature in a second dimension, e.g., to align the sensor relative to the axis of a sample container. In some embodiments, spring force is used to hold the guide against the sensor. In many embodiments, the guide is located on the opposite side of the container from the sensor, so that multiple different container sizes may be automatically accommodated.

In one embodiment, the sensor consists of at least one near-infrared laser light source emitting near 1550 nm, and at least one optical reflectance detector. The sensor is held against the wall of a vessel, such as a test tube, containing cells or microorganisms suspended in an aqueous medium. Laser light is directed through the wall of the vessel into the medium and is scattered by the cells or microorganisms. In addition to scattering, the 1550 nm light is partially absorbed by water in the medium. The relationship between Optical Density and the reflectance signal measured by the sensor is stored as a calibration in the instrument, which may vary according to the type of cell or microorganism being grown in the medium. In some embodiments, a baseline offset is provided to allow compensation for the contribution of the medium to the measured Optical Density.

In preferred embodiments, the radiation source emits light at a frequency ranging from about 650 nm to 2200 nm, from 700 nm to 2000 nm, from 800 nm to 1800 nm, from 1000 nm to 1600 nm, or about 1500 nm. In preferred embodiments, the source provides light radiation in the infrared wavelengths. In some embodiments the source provides radiation ranging between 1150 nm and 1350 nm. In other embodiments, the source emits light at a wavelength between 920 and 1150 nm, or between 350 and 1900 nm.

In some embodiments a second reflectance or scatter detector is arranged symmetrically with respect to a first reflectance detector, as a means to determine proper sensor positioning. Comparison of the processed signals from the two detectors ensures that the measurement is being made from within a sufficient depth of fluid to provide accurate determination of particle concentration, and that interfering objects are not present at or near interface between the sensor and container. In some embodiments additional detectors are spaced at a different distance from the laser to extend the linear range of response to changes in particle concentration.

In some embodiments the reflectance detectors are held at the end of apertures constructed from a material, which is strongly absorptive of light emitted by the source. The optic axes of the laser and reflectance detectors may be oriented parallel to each other, and the divergence and collection angles restricted, so as to minimize sensitivity to vessel wall thickness and restrict the measurement volume within the medium.

In some embodiments, the sensor includes at least one position detector. The position detector(s) on the sensor face provide a means of determining when proper sensor positioning has been achieved, and can also be used to trigger a measurement and to help determine whether a measurement has been successfully completed. In some embodiments the position sensor includes at least one position switch. In other embodiments the position sensor includes at least one capacitance sensor. In some embodiments the capacitance sensor is used to determine whether sufficient medium is present in the vessel in proximity to the sensor in order for an accurate measurement to be collected. In other embodiments, the position sensing is performed using optical components.

In some embodiments the concentration is reported as an Optical Density (OD) such as would be reported by a spectrophotometer at a particular wavelength (e.g., 600 nm) through a 1 cm path length cell containing a dilute solution of the medium, after multiplication by the dilution factor. In some embodiments the concentration is reported as standard turbidity units (e.g., NFUs), dry or wet weight per volume (e.g., g/mL), cells counts per volume (e.g., cell/mL), or any user-defined value, related to particle concentration. In some embodiments the type of units in which the result is reported is user-selectable.

The light scatter by particles in the methods can be detected by any appropriate type of detector. For example, detection can be by a photomultiplier tube, photodiode, or photodiode array. In preferred embodiments, at least one of the detectors employs silicon in active detector area of its sensor. In some embodiments, at least one of the detectors employs InGaAs in its active area.

The illumination source in the methods can be any appropriate means, such as, e.g., a laser, a tungsten lamp, mercury vapor lamp, LED, diode lasers and/or the like. In certain embodiments, a monitoring diode is built into the illumination source, and is used to compensate for changes in radiant flux emitted by the source, e.g., a laser monitoring detector is used to directly measure the output of the laser, providing a means of compensating for intensity variation such as may be caused by temperature fluctuations.

In some methods of the invention, a bar code scanner is built into the device and used to track the measurements, e.g., the identification of samples. In the methods, it can be useful to have information transferred wirelessly, e.g., the measured particle concentration can be wirelessly transferred to an ancillary or peripheral device.

In another embodiment of the methods, a concentration of at least one type of particle in a medium is determined by positioning a sensor next to a container holding the medium, passing radiation originating from at least one source through the container wall into the medium that substantially absorbs the radiation, detecting with at least one detector a signal relating to radiation reflected from within said medium back through the container wall, and relating the detected radiation signals to the concentration of a particle in the medium.

The inventions include devices for detecting and measuring the concentration of particles in a container. In one aspect, the device for determining the concentration of at least one type of particle in a medium includes, e.g., a housing containing a sensor, including at least one radiation source and at least one radiation detector positioned to collect source radiation scattered by particles within said medium, wherein the radiation emitted by the source is substantially absorbed by the medium. The device further comprises a controller for controlling the radiation sources, and for measuring at least one of the signals corresponding to the portion of radiation detected by one of the detectors that originated from the radiation sources. The device typically also includes a processor configured to relate at least one of the signals to a concentration of at least one type of particle.

The device sensor can be configured to be well-adapted to taking measurements from any number of different containers or vessels. For example, the sensor housing can be attached to a disposable fermentor, bioreactor, flask, bottle, bag, or tube. The sensor housing can be affixed to a vessel, providing the capability of making multiple measurements without the need for reapplication of the sensor to the vessel. Multiple sensors can be interfaced with the same controller. In some embodiments, the sensor housing is designed to be disposable. Radiation sources or detectors can be fiber optical components optically linked to electro-optical components that are physically separated from said housing. In some embodiments fiber optics are used to convey light between the sensor and electro-optical components. In some such embodiments fiber optics splitters and/or switchers are used to multiplex the electro-optical components between multiple fibers.

The device can be configured to take particle concentration measurements. In preferred embodiments, the time required for measurement of particle concentration is three seconds or less. In other embodiments, the measurement time is variable, as determined by a metric related to measurement accuracy. In another aspect, signals are combined from source-detector pairs with at least two different separation distances. In another aspect, at least two of the radiation sources have substantially different emission wavelengths. In certain devices, the source wavelengths can be selected according to the separation between the source-detector pairs.

In some embodiments the sensor is immersed in the medium. In some such embodiments the materials comprising the sensor face include glass. In some such embodiments the glass is curved so as to discourage the accumulation of objects on the exposed surface. In embodiments where the sensor is immersed in a liquid medium, the use of a glass face, particularly with a curved shape, discourages the accumulation of gas bubbles or debris on the exposed surface. In other embodiments the materials comprising the sensor face include stainless steel that has been coated with a material, such as titanium or zirconium nitride, that discourages the accumulation of bubbles or biological material on the sensor surface.

In some embodiments fiber optics are used to aid in the transport of light from the light source(s) and to the detector(s). This may allow the optical components to be positioned remotely from the point of optical interface with the medium.

Definitions

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "feed" can include mixtures of feed, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

The sensors described herein include some embodiments in which the light source and detector are physically located within the sensor ("free-space embodiments"), and other embodiments in which the light source and detector are located outside of the sensor, and light is conveyed to and from the sensor through the use of fiber optics, which may include single fibers or bundles of fibers ("fiber-optic embodiments"). As used herein, when reference is made to a "light source" or "detector" in a sensor, in addition to free-space embodiments the meaning also encompasses fiber optic embodiments, where the fiber optics act as an extension of the light source and/or detector.

As used herein, an "absorption coefficient" of a medium is the negative of the logarithm of the ratio of light transmitted through the medium to the light transmitted in the absence of the medium, divided by the path length travelled through the medium.

As used herein, an "detection cone" of a detector is the cone of detection rays surrounding the central optical axis of the detector at which the detected intensity is half that detected at the central optical axis.

As used herein, an "emission cone" of a light source is the cone of emission rays surrounding the central optical axis of the light source at which the light source intensity is half that at that the central optical axis.

As used herein, a "mean absorption path length" in a medium is the inverse of the absorption coefficient of the medium.

A "sensor" of the methods and devices is a device component comprising at least one light source-detector pair in functional association.

As used herein, "modulated" means to vary the amplitude, frequency, or phase of a light source.

As used herein, "substantially" refers to largely or predominantly, but not necessarily entirely, that which is specified.

The term "about", as used herein, indicates the value of a given quantity can include quantities ranging within 25% of the stated value, or optionally within 10% of the value, or in some embodiments within 1% of the value.

BRIEF DESCRIPTION OF THE DRAWINGS

FIG. 2 is a graph of optical penetration depth as a function of yeast concentration for several configurations of source-detector pairs of the sensor depicted in FIG. 1a.

FIG. 4b is a histogram of the data graphed in FIG. 4a.

FIG. 4e is graph of back-scattering amplitude as a function of time for a fiber optic source-detector pair immersed in fermentor containing 0.4 g/L yeast, with no bubbling. The source and detector fibers are S1 and D1, as depicted in FIG. 1b.

FIG. 11c depicts an embodiment of a sensor of the present invention employing separate fiber optics for light delivery and collection, and a third fiber that can be configured for either light delivery or light collection.

FIG. 11d depicts an embodiment of a sensor of the present invention employing separate fiber optics for light delivery and collection, and five additional fibers that can be configured for either light delivery or light collection.

FIG. 11e depicts an embodiment of a sensor of the present invention employing separate fiber optics for light delivery and collection, and a third fiber in a triangular arrangement that can be configured for either light delivery or light collection.

FIG. 12a is a side view of an embodiment of a sensor of the present invention which includes a flat surface on the sensor face and a scattering reference material held in the closed position.

FIG. 12b is a side view of an embodiment of a sensor of the present invention which includes a rounded surface on the sensor face and a scattering reference material held in the closed position.

FIG. 13c is a top view of an embodiment of a sensor of the present invention designed for measurements through the wall of a test tube.

FIG. 14 is an embodiment of a sensor of the present invention designed for measurements through the wall of a small disposable plastic vessel.

FIG. 16 summarizes results of applying the bubble calibration shown in FIG. 15 to new measurements.

FIG. 20 provides an example of applying the bubble-correction methods of the present invention to provide accurate prediction of *e. coli* concentration.

LIST OF COMPONENTS DEPICTED IN FIGURES

Figure 1A:
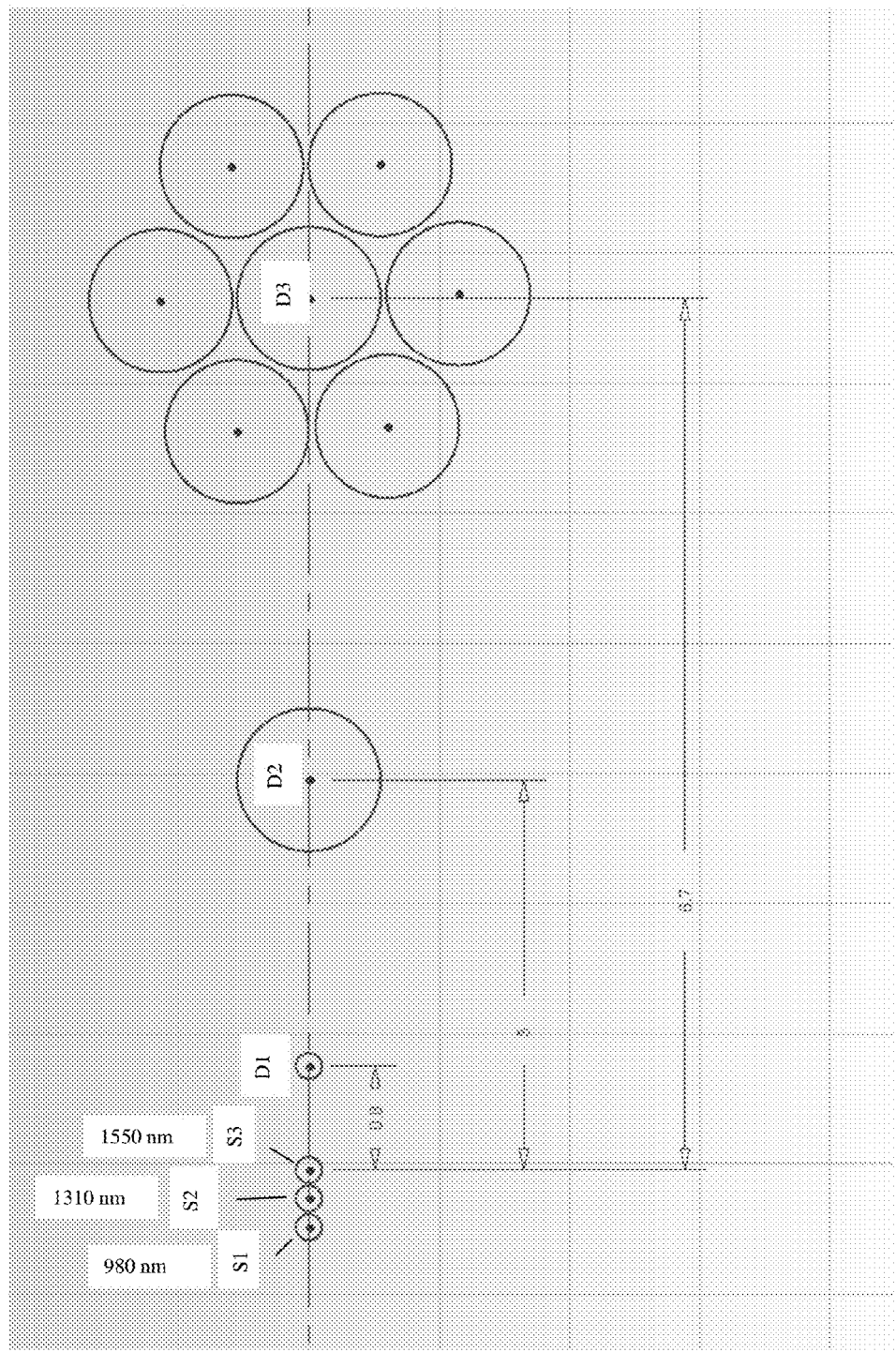
FIG. 1a depicts an end view of a fiber optic sensor used to demonstrate certain aspects of the present invention.

1—Light source
2—Detector
3—Mirror
4—Beam splitter
5—Optical fiber
6—Sensor housing
7—Sensor face
8—Test tube
9—Rear support
10—Rail
11—Spring
12—Bottom aperture
13—Scattering reference
14—Support shaft
15—Turning handle
16—Base
17—Strain relief
18—Single mode optical fiber
19—Multi-mode optical fiber

DETAILED DESCRIPTION

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments as suggested in the present description, and may be satisfactorily applied for the measurement of any material which may exhibit similar behavior that are also intended to be encompassed within the spirit and scope of the invention.

The detailed description set forth herein will make reference to the measurement of biomass in a liquid culture. The term "biomass" as used in this patent application, refers to the concentration of biological material, such as cells or microorganisms. What is meant here and elsewhere in the patent application by "concentration" is the number of a type of particle, weight of a type of material, or volume of a type of material found in a given volume or weight of a medium.

Optical Density (OD) is defined as:

$$OD = -F\log_{10}\left(\frac{I}{I_0}\right)$$

where light intensities are measured after transmission through a medium containing suspended particulate matter (I) and through the same medium in the absence of particulate matter ($I_0$). It is common in the biofermentation field to measure and refer to biomass according to the optical density measured at a particular wavelength, such as 600 nm ("OD600"), through a 1 cm path length cuvette, with a commercial spectrophotometer. When measuring OD using a spectrophotometer it is necessary to dilute the sample to have an OD in a linear range of response (commonly OD<1, but more ideally OD between 0.05 and 0.2) and then scale the measured OD by the dilution factor, F. This type of measurement is herein referred to as "Offline OD" measurement, to distinguish it from the real-time ("Online") measurement allowed by the methods and devices for the present invention. For mono-disperse cells a linear relationship between biomass and OD generally holds.

The method(s) and instrument(s) of the present invention may also find application in liquid suspensions of solids other than biomass as well as in solutions. For example, the particulate content in milk, the rate of polymerization in a chemical system or the turbidity of water may be measured by application of the method(s) and/or instrument(s) of the present invention. Similarly, the present invention may be utilized to determine the amount of gas in a liquid phase, such as the concentration of gas bubbles in a liquid medium. In addition, the attenuation of radiation by absorption may be used to measure the concentration of components dissolved in solution, by application of the present invention.

The method and instruments of the present invention may also be useable in the gas phase. For example, in industrial plants using smokestacks, the amount or concentration of a specific component of the effluent gas may be measured by application of the present invention. As another example, the present invention may be used to measure the particulate content of a gas for the purpose of smoke or fire detection. As yet another example, the present invention may be used to measure the concentration of a particular component of a gas, such as the concentration of carbon dioxide in a mixture of gases or the density of fog or smoke in the flight path of an airplane.

In addition, the method(s) and/or instrument(s) of the present invention may be utilized to monitor materials in the solid state and to monitor transformation of materials between states. For example, the present invention may be used to monitor the conversion of a liquid to the solid state, such as gel formation, or crystallization. Thus, although the hereinafter-set-forth descriptions often refer specifically to the measurement of the biomass in a liquid culture, it will be appreciated that the method(s) and instrument(s) of the present invention are also applicable in other liquids and in gas and solid media applications.

Description of Exemplary Methods

The present methods are generally directed to techniques of illuminating a particulate suspension and determining the particulate concentration in correlation to the amount of back-scattered light. Methods for reducing or avoiding the influence of potential interferents are also provided. Such sources of interference may include objects submerged within the medium, such as other sensors, agitators, sparge tubes, and stirring baffles, as well as the wall of the container holding the medium. Another source of interference may be the presence of one or more additional particle types, such as bubbles, or un-dissolved media constituents.

In many embodiments, the methods comprise using an optical sensor to determine the concentration of particles in a liquid medium held within a container. The medium is irradiated with a light source in the sensor. The light source has an emission wavelength that is absorbed by the medium, as characterized by a mean absorption path length. The sensor also includes one or more detectors that detect source light scattered by particles in the medium. In many embodiments, the spatial separation between the central optical axes of the light source and detector at the optical interface with the medium is substantially less than the mean absorption path length. At the same time, the distance between the optical interface with the medium and the nearest potentially interfering stationary object falling within the emission cone of the light source, is substantially greater than the mean absorption path length. The nearest stationary object can be considered not to include a container wall on the container side through which the media is being illuminated and/or detected. The detected light is then correlated to the concentration of particles in the medium.

Figure 2:
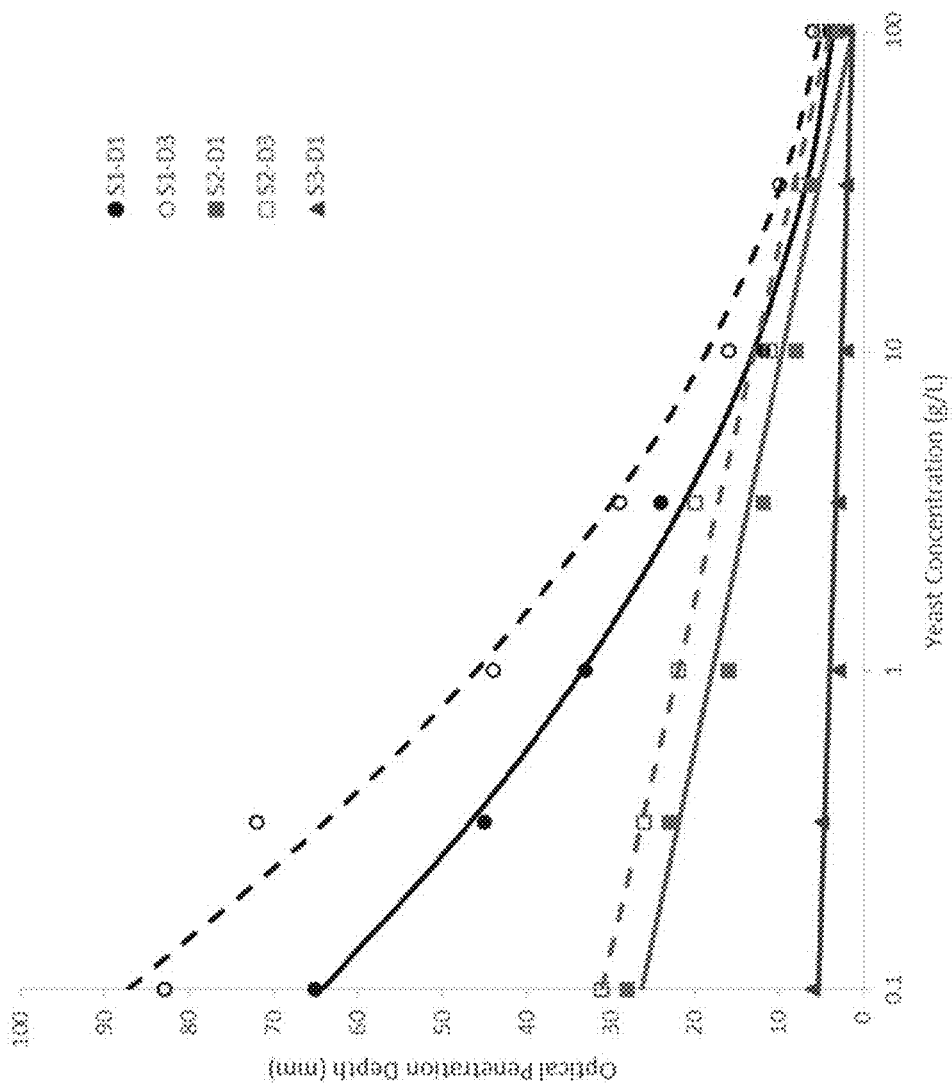

In embodiments where the medium is aqueous, absorption of the source light by water may influence the mean absorption path length ($1/\mu_a$). The mean absorption path length will in turn influence the maximum optical penetration depth—the maximum depth into the medium that the source may penetrate before being attenuated below the detection limit. In some embodiments the source wavelength consists of infrared light that is absorbed by the medium. An example of the influence of the infrared light source wavelength on the optical penetration depth is provided in Example 1 and depicted in FIG. 2. In this example, three near infrared source wavelengths, having increasing water absorption were selected: 980 nm (S1, $1/\mu_a$=21 mm), 1310 nm (S2, $1/\mu_a$=6 mm), and 1550 nm (S3, $1/\mu_a$=0.8 mm). Back-reflected light was collected at two distances from the source (D1~1 mm, D3~7 mm) with the sensor immersed in biomass at a range of concentrations (yeast: 0.1-100 g/L). As shown in FIG. 2, at the lowest biomass concentration, the optical penetration depth at 980 nm (S1), where water absorption is relatively weak, can extend to about 90 mm. At 1550 nm (S3), where the water absorption is relatively strong, the penetration depth is limited to about 6 mm. At 1310 nm (S2), where the water absorption is intermediate between that at 980 and 1550 nm, the penetration depth is about 30 mm. Note that the penetration depth is also influenced to some extent by the source-detector separation, but in this example the choice of source wavelength has a stronger influence. The maximum optical penetration depth is also influenced by the particle concentration in the medium, with the penetration depth typically decreasing with increasing particle concentration, such as shown in FIG. 2.

The maximum optical penetration can alternately be considered as the minimum allowable distance between the optical interface of the sensor with the medium and any potentially interfering objects in the vessel containing the medium (which may include the vessel itself). In many embodiments it will be beneficial to choose the source wavelength so that the distance to potentially interfering objects is at least twice that mean absorption path length. In other embodiments, higher multiples of the mean absorption path length may be used to determine the minimum interference distance. In Example 1, mean absorption path length multiples of about 4, 5, and 7, respectively for source wavelengths of 980, 1310, and 1550 nm, are appropriate for selecting the minimum distance to potentially interfering objects in the medium, when it is desired to determine particle concentration in the lowest concentration range. This path length multiplier can be decreased if the range of biomass concentrations to be measured is restricted to a higher concentration range. In Example 1, if the biomass concentration measurement range is restricted to above 1 g/L or above 10 g/L, an appropriate multiplier may be in the range of 3-5 or 1-3, respectively.

In some embodiments of the invention a collar is placed on an immersible probe to aid the user in achieving a pre-determined depth in the vessel during assembly of the probe onto the vessel. By inserting the probe to the depth defined by the collar, the user is ensured of immersing the probe into the medium, but is prevented from accidentally placing the probe in too close proximity to the bottom of the vessel. In many embodiments the position of this collar is adjustable, according to the vessel size being used. The collar position is pre-set during manufacturer for use on a particular vessel type but may be adjusted by the user for other vessel types. In some embodiments markings are provided on the probe to indicate the collar position that is most appropriate for particular vessels types or sizes.

Figure 3:
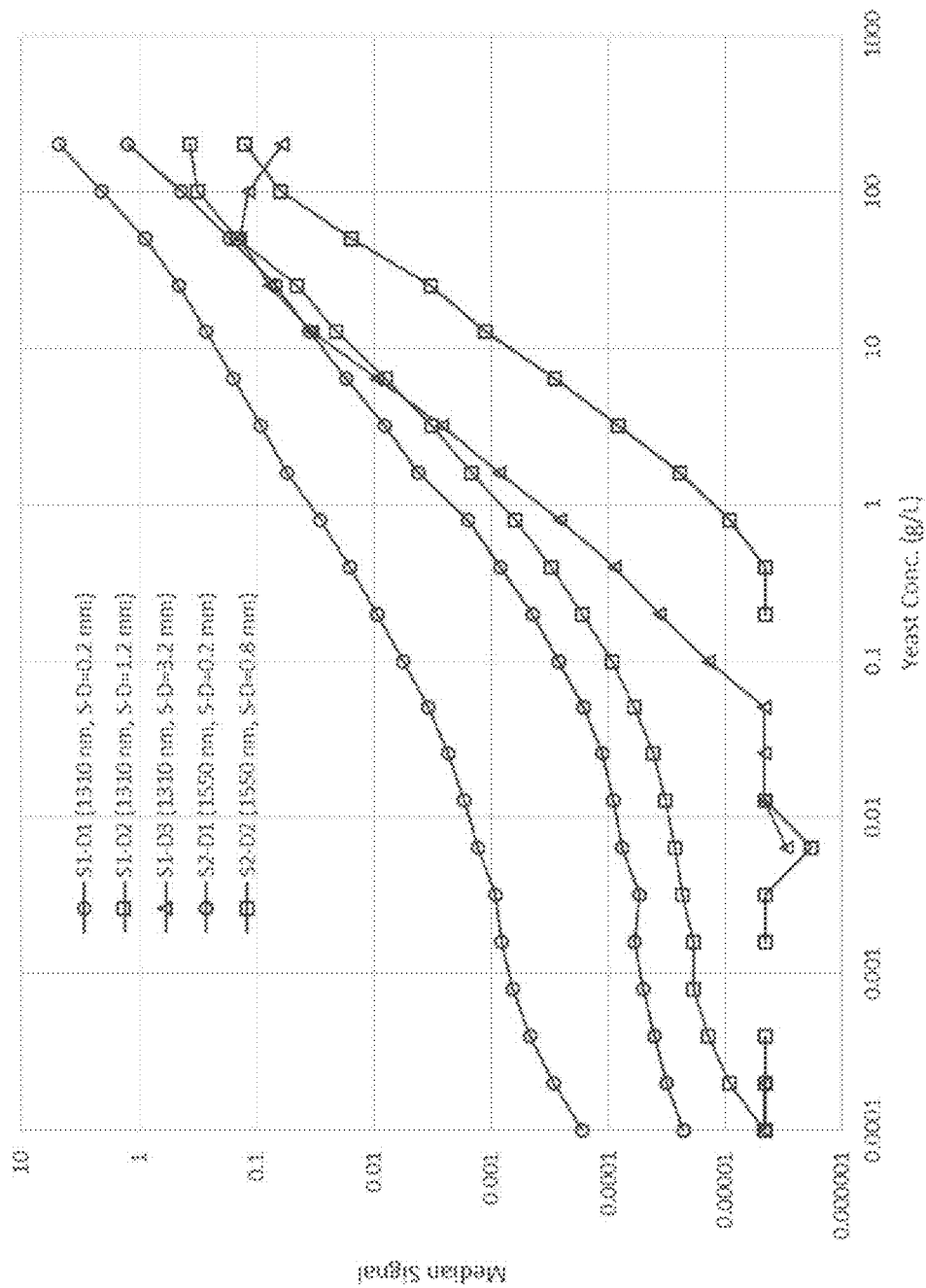
FIG. 3 is a graph of median signal as a function of yeast concentration measured by a sensor of the present invention on a bioreactor.

The choice of the source-detector separation can have a strong influence on the range of particle concentration that is measurable. By configuring the sensor so that the separation between the light source and detector is small compared to the mean absorption path length in the medium, a wide range of particle concentrations may be measurable with the same source-detector pair. Further, the linearity of the measured reflectance signal may be increased by keeping the source-detector separation small. Measurements at two source wavelengths (1310 and 1550 nm) and several source-detector separations (~0.2, ~1, and ~3 mm) are described in Example 2. As shown in FIG. 3, when the source-detector separation was chosen to be comparable to the mean absorption path length (S1-D3 and S2-D2), the range of sensitivity to changes in biomass concentration was limited compared to those configurations where the source-detector separation was selected to be substantially less than the mean absorption path length (e.g. S1-D1 or S2-D1). In many embodiments, in order to achieve the widest range of biomass sensitivity, it will be beneficial to select the source-detector separation to be at least two times smaller than the mean absorption path length. In other embodiments even higher factors may be beneficial. In Example 2, the configurations showing the widest range of sensitivity to biomass changes, S1-D1 and S2-D1, had source-detector separations that were, respectively, 30 and 4 times smaller than the mean absorption path length.

In some embodiments, the method comprises determining the concentration in a medium of a first particle type in the presence of a second particle type. The method includes the steps of passing light originating from a first light source into the medium, and detecting a first light signal originating from the first light source that was reflected from within the medium. Next, a first statistical measure is computed that is related to the central value of the signal, wherein the statistical measure has reduced dependence on outliers compared to the mean of the signal. The first statistical measure is then used to determine the concentration of the first particle type in the medium, with substantially reduced dependence of the concentration of the second particle type compared to that obtained by using the mean as the statistical measure.

Examples of statistical measures with reduced dependence on outliers compared to the mean include the trimmed mean, mode, and median. The trimmed mean is computed by sorting the data, discarding upper and lower ranges of the sorted data, and computing the mean of the remaining points. The trimming percentage may vary according to the application, but as an example, the upper and lower quartile of the data may be discarded ("25% trimmed mean") before computing the mean. The mode may be computed as a single mode or as multiple modes. In such cases, the mode value that is selected may depend on the application. In many applications the minimum mode value in a multi-mode distribution is selected. In many applications the number of bins in the histogram used to compute the mode may also be variable. As an example, the number of bins may be adjusted according different statistical estimates of the distribution and central value of the data. As described in Example 4, one method for determining the number of bins is to divide the full range by the interquartile range with appropriate scaling and offsetting. The interquartile range is the difference between the values of the data points at the $25^{th}$ and $75^{th}$ percentiles of a sorted data set.

An example of the reduced dependence of biomass estimation on the influence of bubbles based on statistical measures other than the mean is provided in Example 4. The data depicted in FIGS. 5d and 5e were collected over a wide range of yeast concentrations, agitation rates, and sparge (bubbling) rates. Each different biomass concentration is depicted with a different symbol. Comparison of the mean values in FIG. 5d with the median values in FIG. 5e, make it evident that the median value at each biomass is less affected by changes in agitation and sparging, than is the mean value. This is particularly evident in the low biomass range (<1 g/L). For example compare the range of mean values observed at a biomass value of 0.2 g/L in FIG. 5d, to the range of median values for the same biomass in FIG. 5e. When using the mean as the central value measure, bubbling has the effect of smearing the data, so that 0.2 g/L cannot be distinguished from 0.1 or 0.4 g/L biomass values. In contrast, when using the median as the central value measure, the biomass points at 0.2 g/L are tightly clustered under all agitation and bubbling conditions, and are readily distinguished and separated from those at 0.1 or 0.4 g/L.

In another exemplary embodiment, the method determines the concentration in a medium of a first particle type in the presence of a second particle type. The method includes the steps of passing light originating from a first light source into the medium, and detecting a first light signal originating from the first light source that was reflected from within the medium. Next, a first statistical measure is computed that is related to the central value of the signal, and a second statistical measure is computed that is related to the distribution of the signal. The first and second statistical measures are then combined to determine the concentration of the first particle type in the medium, and is substantially independent of the concentration of the second particle type.

Figure 5A:
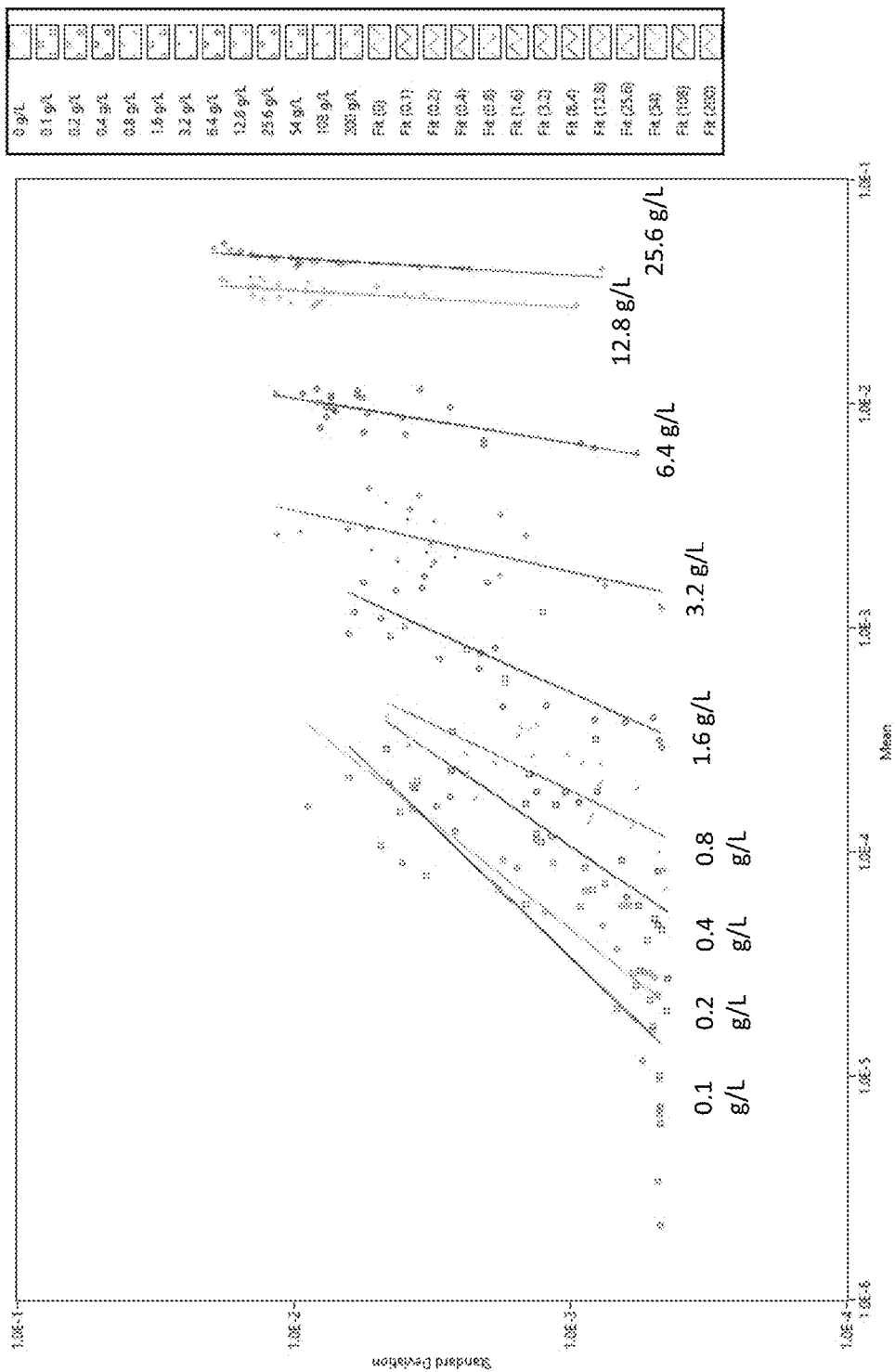
FIG. 5a is a graph of standard deviation as a function of mean value measured with a sensor of the present invention having a source wavelength of 1310 nm, and a source-detector separation of about 7 mm (S1-D4 in FIG. 1b), that was immersed in a 12 L bioreactor containing various concentrations of yeast dissolved in 10 L of 0.9% saline, and agitated and sparged with air over a wide range of settings (400-900 rpm, 0-16 lpm, respectively). Measurements made at the same yeast concentration (but differing sparge and agitation) are represented with markers having the same shape and color.
Figure 5B:
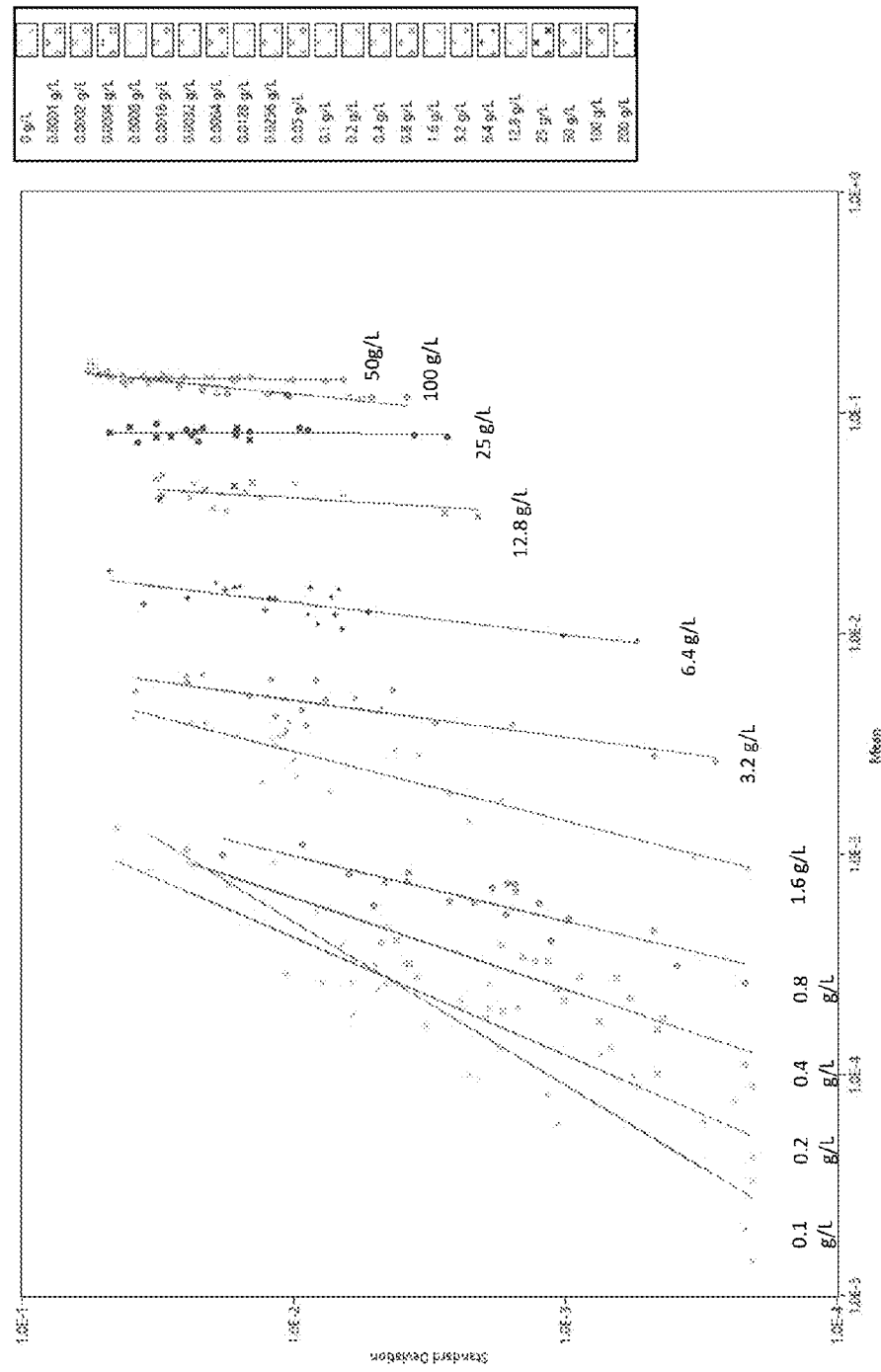
FIG. 5b is a graph of standard deviation as a function of mean value measured with a sensor of the present invention having a source wavelength of 1310 nm, and a source-detector separation of about 3.4 mm (S1-D3 in FIG. 1b), that was immersed in a 12 L bioreactor containing various concentrations of yeast dissolved in 10 L of 0.9% saline, and agitated and sparged with air over a wide range of settings (400-900 rpm, 0-16 lpm, respectively). Measurements made at the same yeast concentration (but differing sparge and agitation) are represented with markers having the same shape and color.
Figure 5C:
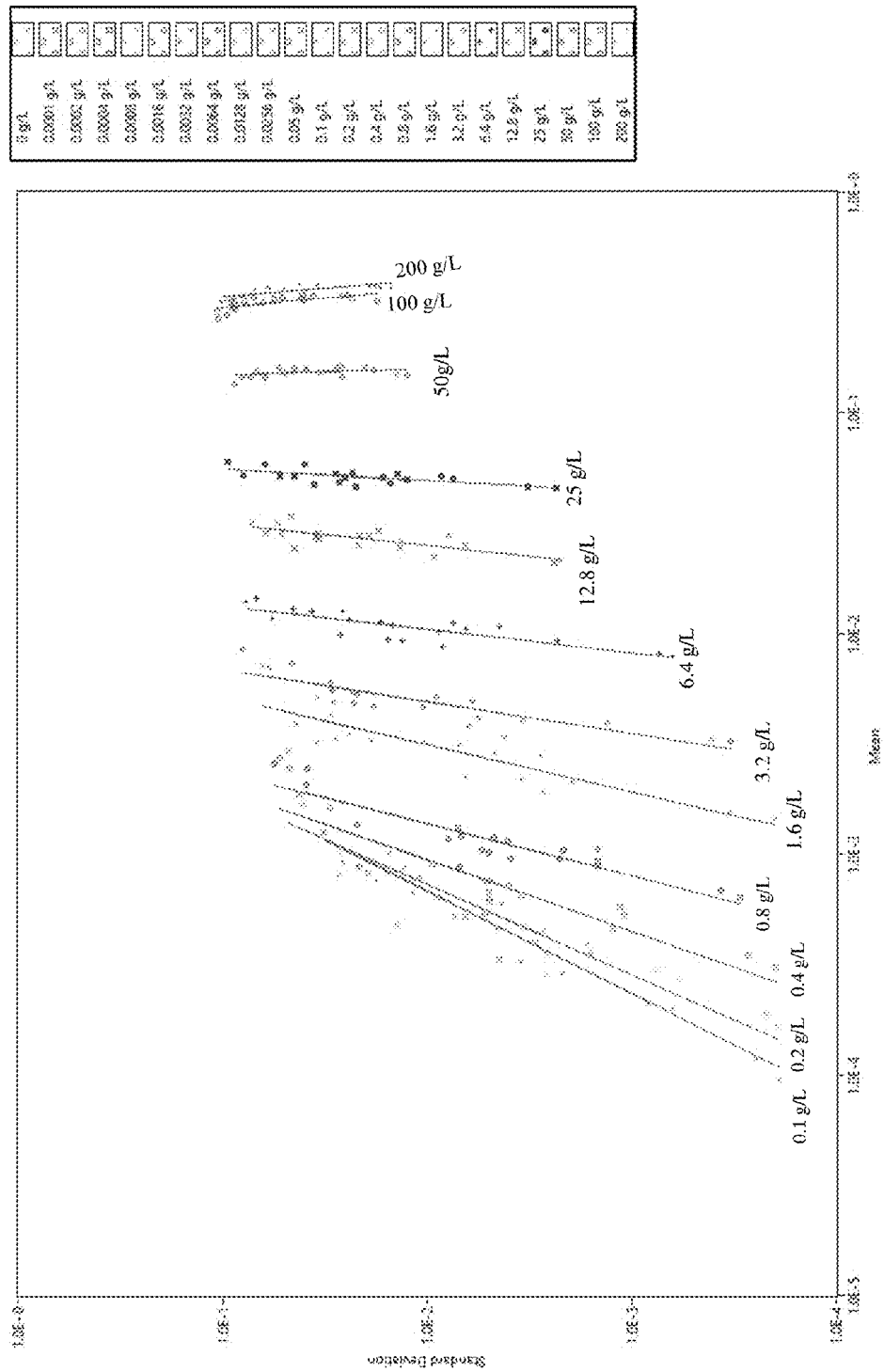
FIG. 5c is a graph of standard deviation as a function of mean value measured with a sensor of the present invention having a source wavelength of 1310 nm, and a source-detector separation of about 1.2 mm (S1-D2 in FIG. 1b), that was immersed in a 12 L bioreactor containing various concentrations of yeast dissolved in 10 L of 0.9% saline, and agitated and sparged with air over a wide range of settings (400-900 rpm, 0-16 lpm, respectively). Measurements made at the same yeast concentration (but differing sparge and agitation) are represented with markers having the same shape and color.
Figure 5D:
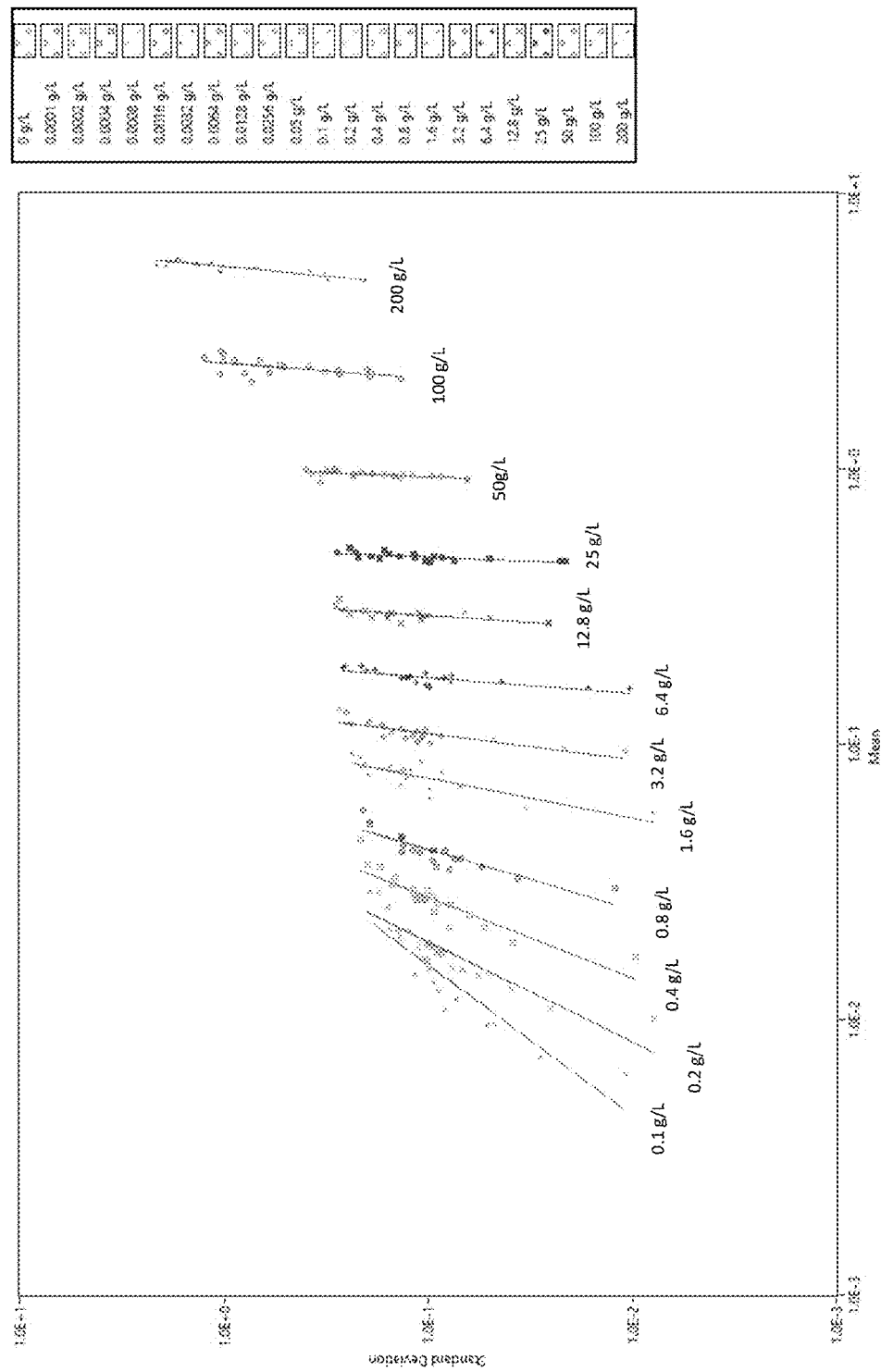
FIG. 5d is a graph of standard deviation as a function of mean value measured with a sensor of the present invention having a source wavelength of 1310 nm, and a source-detector separation of about 0.22 mm (S1-D1 in FIG. 1b), that was immersed in a 12 L bioreactor containing various concentrations of yeast dissolved in 10 L of 0.9% saline, and agitated and sparged with air over a wide range of settings (400-900 rpm, 0-16 lpm, respectively). Measurements made at the same yeast concentration (but differing sparge and agitation) are represented with markers having the same shape and color.
Figure 5E:
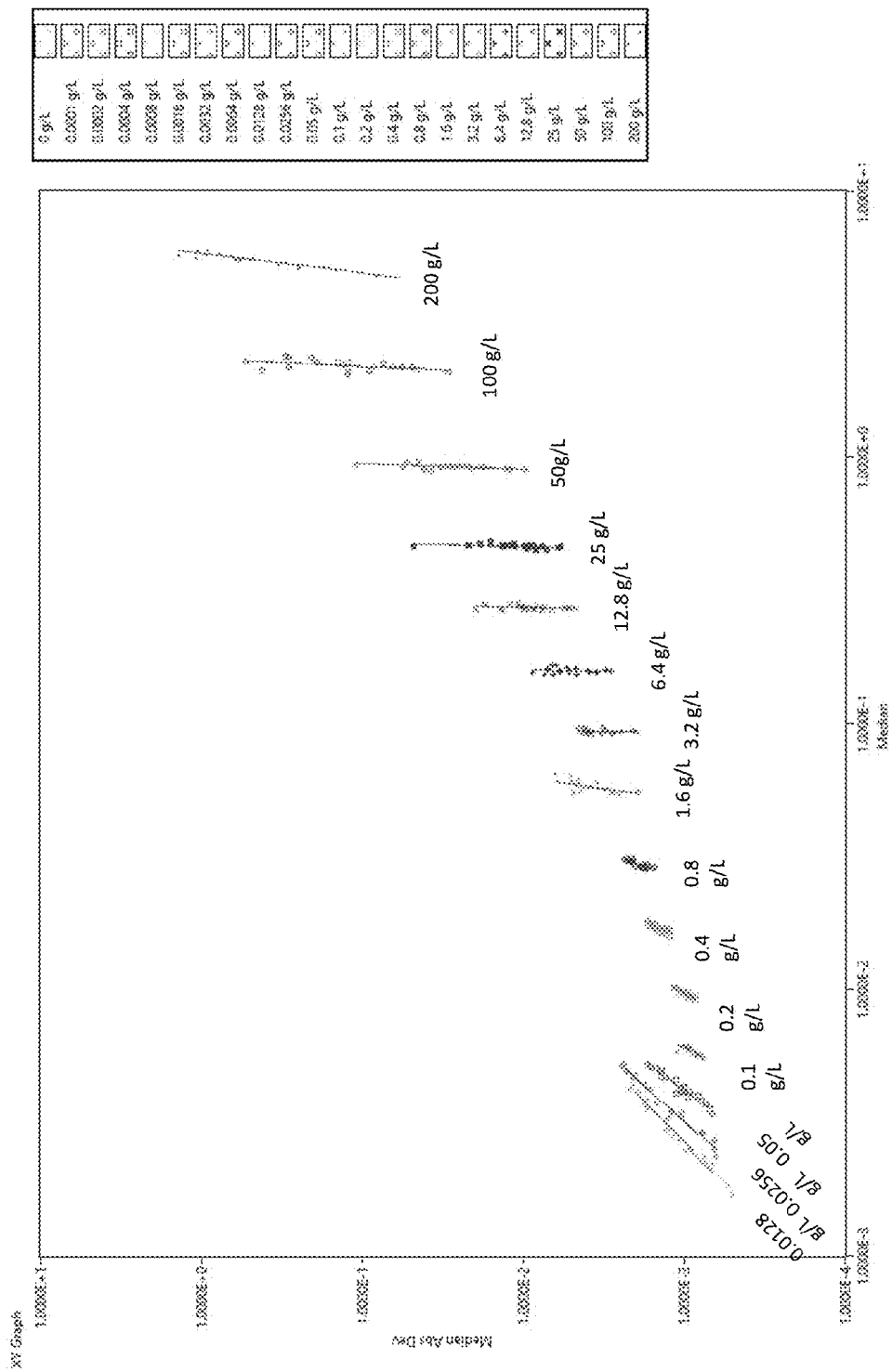
FIG. 5e is a graph of median absolute deviation as a function of median value measured with a sensor of the present invention having a source wavelength of 1310 nm, and a source-detector separation of about 0.22 mm, that was immersed in a 12 L bioreactor containing various concentrations of yeast dissolved in 10 L of 0.9% saline, and agitated and sparged with air over a wide range of settings (400-900 rpm, 0-16 lpm, respectively). Measurements made at the same yeast concentration (but differing sparge and agitation) are represented with markers having the same shape and color.

Examples of statistical measures related to the central value of the signal include the mean, trimmed mean, mode, and median. Examples of statistical measures related to the distribution of the signal include the standard deviation, range, interquartile range, mean absolute deviation, median absolute deviation, and mode absolute deviation. Examples of the reduced dependence of biomass estimation on the influence of bubbles based on combining statistical measures of the distribution and central value are provided in Example 4. For example, FIG. 5e depicts the median absolute deviation plotted versus the median signal over a wide range of biomass concentrations, agitation rates, and sparging rates. The points at each biomass level are well clustered on the plot, so that the biomass can be distinguished despite the influence of bubbles. Measurement of biomass that is substantially independent of bubble influence can therefore be accomplished by mapping of the biomass range onto a plot of signal distribution and central value. In some embodiments this mapping consists of a series of lines used to characterize each biomass value. In other embodiments, one or more analytical functions are empirically derived that characterize the biomass as a function of the central value and distribution. In one such embodiment, two analytical functions are empirically derived, one that characterizes the slope and another that characterizes the intercept of the lines through each biomass value.

Figure 15:
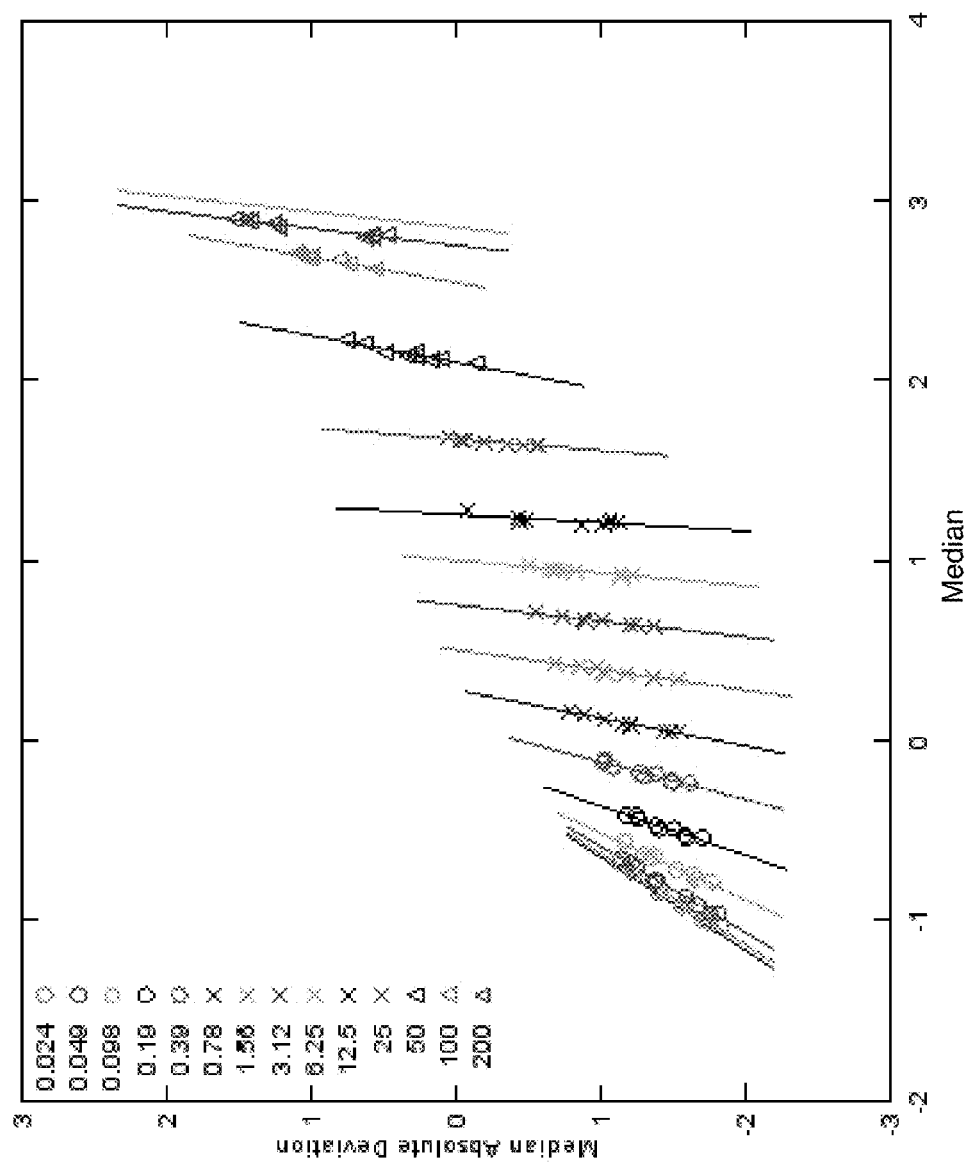
FIG. 15 is an example of a bubble calibration of the present invention collected with a sensor of the design depicted in FIG. 14.

In some embodiments, the mapping is used to generate an estimate of the "bubble-free" reflectance. One such embodiment is described in Example 7. In this embodiment, the calibration consists of a series of lines in MAD-Median space. As shown in FIG. 15, the lines can be extrapolated above and/or below the calibration measurements, in order to accommodate measurements slightly beyond the bounds of the original calibration. The calibration is stored in instrument memory and is applied to new measurements by locating the nearest 2 calibration lines on the map to the new measurement and interpolating between them to create a line on the map that intersects with the new measurement. By tracing the interpolated line down to it's minimum median value, the "bubble-free reflectance" is thereby determined. This minimum median reflectance can be either the minimum of the extrapolated line, or the minimum of the un-extrapolated line. In a preferred embodiment, the minimum of the un-extrapolated line is used. By this method, the effect of bubbles on the reflectance are largely removed, as shown in FIG. 16.

Figure 21:
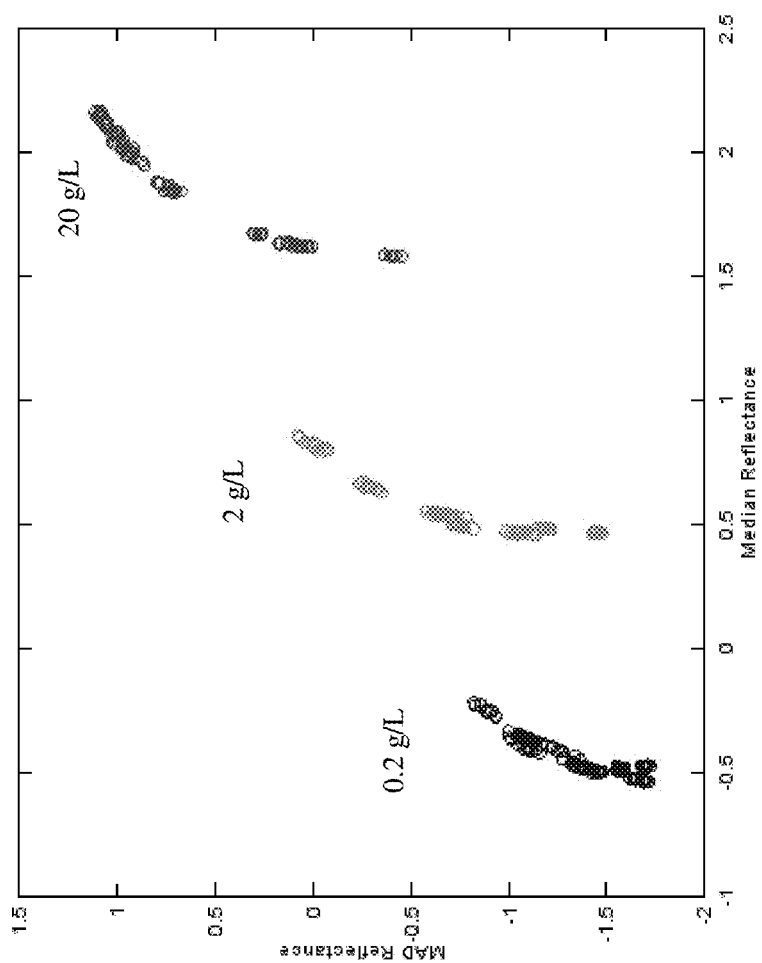
FIG. 21 provides an example of a bubble calibration determined under conditions where variable concentrations of albumin are present in addition to yeast biomass.

In other embodiments, such as described in Example 10 and depicted in FIG. 21, the bubble calibration map is more accurately represented by a series of curves. In this case the bubble-free reflectance is determined by tracing the curve down to the minimum median reflectance, in analogous fashion to the procedure described for linear mapping. In some embodiments the curve is represented by a polynomial function. In yet further embodiments, the bubble calibration consists of a contour map in median-MAD space, and the bubble-free reflectance is determined by interpolating between the contours nearest to the measured median and MAD values, and determining the minimum median reflectance of the resultant contour.

In some embodiments, the concentration in a medium of a first particle type is determined in the presence of a second particle type, with the detection bandwidth and the measurement volume selected so that light reflected from the medium allows signal fluctuations from the second particle type to be resolved, whereas the signal due to the first particle type is substantially constant at a given concentration. By separating the signal fluctuations from the constant signal, the concentration of the first particle type is determined.

In some embodiments the medium is aqueous, and the first particle type is biomass. The second particle type includes gas bubbles. In many applications the gas bubbles are room air, oxygen-enriched air, or a controlled mixture of gases. The medium may be agitated at variable speeds which may also have the result of introducing bubbles into the medium. The number and size of the bubbles suspended in the medium may be affected by the rate of agitation as well as the concentration of other particles suspended in the medium. In other embodiments the second particle type includes un-dissolved media constituents. Of particular interest in the biofuels field, are bio-fermentation processes optimized to break down cellulosic materials. The present invention provides methods for distinguishing the live biomass that is breaking down the material from the material itself.

The effect of air bubbles on measurements of optical reflectance in a liquid biomass culture is described in Example 3. By selecting a close spacing between the source and detector and keeping the source and detector apertures small (S1-D1 or S2-D1 in FIG. 1b), the number of gas bubbles within the measurement volume is kept low enough so that statistical variation is readily observable. At the same time, the biomass (yeast) particles used in this example were much smaller and more numerous than the bubble particles, so that statistical variation due to the biomass particles was low. The increased statistical fluctuations due to the bubbles is demonstrated in FIGS. 4a and 4c, which are measurements at the same biomass concentration (25 g/L yeast) with bubbling off and high, respectively. Power spectra of reflectance amplitude vs frequency (FIGS. 6a-c) show that in order to resolve the variation due to bubbles moving in and out of the measurement volume, a detection of bandwidth of at least about 250 Hz or higher is necessary, in this example. For larger particles, such as media comprised of cellulosic debris, the bandwidth necessary to resolve the particles may be lower, such as 100 Hz. For very large particles, bandwidths as low as 10 Hz may suffice.

The measurement volume necessary to resolve statistical fluctuations due to the second particle type will also vary according to the particle type. Measurement volumes in the range of 1 µL to 1 L may allow bubble fluctuations to be observed. Table 0 summarizes the maximum measurement volumes for the sensor depicted in FIG. 1a. The maximum measurement volumes were estimated from the experimentally measured maximum penetration depths (Example 1). As can be seen in Table 0, the measurement volumes vary strongly according to the source wavelength and the scattering properties of the medium, and more weakly according to the source-detector spacing. The maximum measurement volumes in Table 0 range between 4 µL and 200 mL. Bubble discrimination was found to be more effective when employing source wavelengths at 1310 and 1550 nm than at 980 nm. This is likely due to the smaller measurement volume observed when employing wavelengths that are more strongly absorbed by the medium (e.g. water). When only the 1310 and 1550 nm source wavelengths are considered, the range of maximum measurement volumes is about 4 µL to 20 mL.

TABLE 0

Estimated measurement volumes

| Source Wavelength (nm) | S-D Spacing (mm) | Max. Depth, low scatter (mm) | Max. Depth, high scatter (mm) | Max. Volume, low scatter (mL) | Max. Volume, high scatter (µL) |
|---|---|---|---|---|---|
| 980 | 1 | 75 | 4 | 200 | 30 |
| 980 | 7 | 110 | 6 | 700 | 100 |
| 1310 | 1 | 32 | 3 | 20 | 10 |
| 1310 | 7 | 35 | 5 | 20 | 70 |
| 1550 | 1 | 6 | 2 | 0.1 | 4 |

The measurement volume is most critical when the concentration of the first particle type is low. For example, when the first particle type is biomass, and the biomass concentration is low, the measurement volume can balloon to large volumes, unless a source wavelength is chosen that is strongly absorbed by the medium. As shown in Table 0, with the source wavelength at 980 nm, where water absorbance is relatively weak, the maximum measurement volume is nearly 1 L when the biomass (i.e. scatter) is low. At wavelengths shorter than 980 nm, the measurement volume can easily exceed 1 L. With such a large measurement volume the number of bubbles within the volume can be large enough so that it is difficult to observe fluctuations in the number of bubbles as a function of time. In contrast, more effective bubble discrimination is observed at low biomass, when a strongly absorbing source wavelength is selected. As shown in Table 0, at source wavelength of 1310 nm, the absorbance of the source by water limits the maximum measurement volume to about 20 mL, even when the biomass (i.e. scattering) is low. Yet further restriction in the measurement volume is achieved at 1550 nm, where the measurement volume is limited to about 100 µL. Such a small measurement volume makes it easier to capture fluctuations as bubbles move in and out of the optical field.

In typical embodiments, the light is infrared, the container is a culture flask, the media is aqueous, and the particles are cells. The light source and detector are typically arranged in a sensor housing across a surface and aligned so the light is transmitted in a path describing an acute angle from the direction of detector detection (e.g., optical axis of a conical detection zone for the detector).

Figure 8:
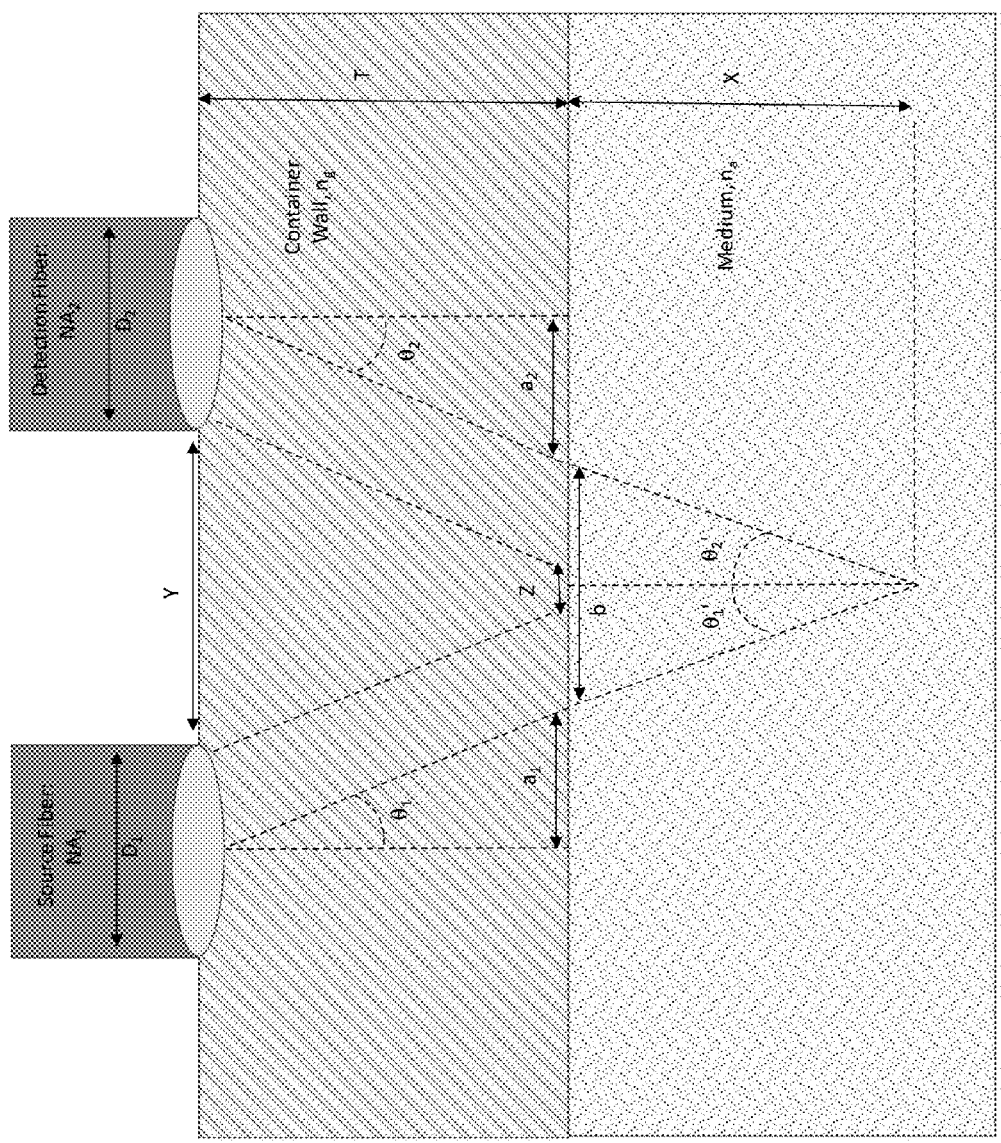
FIG. 8 is a model of the source-detector overlap through a container wall and into a medium for a sensor of the present invention.

In some embodiments the sensor is directly immersed in the medium, such as described in Examples 1-5 and 8. In other embodiments the sensor is positioned outside of the container ("non-invasive"), such as described in Examples 6 and 7. In such embodiments, methods are provided to minimize or eliminate the detection of reflections from the surface of the container itself ("specular reflections"). Such methods include increasing the separation between the source and detector and limiting the numerical and physical aperture of the source and detector. As described above, in many applications it is important to minimize the measurement volume, in order to discriminate against a second particle type, and/or to maximize the range of sensitivity to changes in concentration of a first particle type. In such applications, it is important to balance the need to avoid specular reflections without sacrificing sensor performance. This may be accomplished by configuring the sensor geometry according to the properties of the container. Example 6 describes optimization of sensor geometry according to the thickness of the container wall. Referring to FIG. 8 and Table 6, source-detector overlap through a container wall of thickness, T, was optimized by varying the physical apertures ($D_1$ and $D_2$), numerical apertures ($NA_1$ and $NA_2$), and separation (Y) between the source and detector. Example 7 describes experimental findings for one such sensor, designed for making non-invasive measurements through the 1 mm thick wall of a plastic vessel.

Figure 10A:
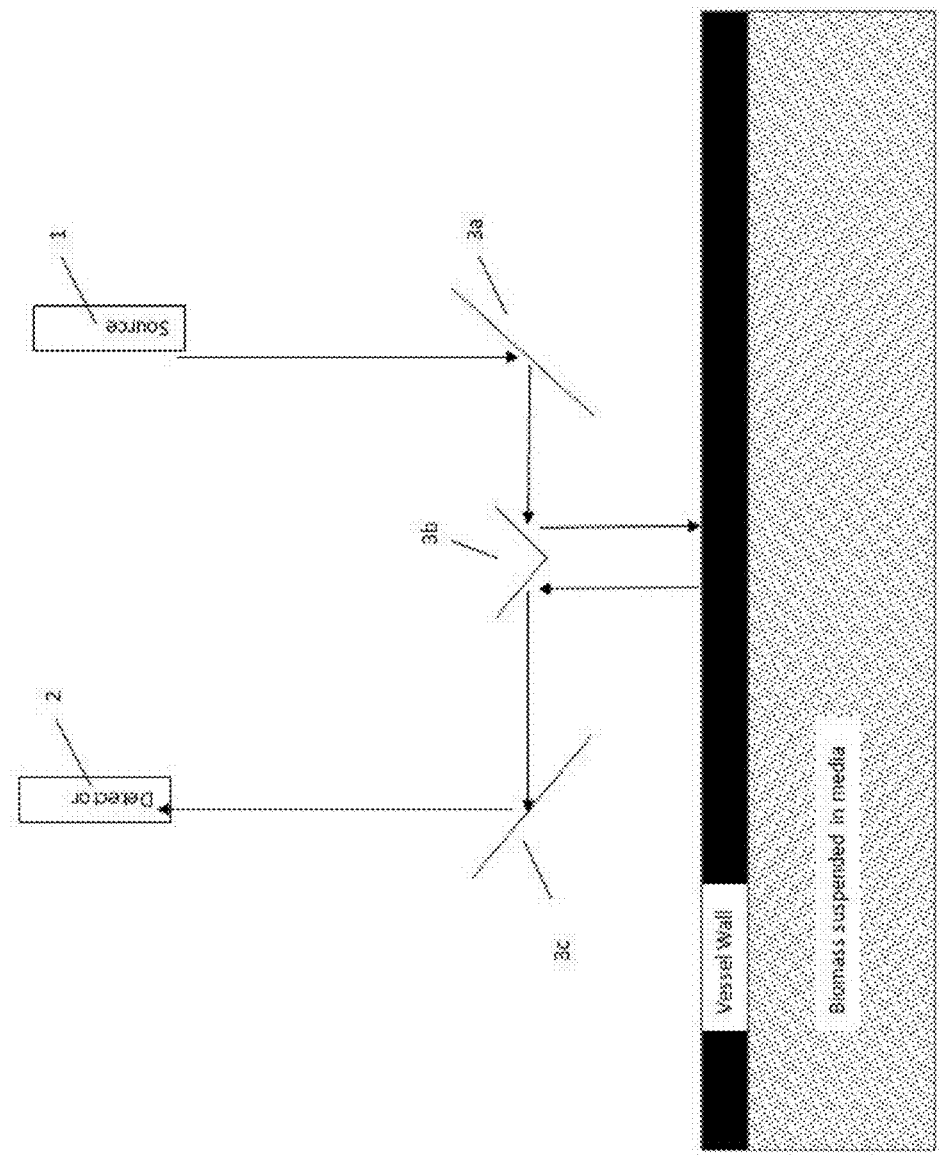
FIG. 10a depicts an embodiment of a free-space optical arrangement of a sensor of the present invention employing one source and one detector.
Figure 10B:
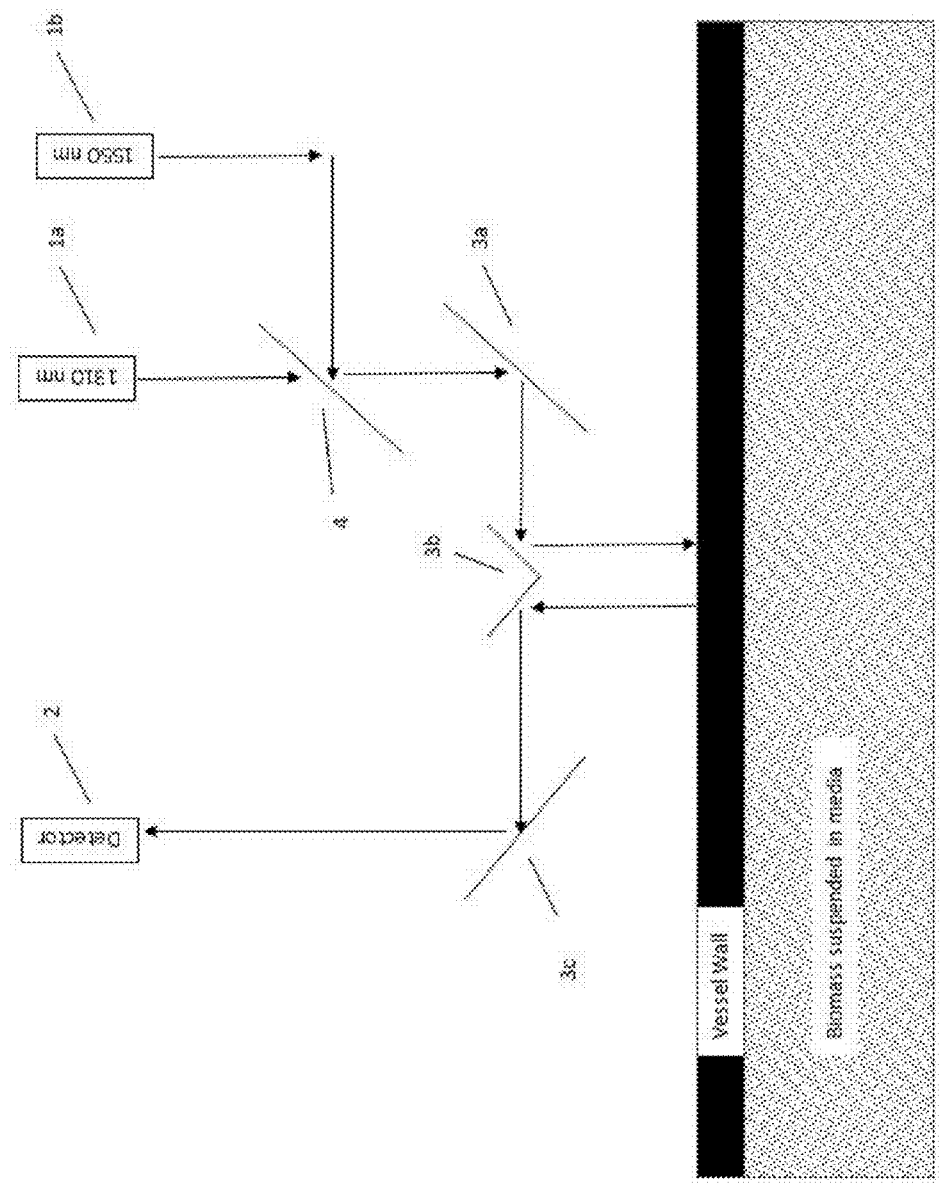
FIG. 10b depicts an embodiment of a free-space optical arrangement of a sensor of the present invention employing two sources and one detector.
Figure 10C:
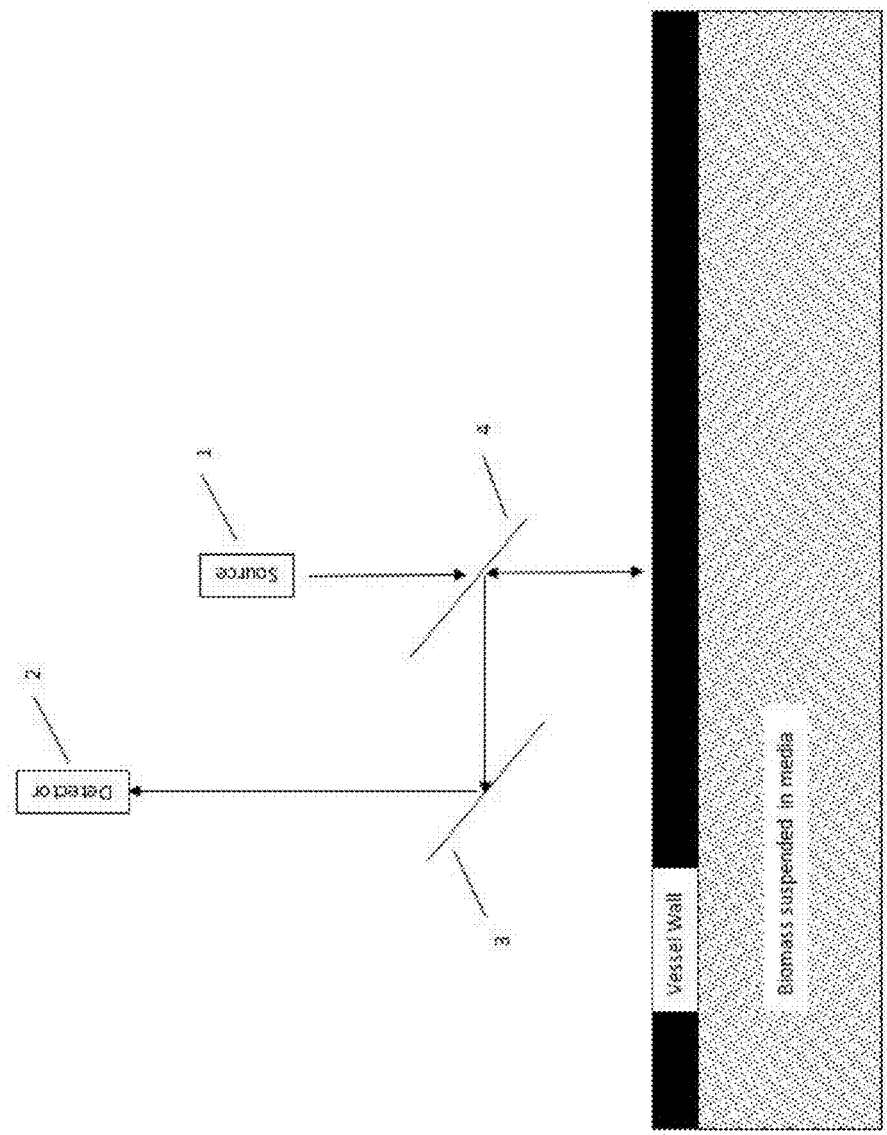
FIG. 10c depicts an embodiment of a free-space optical arrangement of a sensor of the present invention employing one source, one detector, and a polarizing beam splitter.

In other non-invasive embodiments, specular reflections are minimized through the use of crossed polarizers. In one such embodiment, a first linear polarizer is positioned in front of the light source, and a second linear polarizer is positioned in front of the detector. The first and second linear polarizers are oriented so that their polarization axes are substantially perpendicular. In this manner, light undergoing a single reflection (such as specular reflections) will be blocked by the second linear polarizer, whereas light that undergoes multiple reflections and is thereby de-polarized ("diffuse reflections"), will partially pass through the second linear polarizer. In other embodiments, a single polarizing beam splitter is used to accomplish the polarization discrimination. FIG. 10c depicts one such embodiment, in which the source light, 1, passes through the polarizing beam splitter, 4, on its way to the sample. Light reflected back from the vessel wall that retains its original polarization state will pass back through the polarizing beam splitter, 4, avoiding detection. However, light that is depolarized, such as by multiple reflections from particles suspended in the medium, will be partially-reflected by the polarizing beam splitter, 4, allowing it to reach the detector, 2.

The container of media is typically a container designed to hold or store media, but not typically a container normally employed to function with spectroscopic equipment in, e.g., a quantitative analysis. The containers in the present methods are typically, e.g., a shaker flask, a T-flask, a centrifuge tube, a test tube, a roller bottle, a fermentor, a bioreactor, a stir flask, a carboy, a bag, a media bottle, a multiwell plate, a petri dish, a syringe, a pipette and/or the like. In a typical embodiment, the container is not a cuvette (e.g., from a spectrophotometer or fluorometer) and is not a spectroscopic flow cell (e.g., from an assay device).

Where the media is aqueous, the light wavelength is typically an infrared (IR) wavelength. This is because IR wavelengths are well scattered by particles typically of interest and such wavelengths are substantially absorbed by shallow depths of water, with the benefits described above. The light source wavelength in the methods can also depend to some extent on the optical qualities of the container wall in a particular instance. Other useful ranges of light source wavelengths range from less than 650 nm to more than 2000 nm, from about 700 nm to about 1500 nm, from 800 nm to about 1300 nm. In certain embodiments the preferred wavelength is about 1550 nm. In other applications the light sources emits light between 1150 and 1350 nm, between 920 and 1150 nm, between 1350 and 1900 nm or about 1500 nm. In the context of other media, such as organic solvents, other optimum interrogation wavelengths are available, e.g., wherein the particles of interest scatter the light well, and the solvent limits penetration of the light to desired shallow depths.

In some of the methods, it is useful to have the light source and detector on the same side of the container for the analysis. In this way, the scattered light path is not dependent on the container to provide consistent and adequate geometry. That is, a significant benefit of the present methods is that particle detection does not depend on the shape or size of the container holding the media. For example, as long as the media to be tested is in contact with the inside wall of the container at a certain position, the methods allow the reading device to realize an appropriate interaction with the media. The media does not have to be withdrawn or diluted. It matters little what is the shape or size of the container or whether the container is full. In many embodiments, the detector and light source are mounted in a device sensor with their objective aperture in a common plane and directed in substantially the same direction. In preferred embodiments, the light source and detector are arranged so that light emanating from the light source is scattered by particles in the media and returned to the detector describing an angle of from less than 5 degrees to 45 degrees, from 10 degrees to 35, from 15 degrees to 30 degrees or about 25 degrees.

The light source may radiate light in, e.g., a beam or cone, and the detection zone visible to the detector can be described by, e.g., a cylinder or cone. In preferred embodiments, the optical axis of the light source and the optical axis of the detector detection zone are substantially parallel. In other embodiments the axes can converge or diverge from each other at an angle ranging from about 1 degree to 45 degrees, from 3 degrees to 30 degrees, from 5 degrees to 20 degrees or about 10 degrees.

The particles detected in the methods can be any of interest, e.g., in a reasonably uniform suspension. The particles of interest are typically from the fields of materials science or biological sciences. Typical particles of interest in the present methods include, e.g., bacteria, fungi, animal cells, plant cells, polymer particles, nanoparticles, sol gels, proteins, viruses, and the like.

The methods include means of positioning and confirming the position of a light-detector sensor system in relation to the container and media of interest. Uniform and optimal positioning of the sensor can be important to the precision, accuracy, sensitivity and consistency of particle concentration measurements in the methods. Position sensors and alignment guides of the inventive devices are discussed at length below.

The methods include provision of two or more detectors in functional relation to one or more light sources. In the methods, positioning of the sensor, uniformity of the media components, uniformity of the media depth and uniformity of the container wall can be suggested by comparison of signals returned from two or more detectors at different positions. The detectors can be positioned symmetrically or asymmetrically relative to the light source. For example, two symmetrically positioned detectors elements can be positioned to provide a means of determining whether sufficient medium is present in order to make an accurate measurement of particle concentration. Comparison of two symmetrically positioned detectors can also provide a means of identifying nearby interferences. For example, a bubble residing on the sensor may interfere with the optical measurement, but will typically interfere to a different extent with two symmetrically placed detectors. By rejecting measurements for which the detector reflectances are not in agreement, such interference may be avoided. As another example, the reflectance from a nearby object in a bioreactor such as an impeller, sparge tube, baffle, or another sensor may cause interference with the sensor measurement. In some embodiments, disagreement between the reflectance measured by the two or more symmetrically placed detectors leads to an error message being reported to the user that the sensor or probe needs to be repositioned.

Figure 1B:
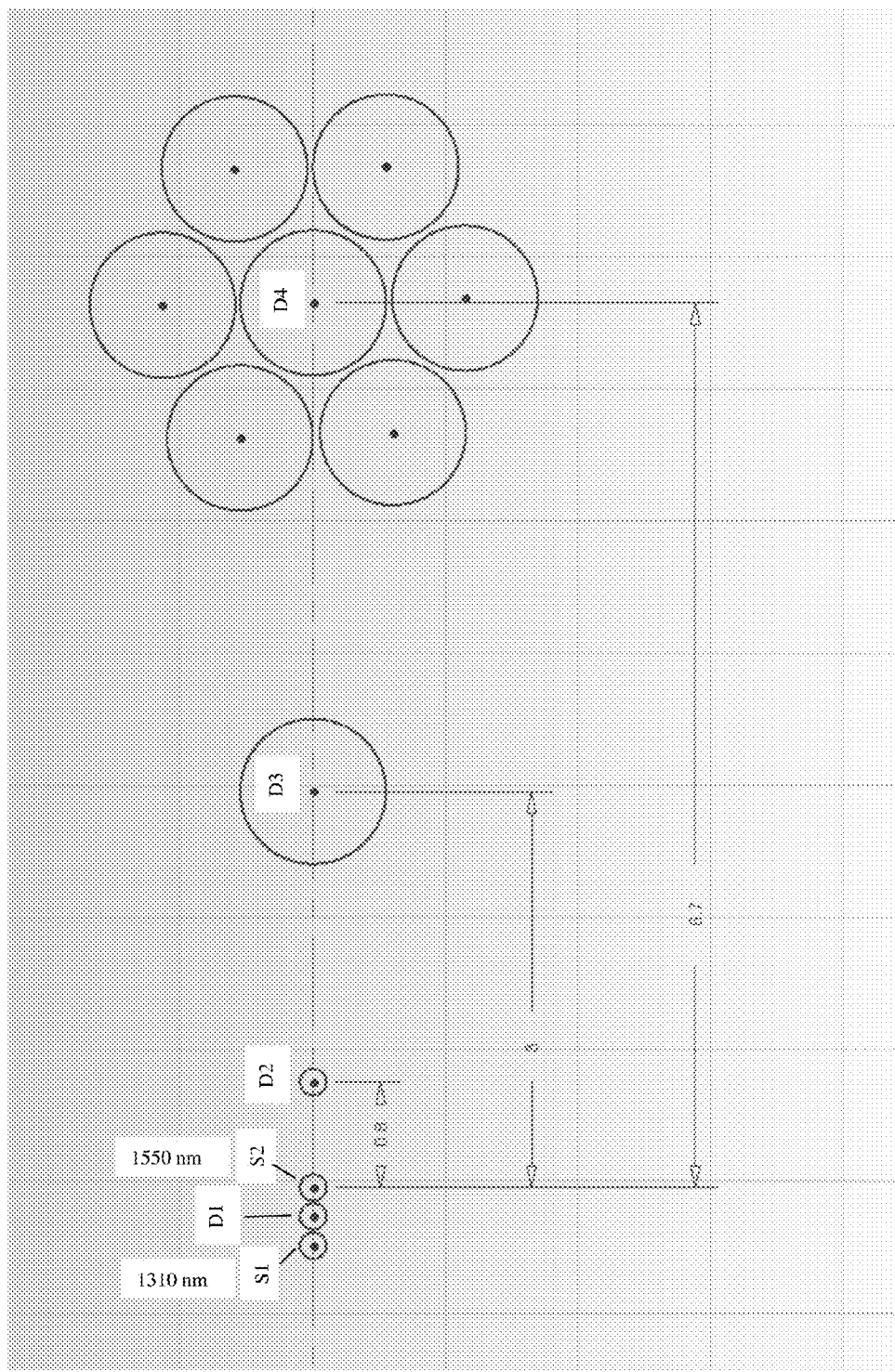
FIG. 1b depicts an end view of the same fiber optic sensor as in FIG. 1a, but with a different configuration of connections to sources and detectors.
Figure 10D:
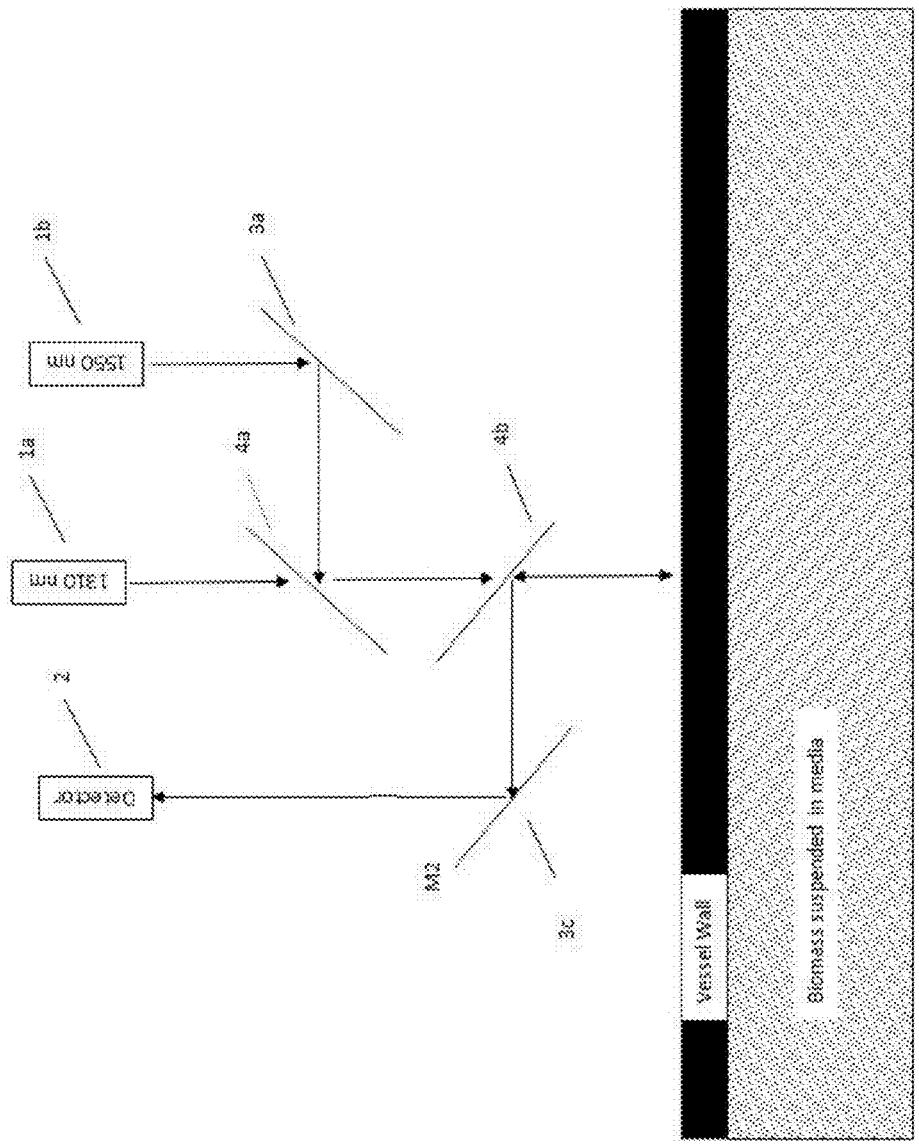
FIG. 10d depicts an embodiment of a free-space optical arrangement of a sensor of the present invention employing two sources, one detector, and a polarizing beam splitter.

In the methods, two or more sources having different emission wavelengths may be combined within the same sensor. Fiber optic embodiments of such sensors are depicted in FIGS. 1a and 1b. Free-space (i.e. non-fiber-optic) embodiments are depicted in FIGS. 10b and 10d. The combining of the multiple source wavelengths may provide the benefit of: (1) extending the measurement range of particle concentrations, (2) improving the discrimination against a second particle type, (3) providing a means of determining whether sufficient medium is present in order to make accurate measurement of particle concentration, and/or (4) allowing particle concentration to be determined over a wider range of medium volumes.

Figure 5F:
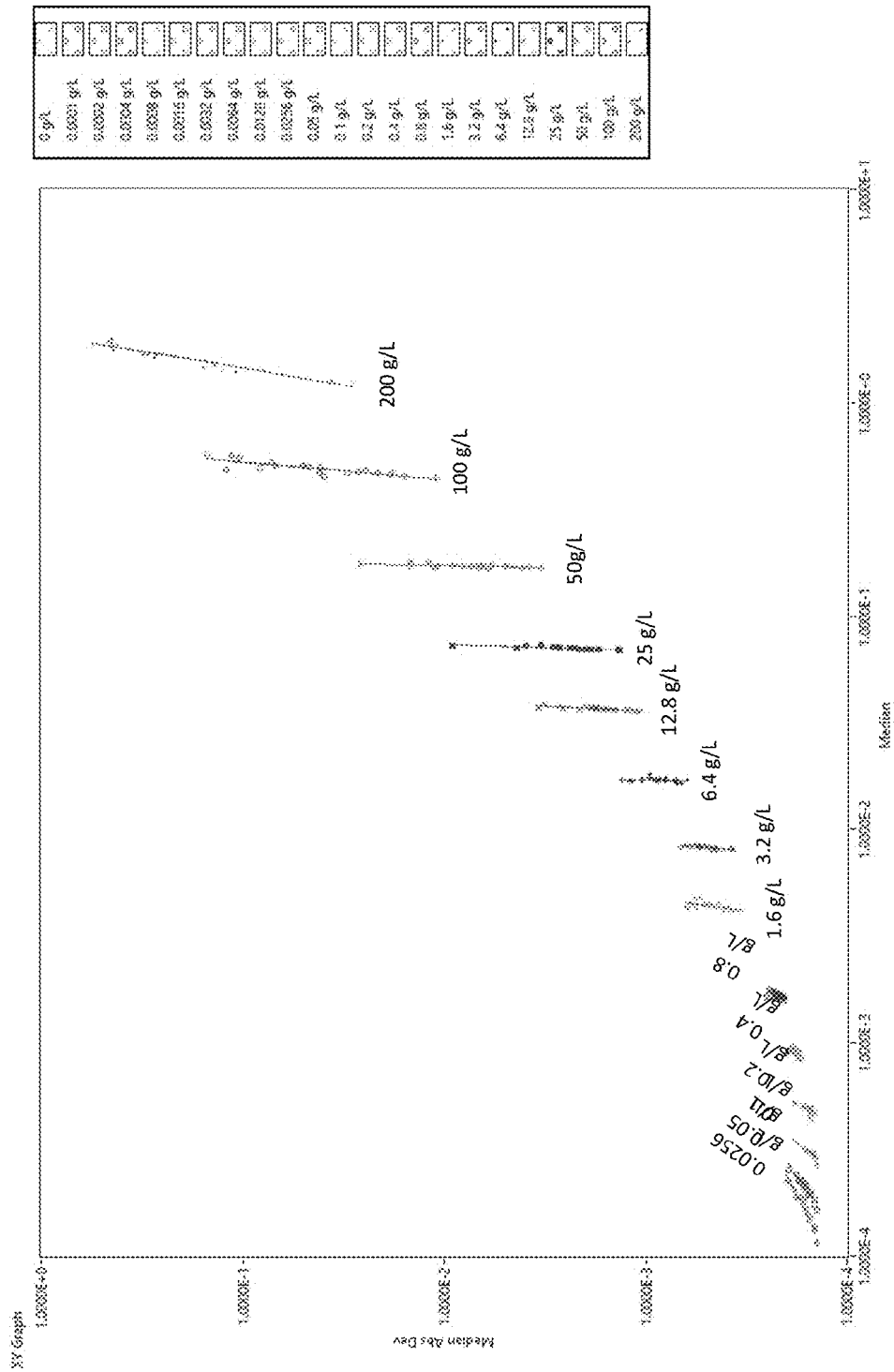
FIG. 5f is a graph of median absolute deviation as a function of median value measured with a sensor of the present invention having a source wavelength of 1550 nm, and a source-detector separation of about 0.22 mm (S2-D1 in FIG. 1b), that was immersed in a 12 L bioreactor containing various concentrations of yeast dissolved in 10 L of 0.9% saline, and agitated and sparged with air over a wide range of settings (400-900 rpm, 0-16 lpm, respectively). Measurements made at the same yeast concentration (but differing sparge and agitation) are represented with markers having the same shape and color.

In some embodiments, the two of more source wavelengths have different mean absorption path lengths in the medium. In one such embodiment, first and second source wavelengths are provided at 1310 and 1550 nm, respectively, and the sensor is used to measure biomass, and bubbles may also be present as a potential interferent to the measurement. Due to the longer mean absorption path length in water, the measurement volume at 1310 nm will be greater than that at 1550 nm. As a result, the measurement sensitivity at low biomass may be better at 1310 nm, whereas at 1550 nm the high range sensitivity linearity may be better (for example, see FIG. 3). For the purpose of bubble discrimination, 1310 nm may provide better data clustering in the low biomass range, whereas 1550 nm may be better in the medium to high range (compare FIGS. 5e and 5f). Measurements made at 1310 nm will have a maximum penetration depth of about 30 mm, whereas at 1550 nm the depth will be limited to about 6 mm (see FIG. 2). Disagreement of two separate biomass concentration measurements based on the 2 source wavelengths, may therefore be indicative of insufficient fluid being present or the presence of an interfering object in front of the sensor. In other applications, the measurement-volume may be selected by the instrument operator, so that the appropriate source wavelength is used for the measurement.

Once scattered light is returned to the detector, the associated signal can be correlated with other useful parameters such as optical density (OD) values or particle concentration. The methods can optionally be used to quantitate the amounts of the particles of interest present in the sample. For example, in one class of embodiments, an intensity of a signal scattered back to the detector is measured and correlated (e.g., through a standard formula determined through regression analysis) with a quantity of the corresponding particles of interest present. The standard formula can then be used to calculate an unknown amount of particles in a sample based on the output signal intensity for that sample. Demonstrations of converting reflectance signal intensity into biomass (dry cell weight) are provided in Examples 7-9.

To increase the precision and accuracy of measurements, the light source can be monitored with a sensor that feeds back to the controller, which instructs compensating changes in radiant flux emitted by the light source, thus stabilizing the light irradiation. An example of laser feedback control is provided in Example 7. Another way to enhance the accuracy of particle concentrations in the methods is to take a blank reading of media without particles and subtracting the blank reading from a measurement of the media containing the particle.

In a particular embodiment, samples can be identified and tracked employing components of the inventive device acting as a bar code scanner. For example, the light source can be a laser and light reflected back to the detector during a sweeping motion across a bar code decal can be detected and interpreted by the processor to identify a sample.

Description of Device Embodiments

The devices of the invention are generally directed to one or more light sources paired with one or more sensors arranged to interrogate a sample of particles in a medium, with the sensor either immersed directly in the medium, or positioned to measure through the walls from one side of a container. For example, the devices for determining the concentration of particles in a medium, can include a housing containing a sensor, a light source in the sensor, a detector in the sensor positioned to detect a signal of source light wavelengths scattered by particles within the medium, and a processor configured to correlate the detected signal to the concentration of particles. Typically the light wavelength emitted by the source is selected to be absorbed without overly extensive penetration into the medium. The device typically comprises a controller configured to measure the detected signals and to control the light sources.

It can be beneficial to make the light source distinctive over background light, and render it complimentary to certain detector circuitry. In a preferred embodiment, the light source of the device is modulated in amplitude and/or frequency. In such a case, accuracy can be enhanced wherein the detector reading frequency is different from the light interrogation frequency, e.g., thus avoiding problematic beat frequencies, and other interference. In preferred embodiments the detector signals measurement rate is at least 4-fold, 10-fold or 100-fold, or more different (preferably greater), than the modulation rate of the light source. In certain embodiments, a quadrature slope correction may be employed as part of a detector demodulation algorithm.

In situations where multiple particulate concentration readings are expected over some time period, it can be useful to affix the light-detector sensor housing to the vessel, thereby providing the capability of making multiple measurements without the need for reapplication of the sensor to the vessel. Typical vessels containing media and subject to particle concentration readings by the devices of the invention include, e.g., shaker flasks, a T-flasks, centrifuge tubes, test tubes, roller bottles, fermentors, bioreactors, stir flasks, carboys, media bags, media bottles, multiwell plates, petri dishes, syringes, pipettes and the like.

The sensors of the devices can have complex arrangements of one or more light sources paired with one or more detectors. For example, signals can be combined from two or more paired source-detectors with two different source-detector separations. The light source or detectors can be fiber optical components, which are optically linked to electro-optical components that are physically separated from the housing, wherein the device further comprises one or more additional detectors in functional relation to the light source. The device can include a second light source with a light wavelength different from the light wavelength of the first light source, e.g., to selectively detect a different particle type or compliment a different container or media. The light source wavelength can be selected according to the separation between the source and the detector, e.g., to tailor the light path length to the expected particle density or media absorbance.

In certain embodiments, the device is configured to provide particular desired characteristics, For example, the device controller can be configured to collect detected signals at least every 0.10 seconds, thereby allowing measurement of variation in the amount of medium or particles in front of the sensor as it varies over time. The processor can be configured to distinguish signals depending on an amount of medium present at the container. The processor can be configured to correlate a ratio of signals collected in the presence of different amounts of media sample to the particle concentration.

In preferred embodiments, the light source and detector are both directed in the same direction. In many embodiments, the source and detector are aligned within 1 degree, 2 degrees, 5 degrees, 10 degrees 20 degrees or 30 degrees of each other.

Sensor Optical Arrangement.

Embodiments of sensors of the present invention are illustrated in FIGS. 1, 8, 10-12, 14, and 18. Referring to FIGS. 11a-d, a sensor housing, 6, holds one or more optical fibers, 5, and provides apertures into and out of the sensor. The numerical aperture of the optical fiber may be selected to limit the divergence of the light source and/or the collection cone of the detectors. In some embodiments (e.g. FIG. 11a), the same optical fiber, 5, is used both to deliver the source light and to collect the light for detection. In some such embodiments a beam splitter may be used to combine and separate the source and detection light. In other such embodiments a fiber splitter (e.g. 2×1 branching) is used to combine and separate the source and detection light.

Figure 11B:
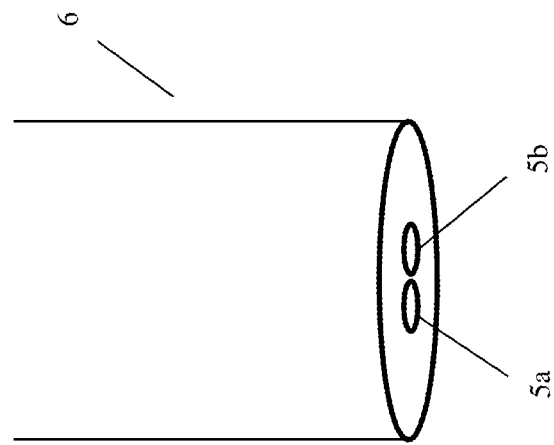
FIG. 11b depicts an embodiment of a sensor of the present invention employing one fiber optic for light delivery and a second fiber optic for light collection.
Figure 11A:
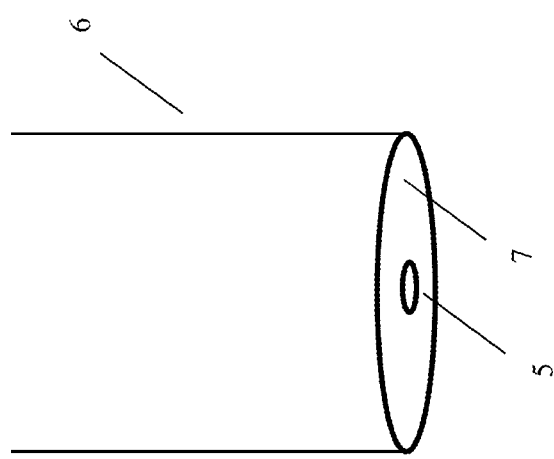
FIG. 11a depicts an embodiment of a sensor of the present invention employing one fiber optic for both light delivery and collection.

In other embodiments (e.g. FIGS. 11b-e) separate optical fibers are used to conduct the illumination (source) and detected light. In the simplest case (e.g. FIG. 11b) one fiber is used to deliver the source light, and a second fiber is used to collect the light for delivery to the detector. In other embodiments, such as depicted in FIGS. 11c through 11e, one fiber is used to the deliver the light, and multiple fibers are used to collect the light for detection. In some such embodiments the detection fibers are delivered to the same detector. The additional fibers used for light collection thereby increase the size of the detected signal, which may be important when the signal magnitude is low, such as at low biomass. In other embodiments, each fiber is coupled to a separate detector. The use of detection at multiple distances from the source fiber, may allow the range of biomass to be extended. Alternatively, the detector fibers may be symmetrically located around the source fiber. By comparing the results from the multiple detectors, the presence of interfering objects, or the absence of sufficient fluid in front of the sensor may be determined. In this manner, the use of multiple symmetrically-located and separately-detected fibers may allow for improved measurement accuracy and/or rejection of inaccurate results.

The fiber optic embodiment depicted in FIG. 11e offers the benefit of easy and reproducible manufacture. A single hole may be made with a diameter just sufficient to accommodate the three fibers in a close-packed triangular arrangement. During assembly the fibers are forced into an equilateral triangular arrangement by the constraint imposed by the hole diameter. The separation between the source and detector fibers may be adjusted by selecting fibers having different cladding diameters, or by leaving the fiber buffer layer in place, so that it determines the close-packed diameter. In one particular embodiment, three fibers with 200/220/239 mm core/cladding/buffer diameters (such as Polymicro part number FIP200220240) are used. The fiber buffer is left in place during assembly, and the radius of the hole made to accommodate the three fibers has a radius of approximately 520 μm.

In other sensor embodiments, provision of the light source and detection are accomplished without the use of optical fibers. As with the fiber-optic based embodiments, such free-space embodiments may be used either non-invasively (i.e. measuring through the wall of the vessel), or invasively (i.e. immersed in the medium). Several free-space embodiments are depicted in FIGS. 10a-d. In FIG. 10a, the source and detector are directed to and from the measurement medium through the use of mirrors, 3a-c. The use of a two-sided right-angle mirror (e.g. 3b in FIG. 10a), allows the source and detector light to enter and the exit the medium as collinear beams with minimal separation. The embodiment depicted in FIG. 10b, further includes a dichroic beam splitter, 4, for combining the two light sources, 1a and 1b, into a single beam, with high efficiency.

The free-space embodiment depicted in FIG. 10c employs a beam splitter, 4, to combine the source and detection beams. The advantage of this arrangement is that the source and detection beams can be overlapped to the extent desired. Further, by using a polarizing beam splitter, the detection of specular reflections from the vessel wall may be minimized, in applications where the sensor is used for non-invasive measurements. The embodiment depicted in FIG. 10d is an extension of that depicted in FIG. 10c, to include a second overlapped source wavelength.

In many embodiments of the invention, a laser monitoring detector provides a signal for measuring and/or controlling the laser radiant flux. The laser is directed into the medium either directly, or through a wall or aperture ("window") of a vessel into a medium. The vessel window should be at least partially transparent to light at the laser wavelength. Suitable vessels include flasks, bottles, tubes, fermentors, and bioreactors with window material made from such optically transparent materials as plastic (e.g. polyethylene terephthalate (PET), polycarbonate (PC)), or glass. The preferred embodiment described here is especially well-suited for thin-walled (<6 mm thick) vessels, such as is typically found in laboratory shake flasks, roller bottles, and tubes.

After the source light has penetrated the vessel window, cells or microorganisms within the medium scatter the light, some of which is reflected back towards the sensor. Reflected light is detected by at least one reflectance detector. In some embodiments, the optical fibers are close-packed, so that the source-detector separation is determined by the diameter of the cladding, or if the buffer is left intact, by the diameter of the buffer. In Example 8, described below, both the source and detection fiber have a core and cladding diameter of 0.2 and 0.22 mm, respectively, and a numerical aperture of 0.22. The fibers are close-packed, with the center-to-center distance between the laser and each detector approximately 0.22 mm, as determined by the fiber diameter (with cladding).

In the embodiments depicted in FIGS. 11c to 11e, additional detection fibers are provided. In one particular embodiment, the center-to-center distance between the source and each detector fiber is approximately 0.22 mm and the numerical aperture of the fibers is 0.22. The numerical aperture of the fiber limits the full angle of the emission and detection cones to about 25 degrees in air, or about 19 degrees in water. Many other combinations of fiber diameters and numerical apertures could be used, depending on the desired measurement volume. For example, by selecting fiber with numerical aperture of 0.11, the angle of the detection and emission cones would be reduced to about 9 degrees in water, thereby substantially reducing the measurement volume. In other embodiments the close-packing diameter is determined by the fiber buffer diameter. For example, in alternate version of the immersible probe described in Example 8, the buffer is left in place during manufacture of the probe, thereby increasing the source-detector separation while still having the simplicity of a close-packed arrangement. For example, with a buffer diameter of 0.239 mm, the source detector separation will be increased to 0.239 mm from 0.22 mm, by keeping the buffer intact. One potential advantage of this increase in source-detector separation, is that sensitivity to dirt or fouling at the sensor tip may be reduced.

In addition to being scattered by the contents of the medium, the laser wavelength is chosen so that it is partially absorbed by the medium itself. Water, being the principle constituent of all cell media and relatively invariant in concentration, is an ideal candidate for providing this partial absorption of the light source. The absorption by the medium needs to be low enough so that the light has a chance to scatter from cells in the medium and return to the detectors before being absorbed. On the other hand, the absorption needs to be high enough so that light scattered from the cells and then reflected by the vessel wall, objects external to the vessel, or non-cellular objects within the vessel, has a low probability of returning to a location within the vessel from which it can enter the detector apertures before being absorbed by the medium.

The mean absorption path length of the medium at the source wavelength will determine the maximum distance between the source and reflectance detectors at which the reflectance signal will be detectable. In most applications, the source-detector separation should be kept less than a factor of about ten times the mean absorption path length in order to be detectable. In many applications, in order for the signal to be optimally detected (e.g. with high signal to noise ratio), the factor should be kept less than about 5, less than about 2, or in many applications less than about 1. For example, with a source wavelength of 1310 nm, the mean absorption path length in water is about 6 mm. At source-detector separations of greater than about 60 mm, the signal will be difficult to detect, and for optimal detection, the source-detector separation should be less than about 30 mm, less than about 12 mm, or for many applications less than about 6 mm. As another example, at a source wavelength of 1550 nm, the mean absorption path length in water is 0.8 mm. Signals at 1550 nm become difficult to detect at source-detector separations greater than about 8 mm, and the source-detector separation is optimally kept below 4 mm, about 1.6 mm, or in many applications, less than about 0.8 mm.

In addition to considerations of signal detection, the effect of the source-detector separation on the range of sensitivity to particle concentration changes should also be considered in many applications of the present invention. The selection of one or more source-detector separations optimized for measurement of particle concentrations in particular concentration ranges has been described in prior art (e.g. U.S. Pat. No. 8,603,772). The unexpected finding of the present invention is that by selecting the source-detector separation to be substantially less than the mean absorption path length in the medium, the range of sensitivity to particle concentration can be greatly extended. In many applications requiring a wide range of sensitivity to particle concentration, the source-detector separation should be kept less than the mean absorption path length, by a factor of about one half (½), a factor of about one fourth (¼), or a factor of about one tenth (¹⁄₁₀) times. For example, referring to FIG. 3 and Example 2, at a source wavelength of 1550 nm, with a source-detector separation that is approximately equal to the mean absorption path length (0.8 mm), the experimentally observed (red squares in FIG. 3) range of sensitivity to changes in biomass is about two orders of magnitude (from about 1 to 100 g/L yeast concentration). But by decreasing the source-detector separation to about 0.2 mm, or about a factor of one fourth (¼) times the mean absorbance path length, the range of sensitivity to changes in biomass is extended to about four orders of magnitude (from about 0.02 to 200 g/L yeast concentration). A similar pattern is observed with the source wavelength set to 1310 nm. Again referring to Example 2 and FIG. 3, with the source-detector separation chosen to approximately match the mean absorption path length (about 6 mm), the range of sensitivity to biomass change is limited to about two orders of magnitude (from about 0.1 to 10 g/L yeast dry cell weight, data not shown). As the source-detector separation is decreased to about a factor of ½ (3.2 mm), about a factor of ⅕ (1.2 mm), and about a factor of about ¹⁄₃₀ (0.2 mm) times the mean absorption path length, the range of sensitivity to biomass change increases to about 3 (0.05 to 50 g/L), about 4 (0.01 to 100 g/L), and more than 6 (about 0.0001 to 200 g/L) orders of magnitude, respectively.

Optimizing Sensor Geometry According to Vessel Wall (Window) Thickness

For applications in which the source and detected light must travel through a window on the way to and from the medium (e.g. non-invasive measurements through a vessel wall), the impact of the sensor geometry on sensitivity to window back-reflections may also need to be considered. If the source emission cone overlaps with the detection cone within the window, there is a potential for interference of light reflected from the inner wall of the window ("specular reflection"), with the desired light emanating from reflections off of particles within the medium ("diffuse reflection"). In general, increasing the source-detector separation and decreasing the emission and detection cone angles will lead to decreased interference due to specular reflections. However, since the range of sensitivity to changes in particle concentration generally decreases with increasing source-detector separation (as described above), the selection of the optimal source-detector geometry may require a careful balance. In many embodiments of the invention, the minimum source-detector separation that still avoids significant interference from specular reflection is selected. Besides the source-detector separation, other factors that may be varied to minimize the effect of specular reflections include: (1) the source and detection diameters, (2) the source and detection numerical apertures, (3) the central angle of incidence of the source and detector beams relative to the window surface, and (4) the relative polarization of the source and detected beams.

Example 6 (below) describes the optimization of the sensor geometry based on 2 of these factors, fiber diameter and numerical aperture, in a sensor consisting of a single source and detection fiber, such as depicted in FIG. 8, that is interfaced to a vessel having wall thickness, T. Configuration 1 in Table 6 corresponds to the case where the window thickness, T, is zero: the sensor is directly immersed in the medium. This configuration was experimentally tested, as described in Examples 1-5. In order to predict how these results could be extended to non-invasive measurements, where the wall thickness (T) is greater than zero, a simple geometrical model was developed which predicts the effect of source and detector diameter ($D_1$ and $D_2$), numerical aperture ($NA_1$ and $NA_2$), and edge-to-edge separation (Y), on the depth of optical overlap within the medium (X), and the closest point of intersection (Z) within the container wall. In configurations 2-16, several different wall thickness are considered. The same optical overlap depth as in case 1, is maintained by varying the source and detector diameters, numerical apertures, and edge-to-edge separations. By also maintaining Z as a positive number, sensitivity to specular reflections may be minimized.

In configuration 3 (Table 6), having window thickness 2.1 mm, the same optical fiber diameters and numerical apertures are used as in configuration 1, but the edge-to-edge separation between the fibers is increased from 0.04 to 0.66 mm, in order to maintain the same optical overlap depth (X=0.71 mm). The model predicts that this can be done while still substantially avoiding specular reflections (Z>0). Since this optical model neglects the effects of scattering and multiple reflections within the window, in some applications it may prove beneficial to further separate the overlap of the source and detector beams within the window. This could be accomplished by decreasing the diameter and/or numerical aperture of the source and/or detector fibers. Configuration 2 describes the case where the diameter of both the source and detector fibers is decreased from 0.2 to 0.1 mm. By slightly increasing the edge-to-edge separation between the fibers (Y=0.76 mm) compared to configuration 2, the same optical overlap depth is maintained (X=0.71 mm), but the separation between the source and detector beams within the window is increased (from 0.04 to 0.14 mm). The effect of increasing the diameter of the source and detector fibers is shown in configurations 4 and 5 in Table 6. By doubling (configuration 4) or tripling (configuration 5) the fiber diameters, while still maintaining the same optical overlap depth (X=0.71 mm), the source and detector beams will overlap within the container wall (Z<0), so that specular reflections may interfere with the desired measurement of diffuse reflections emanating from the medium.

In many applications it may be beneficial to use different diameters and/or numerical apertures for the source and detector. For example, when the source is a laser which can be coupled with high efficiency into a small diameter fiber with low numerical aperture, using a larger diameter and/or numerical aperture for the detection fiber may provide the benefit of increased light collection, while still minimizing sensitivity to specular reflections. Examples are provided by configurations 6-10 in Table 6, where the diameter of the source fiber (0.1 mm) is chosen to be half that of the detection fiber (0.2 mm), and several different numerical apertures (0.22-0.48) are compared. Compared to configurations 2 and 3, where the same source and detector diameters and numerical apertures are employed, configurations 7-10 are predicted to offer the benefit of reduced sensitivity to specular reflections (higher values of Z). Configurations 11-16 provide examples of optimizing the sensor geometry for several other window thicknesses.

Experimental results for a specific sensor embodiment designed for making non-invasive biomass measurements through a 1 mm thick plastic vessel wall are described in Example 7. This sensor employs a single-mode (approximately 0.01 mm core) fiber for the source light at 1330 nm and a 0.2 mm core multi-mode fiber for detection. The source-detector separation of 0.7 mm (center to center) provides sufficient discrimination against specular reflection from the vessel wall while still enabling linear biomass detection over more than 3 orders of magnitude (see FIG. 17). Use of a single mode fiber for the source provides high transmission efficiency of the 1330 nm laser diode, while allowing a low-cost fiber splitter to be used to deliver the light to multiple sensors simultaneously.

In addition to source and detector diameter, numerical aperture, and separation, the angle of the central optical axes of the source and detection beams relative to the vessel window may also be adjusted to help reduce the influence of specular reflections on the measured signal. In some embodiments of the invention, the face of the sensor (e.g. component 7 in FIG. 11*a*) is positioned so that it is not parallel to the surface of the window through which the measurement is made. The extent of tilt may be selected according to the numerical aperture and/or separation of the source and/or detectors, and/or the window thickness. A tilt angle of at least the half-angle determined by the numerical aperture, may substantially reduce the effect of specular reflections. In other applications with greater sensitivity to specular reflections, tilt angles of at least twice, at least 3 times, or least five times the half-angle of the numerical aperture are selected. For the embodiment depicted in FIG. 11*a*, if an optical fiber having a numerical aperture 0.22 is selected, and the window material has an index of refraction of 1.5, the half-angle of the numerical aperture will be about 8 degrees. In this case, selecting a tilt angle of the sensor face, 7, relative to the surface of the window of at least 8 degrees will substantially reduce the influence of specular reflections on the measurement. Further increases in the tilt angle to at least 16 degrees, at least 24 degrees, or at least 40 degrees, may further enable the rejection of specular reflections in many applications.

In other embodiments of the invention, tilting of the optical axes of the source and detector are achieved by tilting the components themselves, or by tilting the optical fiber through which the light is transmitted, rather than simply tilting the surface of the sensor relative to the window surface. In such embodiments, the source and detector optical axes may be tilted independently, to further optimize the rejection of specular reflections in favor of diffuse reflections emanating from the medium.

Sensor Housing

For applications in which the sensor is directly immersed in the medium to be measured, the composition of the sensor housing may be chosen so as to minimize interaction with the medium or the particles suspended in the medium. In some embodiments, the sensor housing may be constructed from stainless steel, for example stainless steel type 316 L may be suitable for applications. The surface of the housing may also be polished in order to minimize the potential for interactions with the medium. For example, a surface polish specification of N5 (<0.4 µm), may be suitable when the medium contains biomass. In other applications, the sensor housing may be constructed from glass.

Figure 12C:
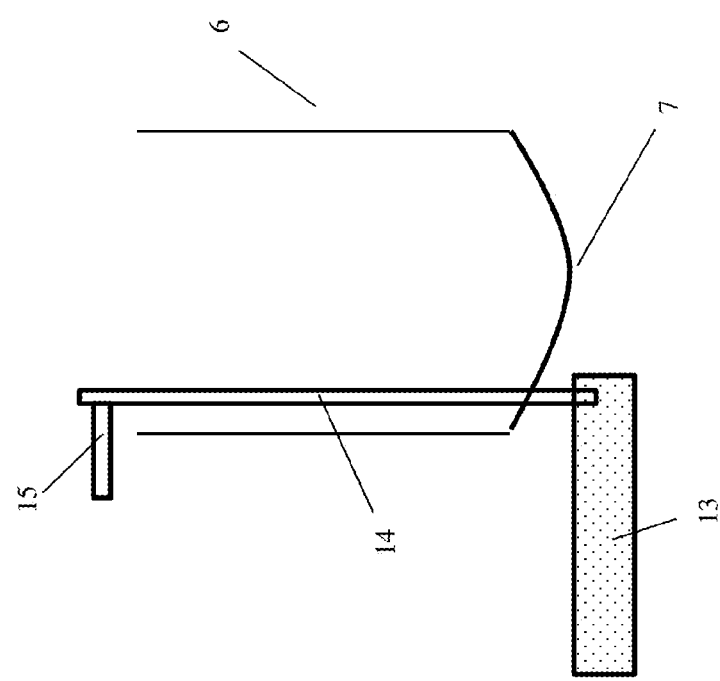
FIG. 12c is a side view of an embodiment of a sensor of the present invention which includes a rounded surface on the sensor face and a scattering reference material held in the open position.
Figure 18:
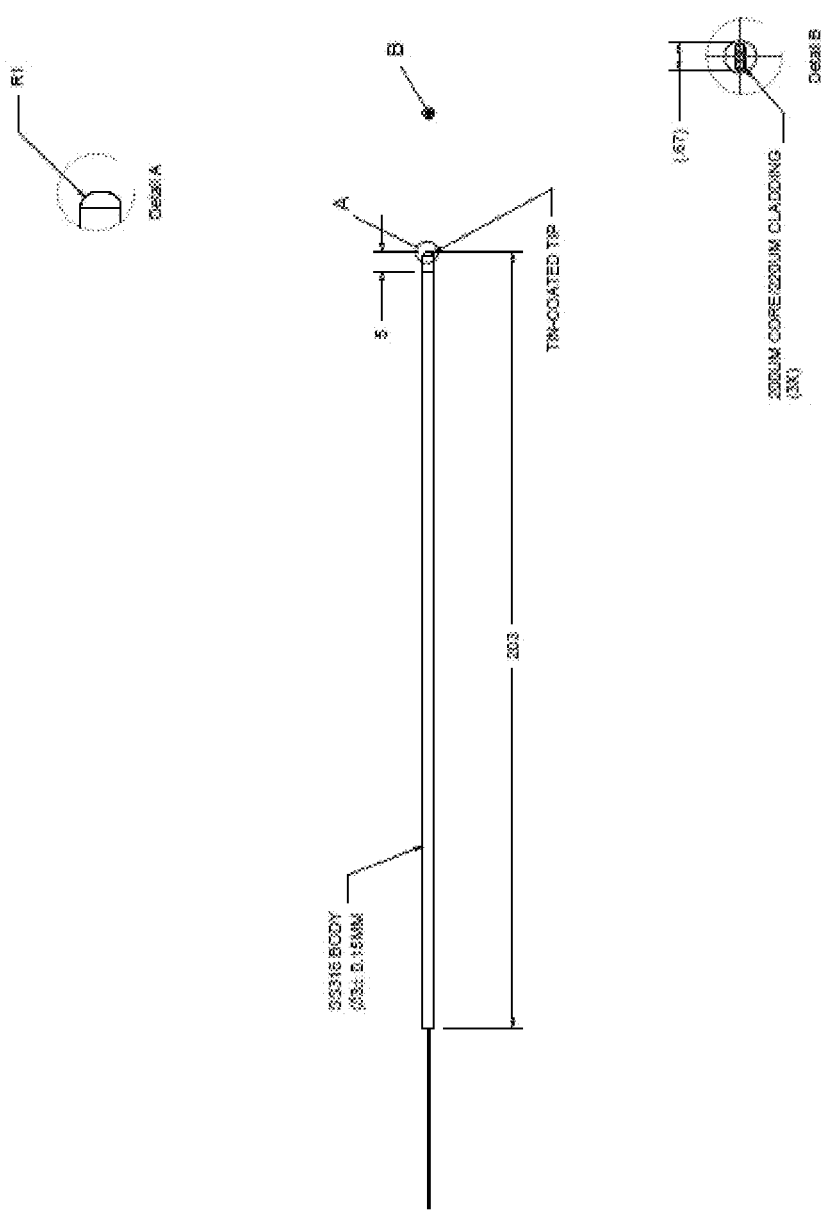
FIG. 18 depicts an embodiment of a probe of the present invention designed for immersion into small bioreactor vessels.

The adhesion of materials on or near the optical face of the sensor is minimized or eliminated in some embodiments of the present invention through the selection of particular sensor face materials, the surface polish and coating of the materials, and/or the shape of the materials. In one embodiment, the tip of the sensor is coated with titanium or zirconium nitride. The effect of such a coating may be to reduce or prevent adhesion of gas bubbles and/or biological material such as cells or protein, to the surface of the sensor. Reduced bubble adhesion to titanium nitride coated stainless steel compared to uncoated stainless steel is demonstrated below in Example 12. Zirconium nitride is known to have similar properties to titanium nitride but has the benefit that it can be applied (e.g. by vapor deposition) at lower temperatures (e.g. at 200 C instead of 300 C) compared to titanium nitride. In other embodiments the tip of the sensor is constructed from glass. In yet other embodiments, such as depicted in FIGS. 12*b*, 12*c*, and 18, the surface of the sensor is rounded. The rounding of the surface, may further aid in the reduction of adherent particles.

The front face of the sensor may be covered with a face plate that protects the sensor from the environment in which it is operated. The face plate should be constructed from a material that is transmissive to light emitted by the laser. In addition, the face plate may be absorptive to light at wavelengths other than the laser emission wavelength. An example of a suitable material for the face plate is Edmund Optic part number NT 43-954, which is transmissive to near infrared light but absorptive to visible light. In some embodiments a gasket is used to prevent the sensor from sliding easily against the vessel surface. When pressed against a vessel wall, the gasket may also be used to create a seal that prevents materials from occluding or affecting the optical measurement. In some embodiments, surrounding the face plate is a gasket groove used to contain the gasket. The gasket groove helps to prevent the gasket from moving and possibly obstructing the face plate.

Verification, Correction, and Calibration of Sensor Performance

In some embodiments of the invention, a material with a stable reflectance is provided for the purpose of checking, and if necessary correcting, the sensor performance. Examples of suitable materials for this purpose are Kynar and Teflon. The expected reading may be stored in instrument memory or written on the standard itself. If the actual sensor reading does not agree with the expected reading, in one embodiment correction factors are applied to the reflectance measurement to bring it back into agreement. These correction factors may then be stored and applied to subsequent readings.

For sensor embodiments designed to be immersed in a medium, it may be desirable, in some applications, to be able to perform the sensor verification and/or calibration step while the sensor is immersed in the medium. For example, when the sensor is immersed in a medium for growth of biomass that has been sterilized to prevent growth of undesired organisms, the sensor may need to be sterilized along with the vessel, precluding its subsequent removal, without jeopardizing the culture to contamination. Sensor embodiments designed to allow the calibration/verification step to occur without the need to remove the sensor from the medium, are depicted in FIGS. 12a through 12c. The scattering reference material, 13, is attached to the sensor using a support shaft, 14, that traverses the interior of the sensor housing, 6. A turning handle, 15, attached to the support shaft allows the user to rotate the reference material into and out of the optical path of the sensor. FIGS. 12a and 12b depict embodiments with flat and rounded sensor faces, 7, with the scattering reference material positioned for a verification/calibration measurement. FIG. 12c depicts the same embodiment as 12b, but with the scattering reference material rotated out of the optical path, so that scattering can be measured from particles in the medium in which the sensor is immersed.

The sensor embodiments depicted in FIGS. 12a-c may have the added benefit of providing a mechanism by which interfering material may be cleared from the front of the sensor face. For example, the accumulation of cells, cell debris, or proteins on the sensor window may interfere with the measurement of the particles suspended in the medium. In such cases, the scattering reference material may function as a wiper, so that one or more passes of the scattering material across the face of the sensor, may serve to clean it. As another example, in cases where bubbles have a tendency to adhere to the face of the sensor, with the potential to interfere with the diffuse scattering measurement, the scattering reference may be used to remove the bubbles from the sensor face.

Storage of Sensor Calibration Coefficients and Sensor Connector

In many embodiments it will be convenient to store coefficient values related to the sensor calibration or settings in the sensor itself. In one embodiment, the sensor is an immersible sensor employing fiber optics to transmit light between a base unit which contains the electro-optical components (e.g. light sources and detectors) and the point of measurement in a medium. In order to allow the sensor to be sterilized within the measurement vessel it will convenient in many cases to be able to disconnect the sensor from the base unit. A memory device, such as a 1-wire EEPROM, provides a convenient means for storing sensor calibration coefficients and settings. The memory device may be located within the sensor housing, or within the connector on the sensor. In one embodiment the connector is a hybrid electro-optical connector that provides a mechanism for simultaneously connecting the fiber optic and electrical (e.g. memory device) components, within a single connector. Such connectors are commercially available (e.g. F7 connectors made by Lemo: http://intra.lemo.ch/catalog//ROW/UK_English/f7_contacts.pdf).

Data Acquisition Timing

Figure 9:
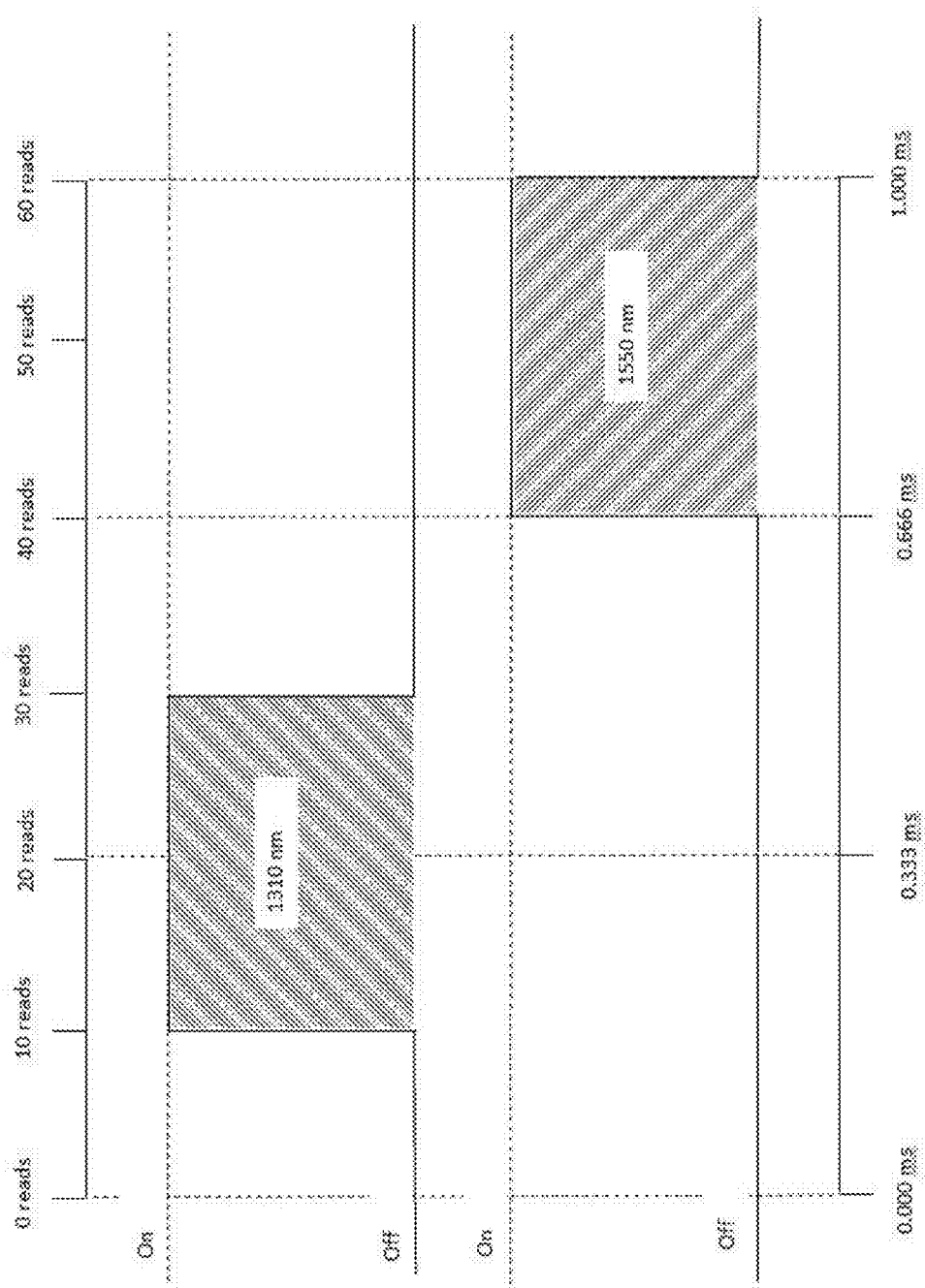
FIG. 9 is an example of a timing scheme for laser driving and detector reading for a device of the present invention.

A timing scheme for driving 2 lasers and reading one or more detectors in a sensor of the present invention, is depicted in FIG. 9. The 2 laser sources are each driven at 1 KHz with a square wave pulse having 25% duty cycle. The relative phase of the lasers is fixed so that the "on" period of the 2 laser pulses are separated by about $\frac{1}{6}^{th}$ of a millisecond, to avoid any potential interference. The one or more detectors are each read continuously at a rate of about 60 kHz, that is synchronized with the laser drive pulses. Dark periods (where both lasers are turned off) are used to measure contaminating light levels (e.g. ambient light), which can then be subtracted from the signals measured while the lasers are on, if necessary.

Test Tube Reader

Figure 13A:
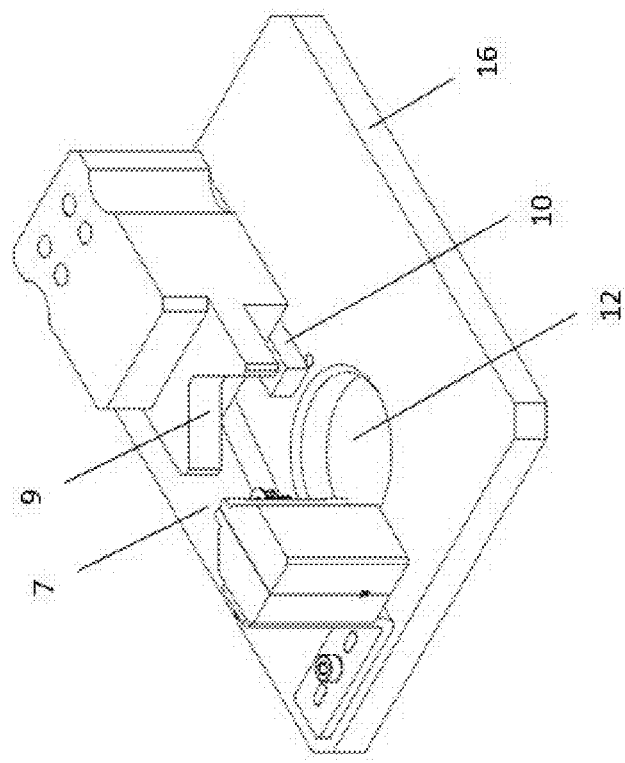
FIG. 13a is an isometric view of an embodiment of a sensor of the present invention designed for measurements through the wall of a test tube.
Figure 13B:
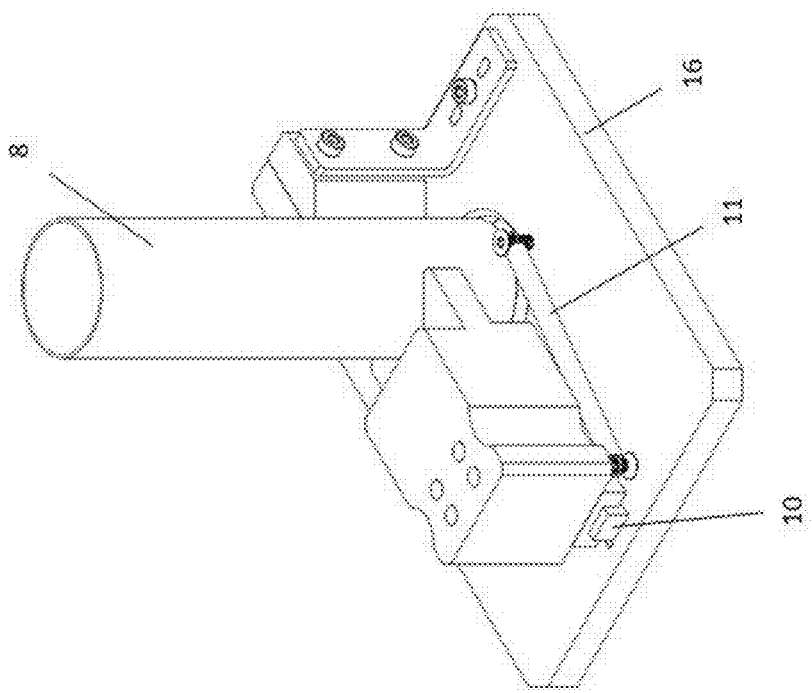
FIG. 13b is a second isometric view of an embodiment of a sensor of the present invention designed for measurements through the wall of a test tube (the test tube is removed in this view).

An embodiment of the invention, designed for measuring particle concentration in test tubes or other small vessels is depicted in FIGS. 13a through 13c. The test tube, 8, is held in place on one side by a rear support, 9, that has a V or U-shape in one dimension and is substantially flat in a second dimension, so that it can stably accommodate test tubes having a range of diameters. The rear support is held on a sliding rail, 10, that travels in a direction perpendicular to the tangent of the test tube surface that is closest to the center of the V or U shape in the rear support. The rear support is urged against the wall of the test tube by a spring, 11, that links the rear support and the base, 16, of the test tube reader. The side of the test tube opposite the rear support interfaces with the sensor face, 7, where the optical measurement is performed. In a preferred embodiment of the invention, the sensor face includes a light source emitting at approximately 1550 nm, and two symmetrically-placed detectors. The laser and detectors are positioned along a line that is parallel with the flat surface of the test tube. The detectors are equally spaced from the light source, with the center-to-center source-detector spacing between about 0.1 and 3 mm, for example about 0.8 mm. In many applications it will be convenient to use fiber optics to convey the light between the optical elements (e.g. laser and detectors) and the sensor face. In many embodiments, an aperture, 12, is provided in which the end of the test tube may be placed.

The choice of source wavelength will in part determine the minimum tube diameter on which accurate measurements of particle concentration may be made. In the embodiment described above using a 1550 nm source, the minimum tube diameter will be about 6 mm, for measurements at low particle concentration (smaller tubes could be measured at higher concentration). Selection of a source wavelength having a higher absorbance than 1550 nm in the medium will allow accurate measurement in tube diameters smaller than 6 mm. In some embodiments a stop is provided on the rail, which limits the motion of the rear support so that test tubes having a diameter smaller than a chosen value will not be accommodated by the holder. For example, if the source wavelength is 1550 nm, the stop may be positioned so that tubes having a diameter smaller than about 6 mm will not be held securely between the sensor face and the rear support. In yet further embodiments, at least one contact sensor is provided, either on the sensor face or on the rear support, or both, that detects whether the test tube is being held firmly between the sensor face and rear support. Measurement is prevented unless the position sensor(s) are engaged. In this manner, measurement on tubes below the minimum diameter is prevented. The contact sensor also provides a mechanism for automating the measurement process: engagement of the contact sensor may provide a trigger signal to commence measurement.

In some embodiments, the contact sensor comprises at least one mechanical switch, which may be activated by contact pressure. In such embodiments the position switches may be located on a printed circuit board within the body of the sensor. Many suitable position switches are available, but one example is manufactured by Omron Electronic Components: part number B3U-1000P-B. This switch requires only 0.15 mm of travel with 150 grams of force in order to be activated, and has a conveniently small footprint (2.5×3.0×1.6 mm). A narrow rod may be used to span the distance between the position switch and front of the sensor. One or more o-rings on the rod may be used to seal the cavity against moisture. This arrangement allows an inexpensive non-waterproof position switch to be used, while still providing protection of the instrument in wet environments.

In an alternate embodiment of the sensor, the position sensing is provided by one or more capacitance sensors. The capacitance sensors may further be selected and positioned so that they are only activated when sufficient medium is present beneath the surface of the window being measured. In yet another embodiment of the sensor, the position sensing is provided by one or more pairs of light sources and detectors. These source-detector pairs may be angled towards each other to detect surface (specular) reflections. The source divergence and detector acceptance angles are restricted so that only when the vessel surface 103 is in the desired orientation relative to the sensor, will a threshold level of surface reflection be detected.

In many embodiments, the apparatus is designed so that sensor face, 7, interfaces near the bottom of the test tube, so that tubes containing only a small amount of medium may still be accurately measured. The use of 2 symmetrically placed detectors around the source provides a method for determining whether sufficient medium is in front of the sensor face for accurate measurement, as further described in U.S. Pat. No. 8,405,033. In an alternative embodiment, only a single detector is employed.

In some embodiments a mechanism is provided for mixing the tube contents, either prior to and/or during the optical measurement. In a preferred embodiment, the mixing mechanism is a shaker, such as a vortex mixer, that interfaces with the bottom of the tube. The mixing is automatically initiated prior to the optical measurement to make sure that all particles are suspended and well-mixed, the mixer is turned off, and then the optical measurement commences. In addition to making sure that the tube contents are well-mixed, the shaker may provide the benefit of dislodging bubbles from the sides of the tube, that may potentially interfere with the optical measurement. In some embodiments a delay time is provided between the mixing period and the optical measurement, in order to allow bubbles to escape from the fluid. In an alternative embodiment, a magnetic stir bar is placed inside the tube, and a magnetically-coupled stirrer is provided near the bottom of the tube.

Alternative Embodiments

In some embodiments, the position of the laser(s) and detector(s) may be interchanged with each other while still maintaining the essential sensor functionality. For example, in the embodiments depicted in FIGS. 11c-d, the single source fiber, 5b, could be replaced with a detector, and the detection fibers replaced by two (FIG. 11c) or more (FIG. 11d) source fibers. In order to separately measure the reflectance that originated with each laser, the lasers may be turned on at different times, or be modulated at different frequencies. When determining measurement validity, the detected signals due to the two different sources are compared, in an equivalent fashion to the manner in which the two detected signals emanating from the single source are compared when employed by the sensors depicted in FIGS. 1a-b, 11c-e, and 18.

In other embodiments, additional lasers and/or detectors are added so that there are source-detector pairs at multiple separation distances. One such embodiment is depicted in FIG. 11c, where optical fiber, 5a, is coupled to a light source, and the 2 remaining fibers, 5b and 5c, are coupled to detectors. Detection fibers 5b and 5c may be separately detected and combined to extend the linear range response to particle concentration. Optimal combinations of source-detector distances for achieving wide linear response to particle concentration, and algorithms for combining the signals from the different source-detector pairs are described in Patent Application US 20090075248, which is included here by reference.

In some embodiments the laser modulation is varied according to the size of the measured reflectance signal detected from the sample. In one such embodiment, the amplitude of the laser modulation ("modulation depth") is increased until a desired reflectance value has been obtained, or a maximum modulation depth has been reached. In this manner the dynamic range of the measurement may be extended, for example allowing a wider range of particle concentrations to be accurately determined.

In some embodiments an analog band-pass filter is added to the detector amplification electronics, that selectively amplifies signals at the frequency of the laser modulation, while attenuating signals outside of the band-pass range.

In some embodiments the reflectance signal is log-transformed twice and related to a singly log-transformed quantity related to particle concentration, such as optical density. This relation may be a linear transformation, higher order polynomial transformation, or other transformation, such as described above. One advantage of some such embodiments is that the relationship between the twice log-transformed reflectance signal to the singly log-transformed particle concentration is linear over a wide range of particle concentrations. After the linear transformation, the signal is inverse log transformed, in order to be representative of particle concentration.

In many of the embodiments described above, a light sources emitting in the vicinity of 1310 1330, or 1550 nm are described. However, light sources emitting in many other spectral regions will also be suitable in the present invention. The absorbance spectrum of water contains multiple bands in the near infrared spectral region, with generally increasing absorbance peaks with increasing wavelength. The spectral region may be selected according to the desired optical depth of penetration, with suitable spectral regions generally increasing in wavelength as the optical depth of penetration is decreased. For example, in applications requiring an optical depth of penetration in the range of 1-10 cm, the 900-1150 nm spectral region is well suited. Water absorbance in this region ranges between about 0.06 and 1.0 cm$^{-1}$, corresponding to a range of mean absorbance path lengths from 1 to 16 cm. One advantage of working in this spectral region is that numerous commercial sources are available, and inexpensive low-noise detectors with Silicon active areas may be employed. In another alternative embodiment, a source in the vicinity of 1550 nm is employed. Such sources have been extensively developed within the telecommunications industry. The strong water absorbance in this spectral region (12 cm$^{-1}$), makes it well suited for short optical penetration depths, such as in the mm range, particularly about 6 mm or less. In a further embodiment of the invention, multiple source wavelengths are employed in the same sensor, with different source wavelengths providing different optical penetration depths, so that the sensor can automatically adapt according to the available fluid depth in front of the sensor.

In many invention embodiments described herein, the physical separation and orientation between sources and detectors are used to diminish the influence of surface (specular) reflections on the measurement in favor of diffuse reflections from particles within a medium. In other embodiments of the invention, additional or alternative methods are used for reducing the influence of specular reflections. Examples of such methods include: (1) the use of crossed-polarizers, (2) Angling of the source and/or detectors, (3) high frequency (e.g. GHz) modulation and detection, (4) the use of short light pulses and high speed detection, and (5) photo-acoustic measurement, where an acoustic detector is used to detect and depth-resolve a light pulse.

In the description of some embodiments, a laser diode light source is described. However, many other light sources could be substituted for the laser diode without substantially modifying the essential features of the invention including: vertical cavity surface emitting lasers (VCSELs), light emitting diodes (LEDs), resonant cavity light emitting diodes, solid state lasers (e.g. Nd-YAG), and gas lasers (e.g. HeNe).

Example 1, Optical Penetration Depth as a Function of Source Wavelength and Source-Detector Separation An immersible fiber optic sensor was constructed and used to investigate the maximum optical depth of penetration of light into an aqueous scattering medium. The body of the sensor was constructed from a hollow aluminum tube, 25 cm long, with 18 mm outer diameter. The end face of the sensor was constructed from black ABS, with holes drilled to guide placement of optical fibers. Optical fibers were positioned flush with the outer sensor face, glued into the place, and optically polished, resulting in a smooth, continuous external surface. The arrangement of the optical fiber on the end face of the sensor is depicted in FIG. 1a. S1-S3, and D1 are 200/220 µm diameter core/cladding fibers with 0.22 NA. D2 and D3 consist of 550/600 µm diameter core fibers with 0.22 NA. S1-S3 are positioned so that they are close-packed along a line. The 7 fibers comprising D3 are 6-around-1 close-packed. Laser diode light sources with three different wavelengths were coupled to three of the fibers: 980 nm (S1), 1310 nm (S2), and 1550 nm (S3). All sources were laser diodes operating at room temperature, modulated at 1 kHz with 25% duty cycle and peak power of 1-10 mW. The detector fibers (D1-D3) were each coupled into separate 1 mm InGaAs detectors. The detector amplifiers passed frequencies from DC to 100 kHz, and the gains were set between $1.6 \times 10^3$ and $1.6 \times 10^4$ V/mW (the lower gain setting was necessary to avoid signal saturation at biomass higher than about 50 g/L). The detector signals were digitized with 16 bit resolution at a sampling rate of 100 kHz using a commercial multi-function data acquisition board (National Instrument USB-6341).

The sensor was suspended in a 1 L glass beaker, filled with Baker's yeast (Red Star Active Dry Yeast) suspended into 0.9% aqueous NaCl, at seven logarithmically spaced concentrations between 0.1 and 100 g/L. A mirror was placed at the bottom of the beaker, parallel to and directly below the optical face of the sensor. The distance between the front face of the sensor and the front face of the mirror was measured. This distance was increased until the signal dropped below the noise floor, and was recorded as the optical penetration depth.

FIG. 2 summarizes the measurements of optical penetration depth as a function of yeast concentration for several different source-detector pairs. The penetration depth depends strongly on the source wavelength, and more weakly on the distance separating the source and detector fibers. The penetration depth determines the minimum fluid depth required for an accurate back-scattering measurement. Water absorbance is weakest at the 980 nm (S1) source wavelength, and the optical penetration at low biomass is in the range of 65 to 90 mm. At 1310 nm (S2), where the water absorbance is between that at 980 and 1550 nm, the penetration depth at low biomass is about 30 mm. With a 1550 nm source (S3) the penetration depth is limited to about 6 mm. As the biomass increases the penetration depth decreases for all source wavelengths, so that by 100 g/L the penetration depth is 10 mm or less in all cases.

Example 2. Biomass Sensitivity Range without Bubbling

The same apparatus as in Example 1 was used to measure the back-reflectance signal as a function of biomass, but with the fiber optic connections re-configured as shown in FIG. 1b. Only the 1310 and 1550 nm sources were used, so that the third linearly close-packed fiber could be connected to a detector. Note that the three other detection fibers/fiber bundles have been re-numbered accordingly. The sensor was immersed in a 12 L Magnferm (NBS) fermentor containing about 10 L of media. The media consisted of 0.9% saline with dry active yeast (Red Star) suspended at 23 different concentrations ranging from 0.1 mg/L to 200 g/L, in a geometric series, with series factor 2. The fermentor was agitated at 400 RPM, and was not bubbled.

Each measurement consisted of 10 seconds of data acquisition ($1 \times 10^6$ total data points were collected on each data channel). Data processing consisted of: (1) demodulation of the detected signals according to the different laser sources, (2) subtraction of the "laser off" signal from each of the "laser on" signals, and (3) normalization of each signal by the source laser power and the detector gain. The first few points at the start and end of each square wave laser pulse were removed, reducing the number of measurement points within each laser pulse from 25 to 20. The result was (100 kHz)×(10 sec)×(25% duty cycle)×(20/25)=$2 \times 10^5$ data points for each source-detector pair. The central value of each data set was estimated by computing the median.

FIG. 3 shows that in the absence of bubbling, by minimizing the separation between the source and detector (S1-D1 and S3-D1), it is possible to measure a monotonic change in back-scattering amplitude over an extremely wide range of biomass: 0.1 mg/L to 200 g/L, or more than 6 orders of magnitude of biomass. This unexpected result demonstrates that it is not necessary to use multiple source-detector separations to achieve a wide range of biomass sensitivity. Furthermore, due to the small size of the fibers (200 μm core) and their minimal separation (close-packed), the sensor size can be greatly reduced, compared to existing commercially available immersible biomass sensors. With the D1 detection fiber, both the 1310 and 1550 nm sources are capable of measuring biomass over a very wide range, although the 1310 nm source produced a more linear response with biomass. By including both sources in a sensor the biomass measured at 2 different depths could be compared, providing a means of rejecting measurements contaminated by reflections from non-biological objects or for which insufficient fluid is present in front of the sensor.

Example 3. Effect of Bubbling on Reflectance Signals

The same apparatus and methods as used in Example 2 were used to collect measurement over a wide range of different agitation rates (0, 200, 400, 600, 800, and 900 RPM) and air bubbling (0, 4, 8, 12, and 16 LPM). Due to the high viscosity of the medium at very high biomass, bubbles take longer to escape from the medium than at lower biomass, so that bubbles constitute a higher fraction of the medium with increasing biomass. For example, with the agitation and sparge set to their maximum values, at a biomass of 100 g/L, bubbles constituted 54% of the total volume, whereas at 10 g/L biomass, bubbles only made up 7% of the total volume.

Figure 4A:
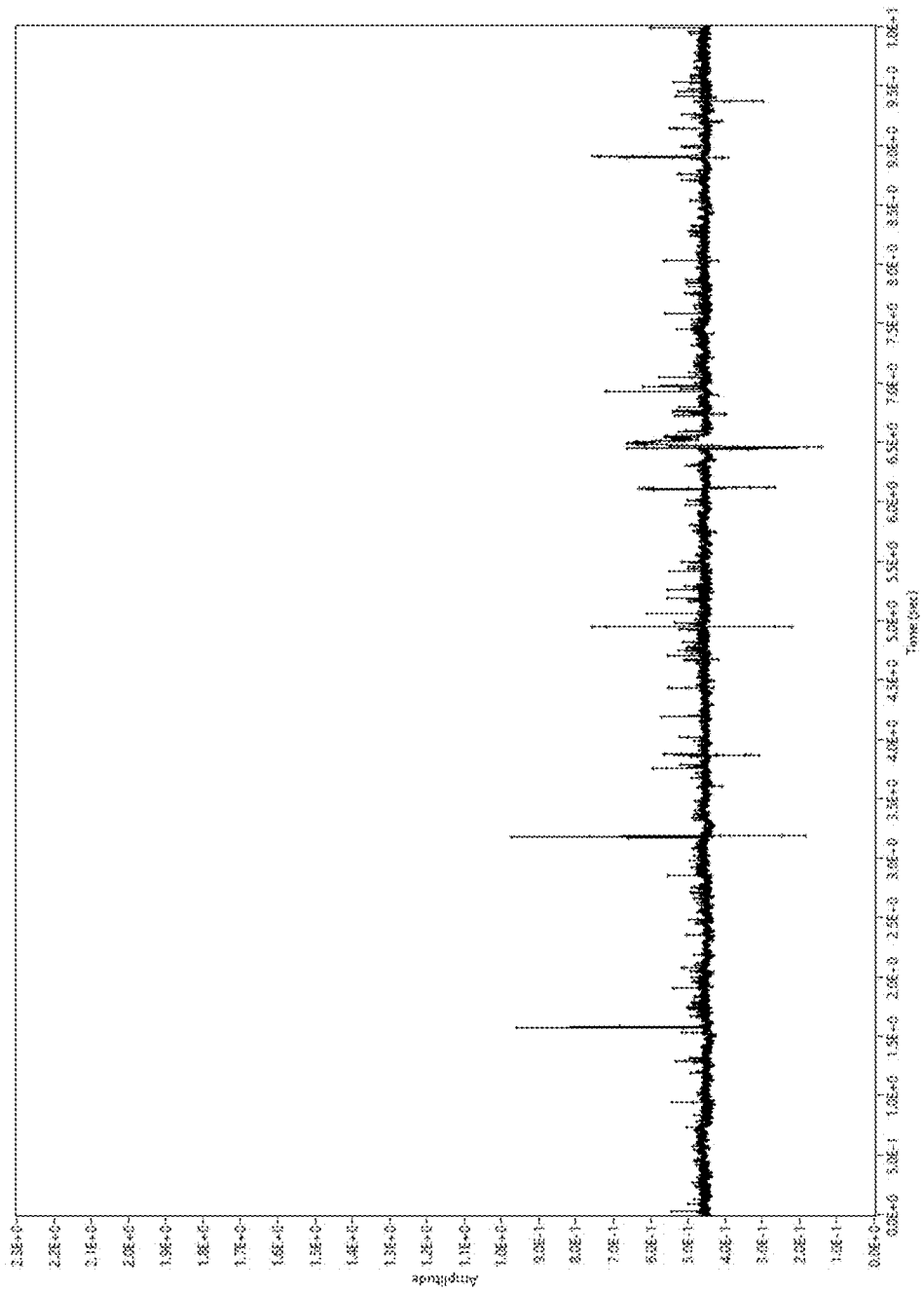
FIG. 4a is graph of back-scattering amplitude as a function of time for a fiber optic source-detector pair immersed in fermentor containing 25 g/L yeast, without bubbling. The source and detector fibers are S1 and D1, as depicted in FIG. 1b.
Figure 4B:
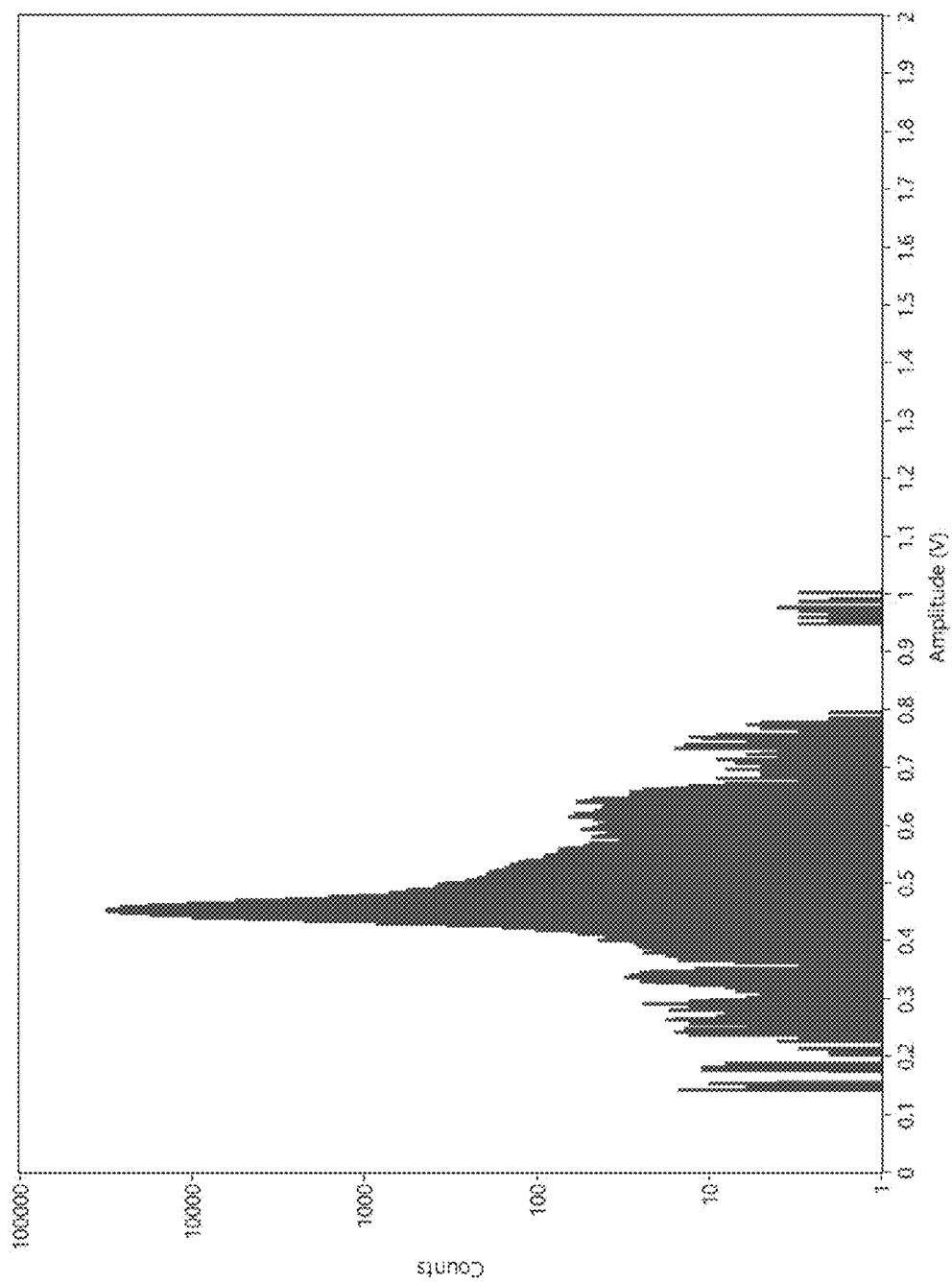
Figure 4C:
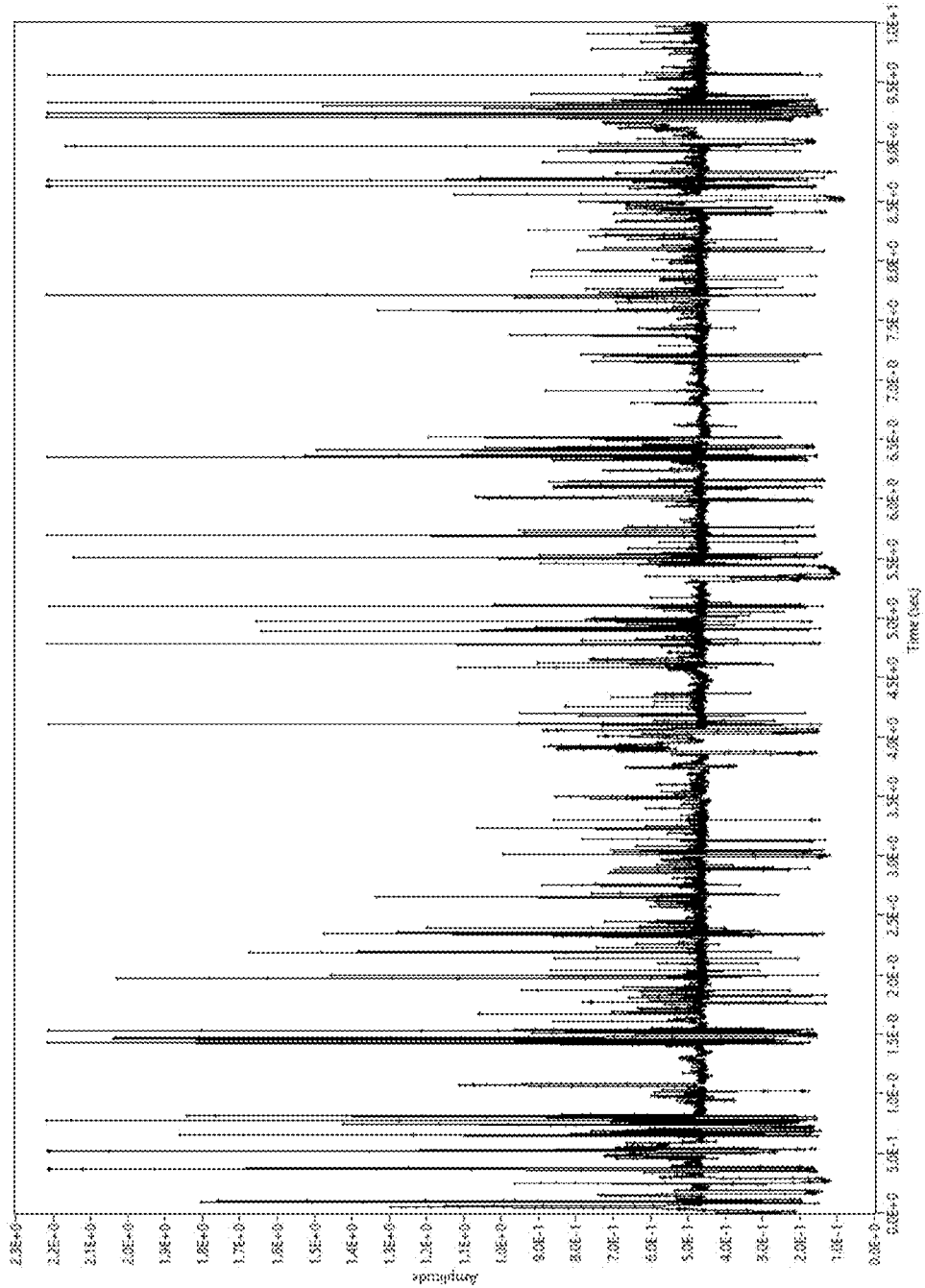
FIG. 4c is graph of back-scattering amplitude as a function of time for a fiber optic source-detector pair immersed in fermentor containing 25 g/L yeast, with vigorous bubbling. The source and detector fibers are S1 and D1, as depicted in FIG. 1b.
Figure 4D:
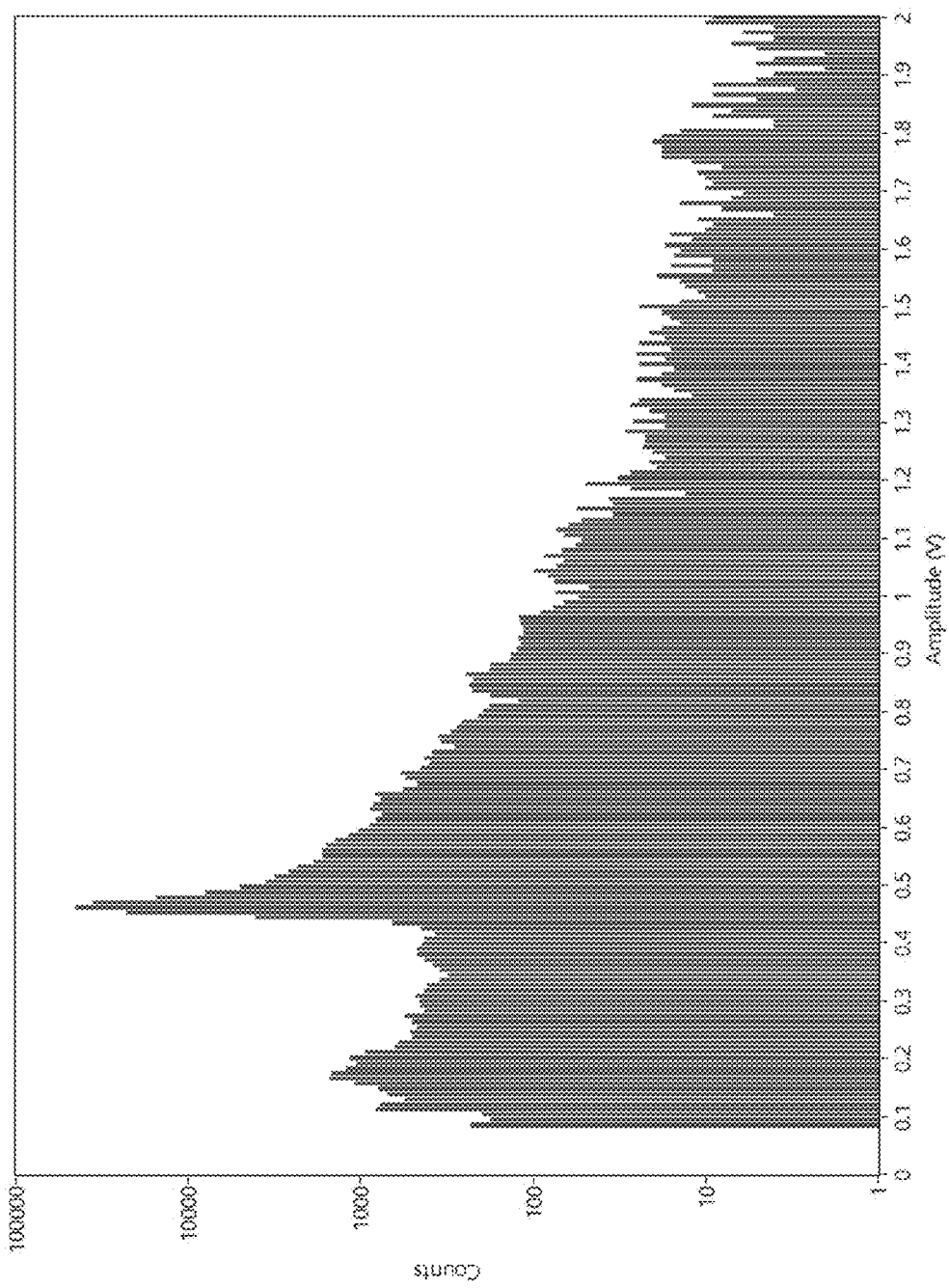
FIG. 4d is a histogram of the data graphed in FIG. 4c.
Figure 4F:
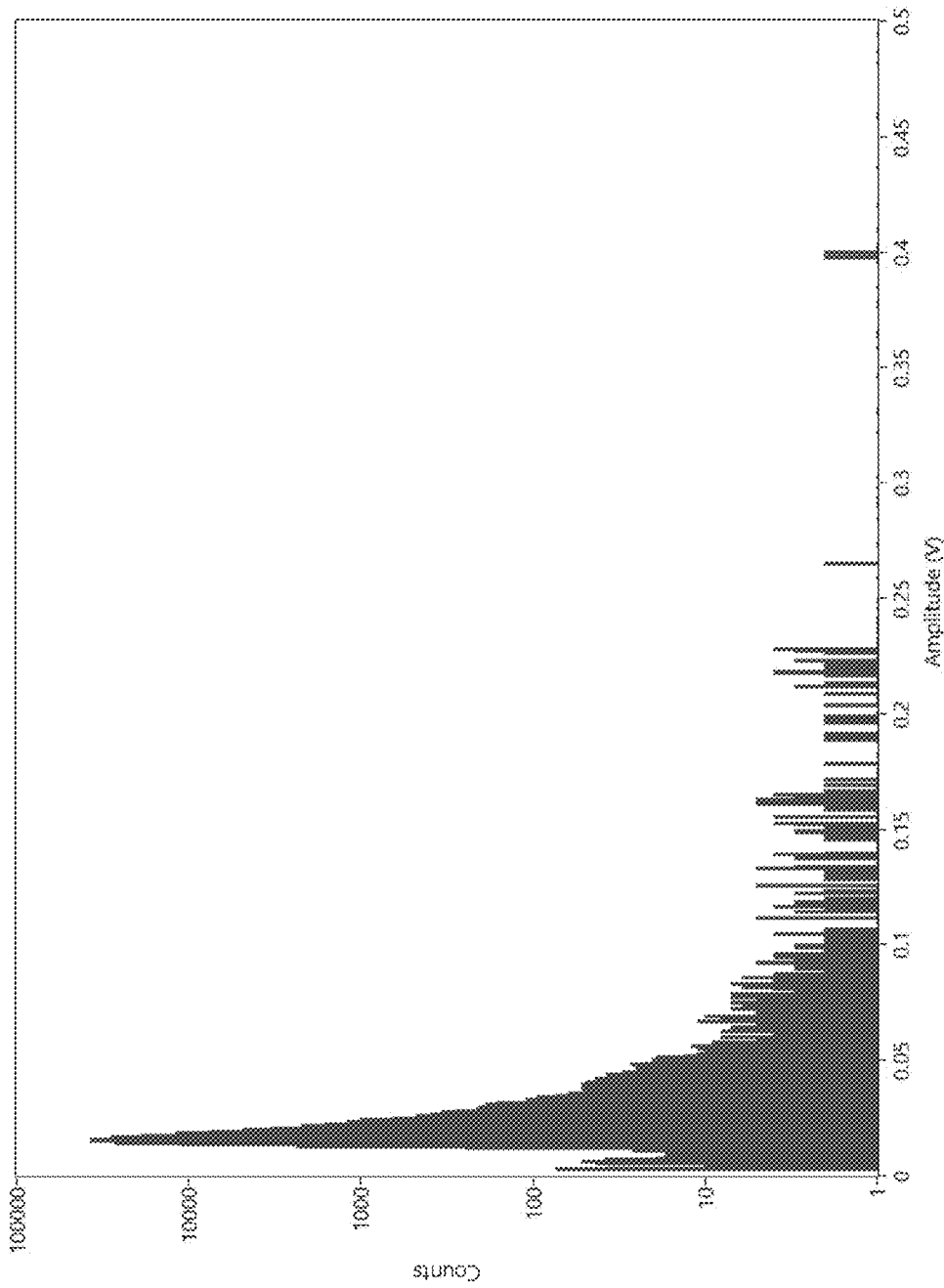
FIG. 4f is a histogram of the data graphed in FIG. 4e.
Figure 4G:
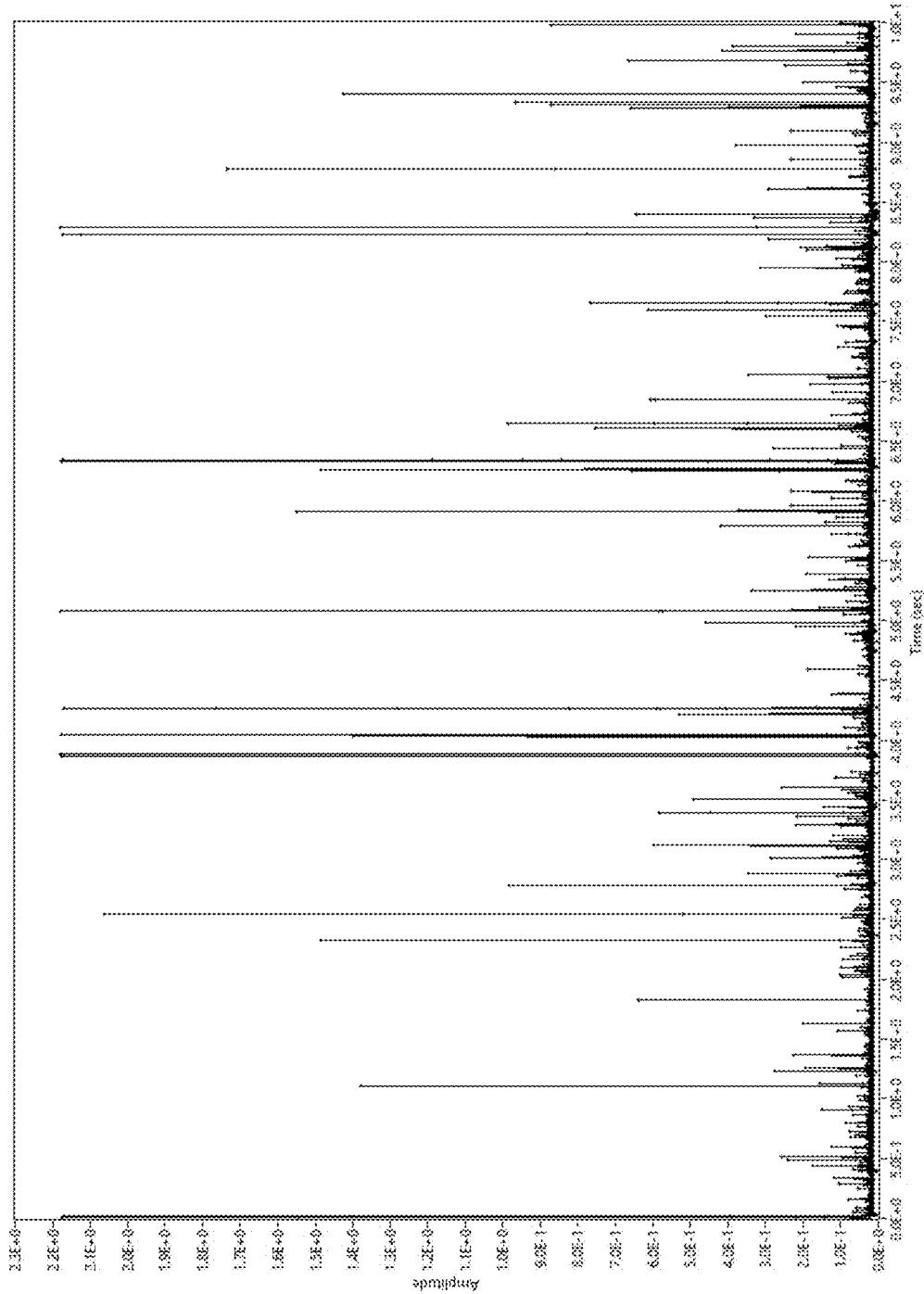
FIG. 4g is graph of back-scattering amplitude as a function of time with a fiber optic source-detector pair immersed in fermentor containing 0.4 g/L yeast, with vigorous bubbling. The source and detector fibers are S1 and D1, as depicted in FIG. 1b.
Figure 4H:
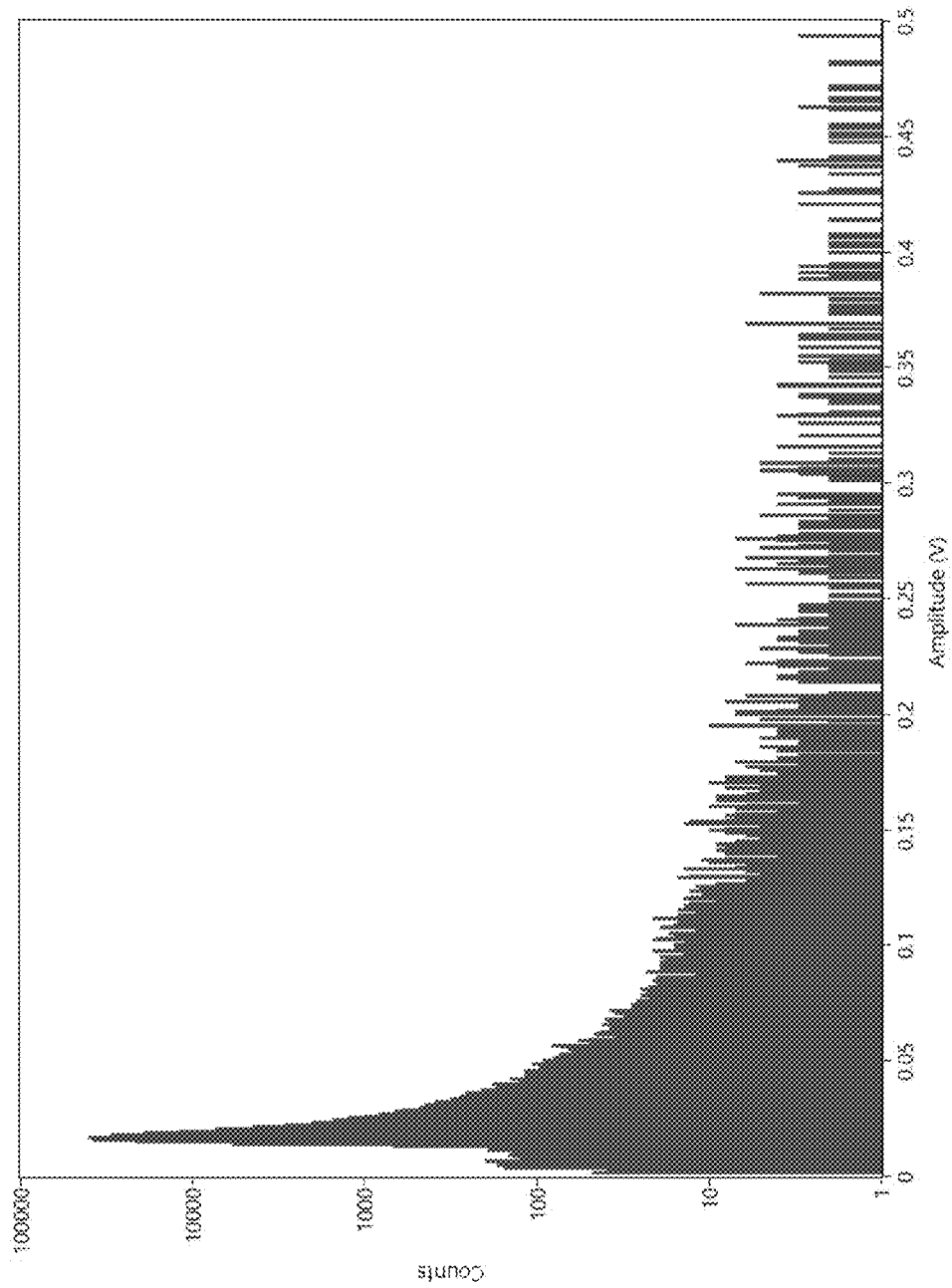
FIG. 4h is a histogram of the data graphed in FIG. 4g.

The S1-D1 (1310 nm laser, close-packed next to detector) signal in 25 g/L yeast with sparging turned off, is shown in FIG. 4a. A histogram of the data (FIG. 4b) shows that the distribution is reasonably symmetrical, so that the mean (0.455), median (0.453), and mode (0.451) are all in close agreement. At the same yeast concentration, but with vigorous bubbling (see FIGS. 4c and 4d), the distribution becomes highly asymmetrical, so that the mean (0.483) is significantly different from the median (0.466) and mode (0.461). Note that the deviations induced by bubbles are both positive and negative-going. The asymmetrical skewing of the signal due to bubbling generally increases as the yeast concentration decreases. For example, FIGS. 4e-h, show the signals measured at 0.4 g/L yeast concentration under conditions of no bubbling (FIG. 4e-f) and high bubbling (FIGS. 4g-h). As shown in Table 1, the mean signal increases by 77% as a result of the bubbling, whereas other measures of central value that are less dependent on outliers, such as the trimmed mean, median, and mode, are less dependent on sparge rate. However, considered on their own (e.g. without also considering statistical measures of the distribution), none of the central value statistics tested so far are able to completely eliminate the effect of bubbles under all conditions.

TABLE 1

Dependence of central signal value on bubbling rate

| File name | Yeast Conc. (g/L) | Sparge Rate (Lpm) | Agitat. Rate (rpm) | Mean | % change | Trimmed Mean | % change | Median | % change | Mode | % change |
|---|---|---|---|---|---|---|---|---|---|---|---|
| 20130925003 | 200 | 0 | 400 | 4.791 | | 4.776 | | 4.773 | | 4.760 | |
| 20130925030 | 200 | 16 | 900 | 5.680 | 19% | 5.943 | 24% | 6.006 | 26% | 6.142 | 29% |
| 20130925093 | 25 | 0 | 400 | 0.462 | | 0.460 | | 0.460 | | 0.460 | |
| 20130925120 | 25 | 16 | 900 | 0.508 | 10% | 0.483 | 5.0% | 0.480 | 4.3% | 0.470 | 2.2% |
| 20130927033 | 3.2 | 0 | 400 | 0.0940 | | 0.0932 | | 0.0932 | | 0.0927 | |
| 20130927059 | 3.2 | 16 | 900 | 0.117 | 24% | 0.0937 | 0.5% | 0.0932 | 0.0% | 0.0927 | 0.0% |
| 20130923393 | 0.4 | 0 | 400 | 0.0168 | | 0.0159 | | 0.0158 | | 0.0150 | |
| 20130923420 | 0.4 | 16 | 900 | 0.0297 | 77% | 0.0173 | 8.8% | 0.0172 | 8.9% | 0.0169 | 13% |
| 20130923303 | 0.05 | 0 | 400 | 0.00395 | | 0.00345 | | 0.00342 | | 0.00306 | |
| 20130923330 | 0.05 | 16 | 900 | 0.0337 | 750% | 0.00561 | 63% | 0.00521 | 52% | 0.00366 | 20% |
| 20130923213 | 0.0064 | 0 | 400 | 0.00163 | | 0.00132 | | 0.00129 | | 0.00107 | |
| 20130923240 | 0.0064 | 16 | 900 | 0.0382 | 2200% | 0.00441 | 230% | 0.00376 | 191% | 0.00178 | 66% |

Example 4. Mitigation of Bubbling Effects

Using the data set as described in Example 3, several different statistical estimates of the central value and distribution were computed, and their efficacy at mitigating the effects of bubbling were evaluated. The central value of each data set was estimated by 4 methods: (1) mean, (2) median, (3) mode, and (4) trimmed mean. The trimmed mean was computed by first sorting the data, then discarding the upper and lower quartile of the data, and computing the mean of the remaining points. The number of bins in the histogram used to compute the mode was generated by dividing the full range by the interquartile range, multiplying by a factor between 3 and 30, and adding a term between 5 and 25. The distribution of each set was estimated by 6 methods: (1) range, (2) standard deviation, (3) interquartile range, (4) mean absolute deviation, (5) median absolute deviation, and (6) mode absolute deviation. The interquartile range was computed by sorting the data and then computing the difference between the values of the data points at the 25th and 75th percentiles.

It is apparent from FIGS. 4a-h that bubbling has a dramatic effect on the signal distribution. Measurement of the signal distribution in combination with measurement of the central value, was found to provide an effective means of diminishing or eliminating the effect of bubbles on the reported biomass. FIG. 5a shows a plot of the Standard Deviation versus the Mean determined using the S1-D4 pair (1310 nm source, S-D separation 6.7 mm). Each yeast level in the figure is represented with a different symbol and color; the displayed yeast range was limited to 0.1 to 25 g/L. The multiple points at each yeast concentration represent measurements collected under different sparge and agitation conditions, with the data points collected under the highest bubbling and agitation rates generally appearing at the upper right of the figure. At each yeast concentration a line was fit to the Mean as a function of the Standard Deviation. The fit was performed in log-log space. The percent RMS difference between the fit and the actual data, computed across all of the yeast concentration was 59%. Several limitations of this measurement configuration are evident from this plot:

i. In the absence of bubbles, the low range biomass limit is about 0.1 g/L.

ii. If only the mean is used to compute the biomass, the presence of bubbles can make it difficult to resolve biomass below about 3 g/L.

iii. The linear range of response to biomass is limited to about 10 g/L. Between 25 and 50 g/L the reflectance signal rolls over and becomes non-monotonic.

iv. Even at the highest linear biomass (~10 g/L), bubbles can have a significant effect on the reported biomass accuracy.

v. Using the standard deviation in combination with the mean to cluster the different yeast concentrations is only effective above about 1.6 g/L.

The beneficial effect of decreasing the source-detector separation can be seen by comparing FIGS. 5a-d in which the respective S-D separations are about 7.1, 3.4, 1.2, and 0.22 mm. At the smallest S-D separation (0.22 mm, FIG. 5d) the resolvable biomass range is extended at both the low and high ends. Further improvement in the data clustering within each yeast concentration results from the use of statistics that are more robust to outliers. Tables 2a and 2b show a comparison of the net RMS fitting errors resulting from linear fits to a central value measure versus a measure of the distribution. The best results were observed when using either the median or the trimmed mean as the central value measure, and using either the interquartile range or median absolute deviation as the distribution measure. Plots of the median absolute deviation versus the median are shown if FIGS. 5e and 5f, for the S1-D1 (1310 nm) and S2-D1 (1550 nm) source-detector pairs, respectively. Compared to the plot of standard deviation vs mean (FIG. 5d), the plot of mean absolute deviation vs median (FIG. 5e) for S1-D1 shows reduced deviation from linearity and better separation between biomass clusters, particularly in the low biomass range, so that the resolvable biomass range is extended by about a factor of 10.

TABLE 2a

S1-D1: Comparison of fitting errors for different statistical measurements of central value and distribution.

|  | Mean | Median | Mode | Trimmed Mean |
|---|---|---|---|---|
| Range | 32% | 9.3% | 5.8% | 11% |
| Interquartile Range | 26% | 2.8% | 3.3% | 2.7% |
| Standard Deviation | 12% | 8.6% | 5.2% | 9.8% |
| Mean Abs. Dev. | 6.3% | 8.0% | 4.9% | 9.1% |
| Median Abs. Dev. | 27% | 2.6% | 3.2% | 2.6% |
| Mode Abs. Dev. | 33% | 3.3% | 5.7% | 3.5% |

TABLE 2b

S2-D1: Comparison of fitting errors for different statistical measurements of central value and distribution.

|  | Mean | Median | Mode | Trimmed Mean |
|---|---|---|---|---|
| Range | 61% | 6.1% | 13% | 6.5% |
| Interquartile Range | 54% | 3.1% | 11% | 3.0% |
| Standard Deviation | 26% | 4.8% | 12% | 5.1% |
| Mean Abs. Dev. | 9.2% | 4.3% | 12% | 4.5% |
| Median Abs. Dev. | 53% | 2.9% | 11% | 2.7% |
| Mode Abs. Dev. | 46% | 3.4% | 12% | 3.4% |

Example 5. Bandwidth and Data Processing Requirements

Figure 6A:
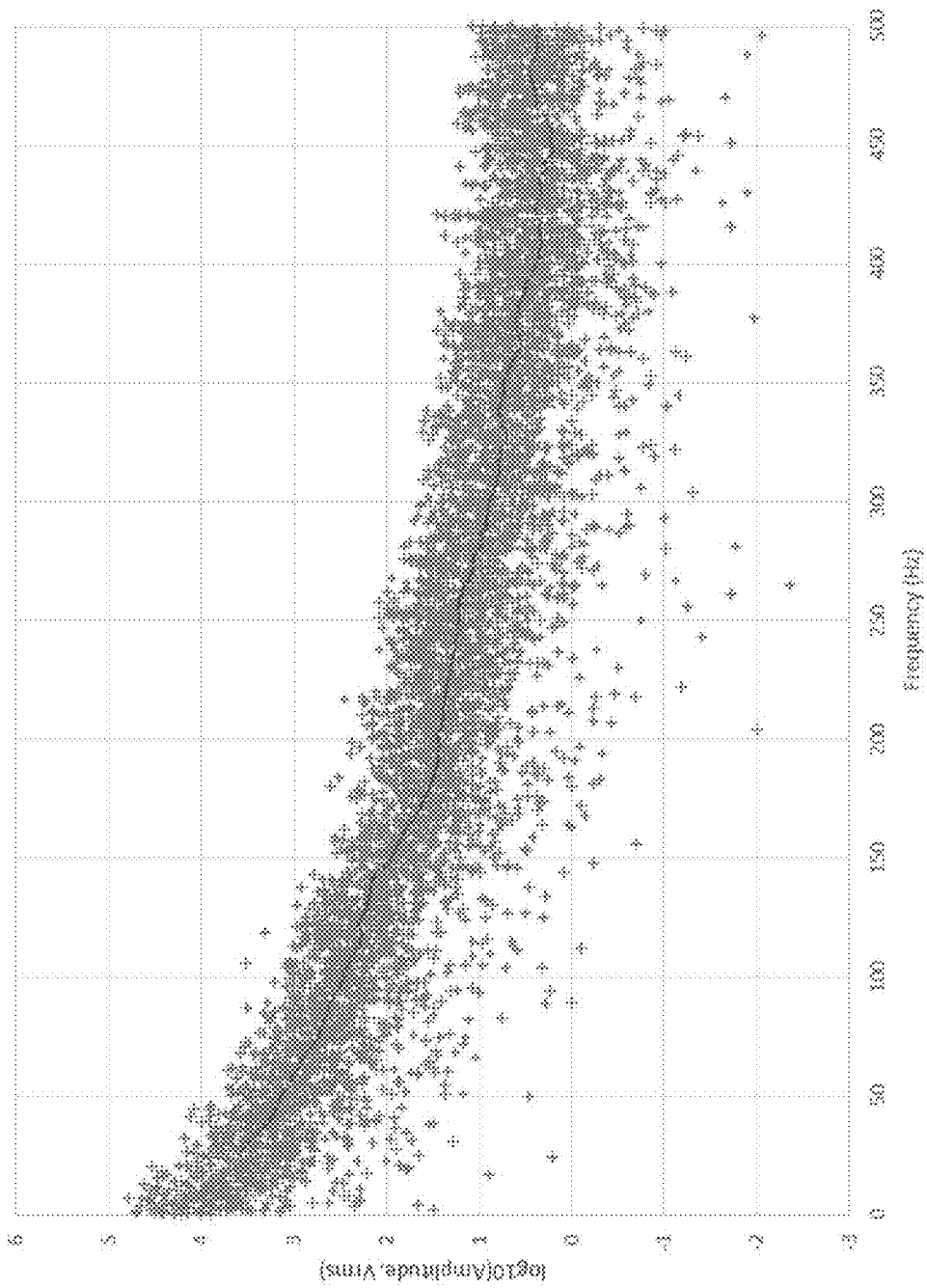
FIG. 6a is a power spectrum graph of the logarithm of the reflectance signal as a function of sampling frequency measured with a sensor of the present invention having a source wavelength of 1310 nm, and a source-detector separation of about 0.22 mm (S1-D1 in FIG. 1b), that was immersed in a 12 L bioreactor containing 200 g/L yeast dissolved in 10 L of 0.9% saline, agitated at 900 rpm and sparged with air at 16 lpm.
Figure 6B:
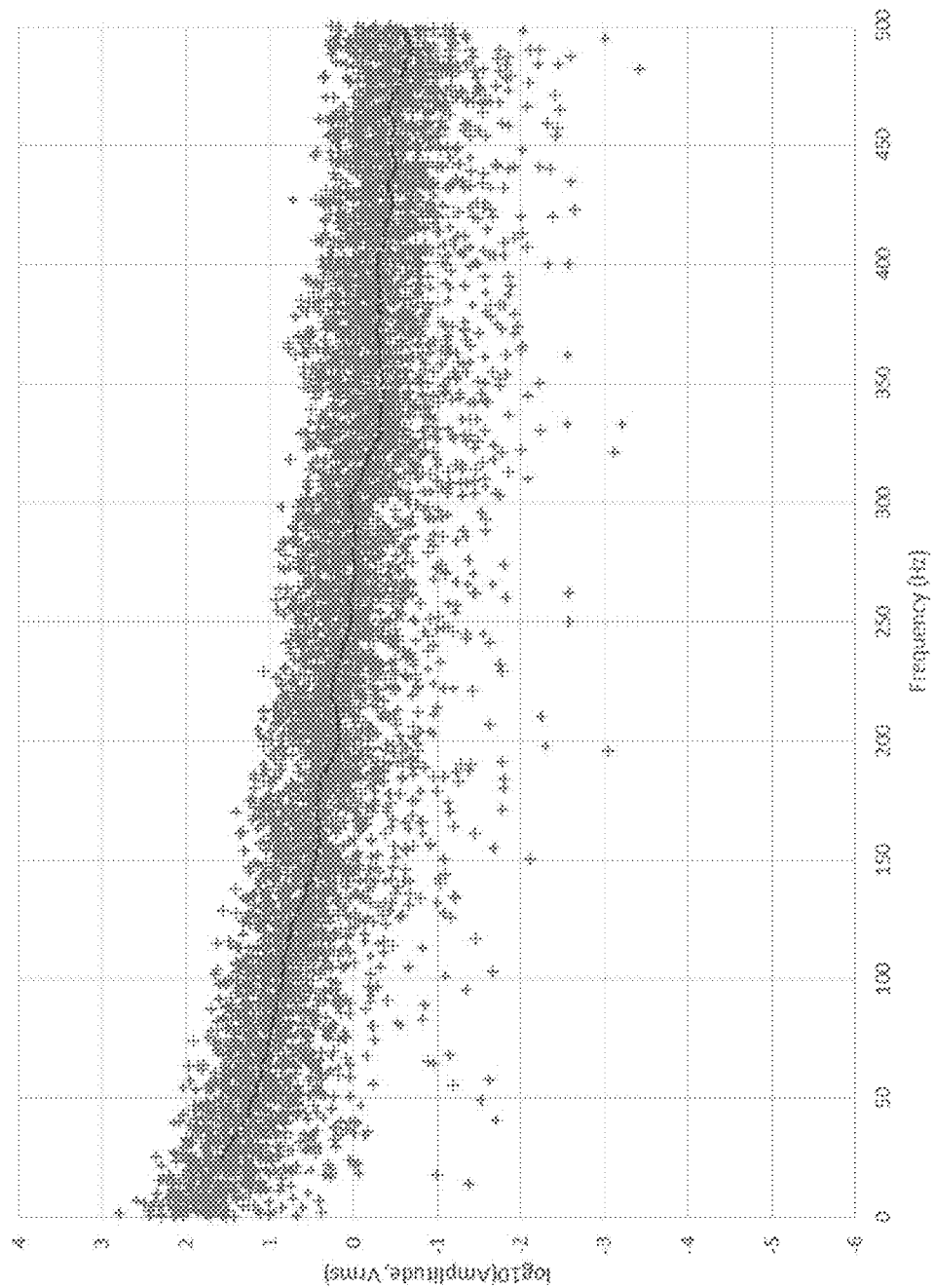
FIG. 6b is a power spectrum graph of the logarithm of the reflectance signal as a function of sampling frequency measured with a sensor of the present invention having a source wavelength of 1310 nm, and a source-detector separation of about 0.22 mm (S1-D1 in FIG. 1b), that was immersed in a 12 L bioreactor containing 6 g/L yeast dissolved in 10 L of 0.9% saline, agitated at 900 rpm and sparged with air at 16 lpm.
Figure 6C:
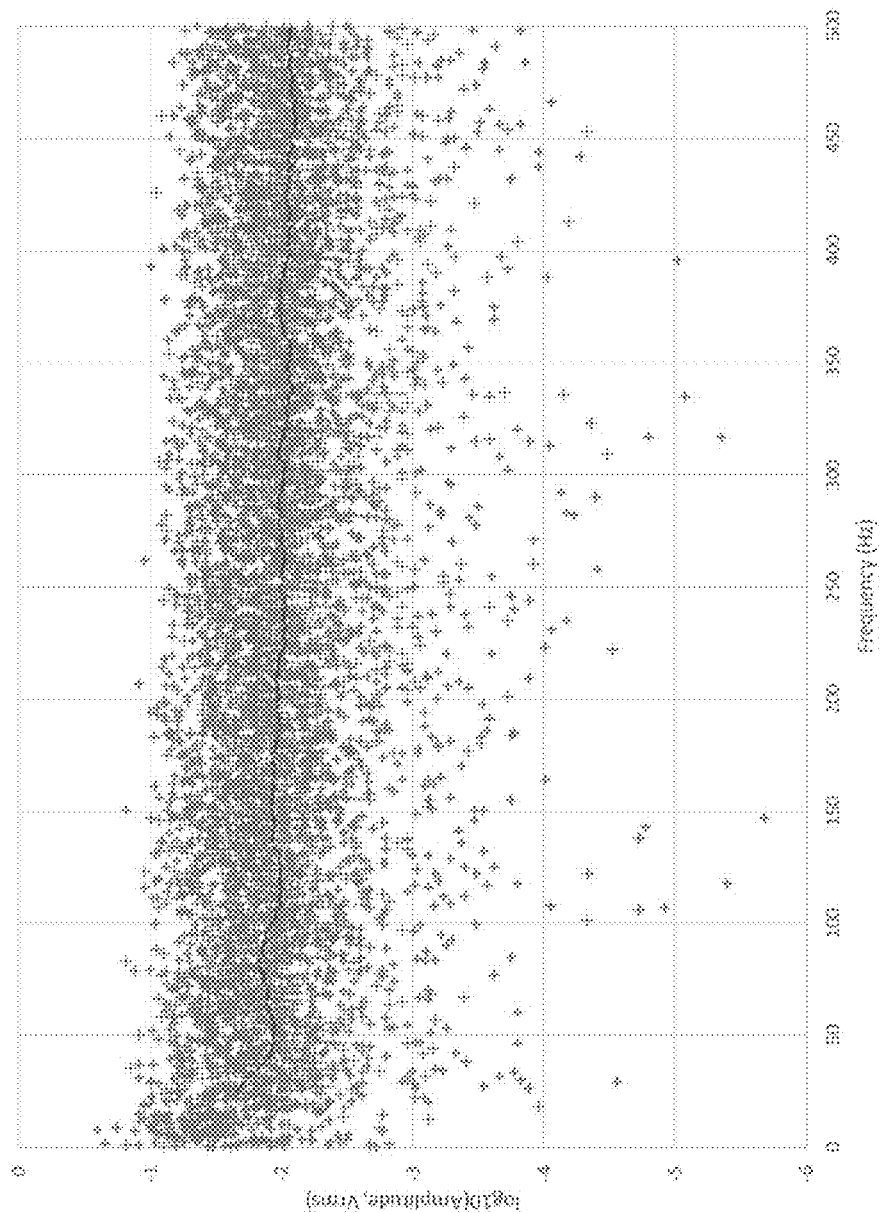
FIG. 6c is a power spectrum graph of the logarithm of the reflectance signal as a function of sampling frequency measured with a sensor of the present invention having a source wavelength of 1310 nm, and a source-detector separation of about 0.2 mm (S1-D1 in FIG. 1b), that was immersed in a 12 L bioreactor containing 6 g/L yeast dissolved in 10 L of 0.9% saline, agitated at 400 rpm and with no air sparging.

Using the same data set as in Examples 3 and 4, frequency analysis was performed and additional data pre-processing methods were applied to evaluate the necessary bandwidth and processing power to achieve high discrimination against bubbles. Fourier Transform power spectra are shown in FIG. 6a-c, under conditions of high biomass and high sparge (6a), medium biomass and high sparge (6b), and medium biomass and no sparge (6c). FIG. 6a shows that at high biomass the majority of the bubbles are resolved at frequencies below about 400 Hz (800 Hz bandwidth). At medium biomass, but with the same agitation and sparge conditions (FIG. 6b), the power spectrum is less steeply sloped, and the majority of bubbles are resolved at frequencies below about 300-350 Hz (600-700 Hz band width). With sparge turned off at medium biomass (FIG. 6c), the power spectrum is nearly flat.

Additional variable data processing steps included: (1) averaging of all data points within each laser pulse, (2) decimating the data by factors of 2-8, and (3) truncating the data sets by factors of 2-16. Decimation was performed by averaging D adjacent data points, where the decimation factor is D. Truncation was performed by dividing the number of data samples, N, by the truncation factor M, and keeping only the first N/M samples in the data set. Decimation and truncation were always performed after averaging of the data points within each laser pulse. When both decimation and truncation were performed on the same data set, decimation was performed first.

Figure 7A:
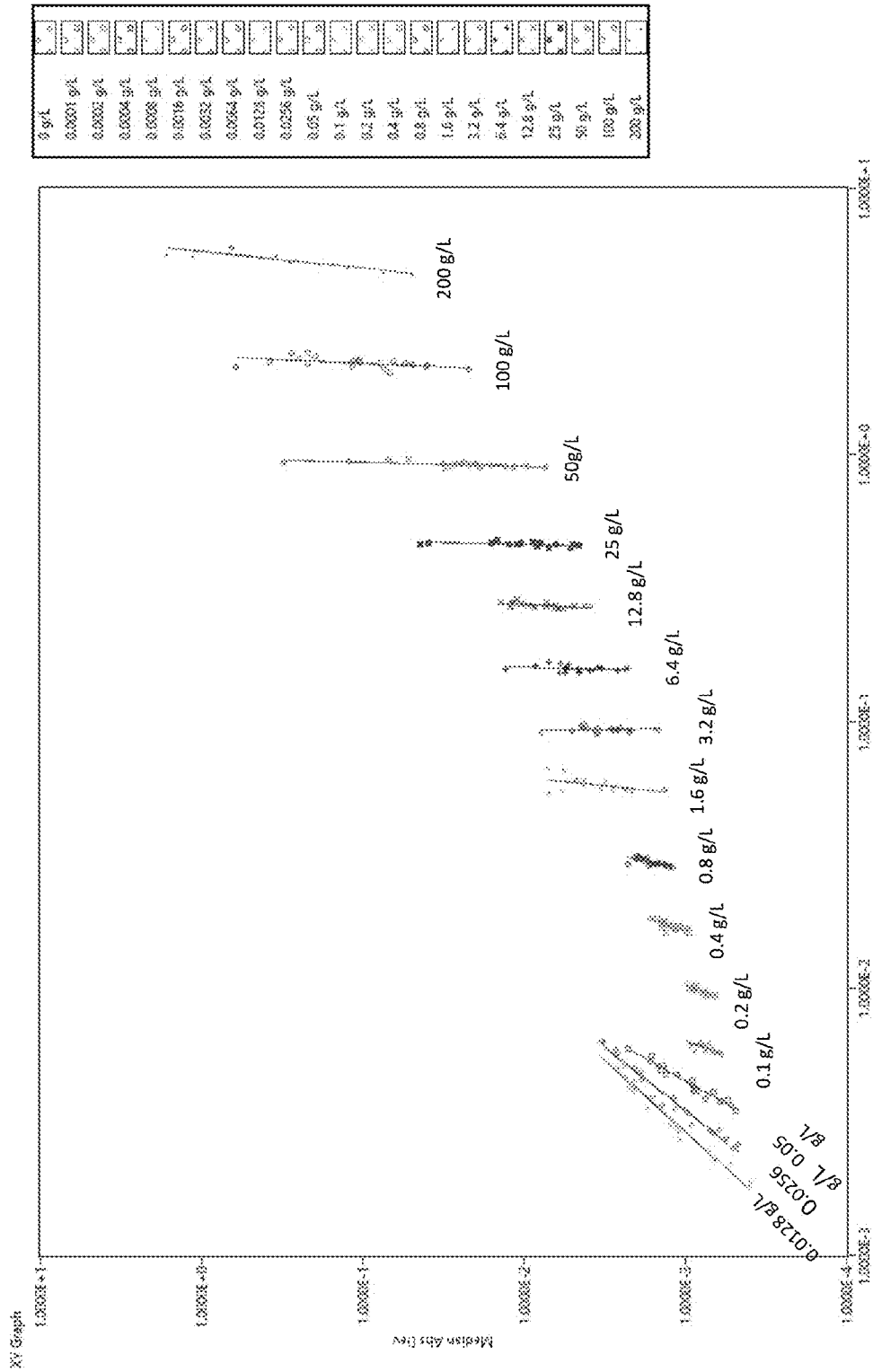
FIG. 7a is a graph of the same data as in FIG. 5e after decimating the data by a factor of two, and then truncating the data by a factor of four.
Figure 7B:
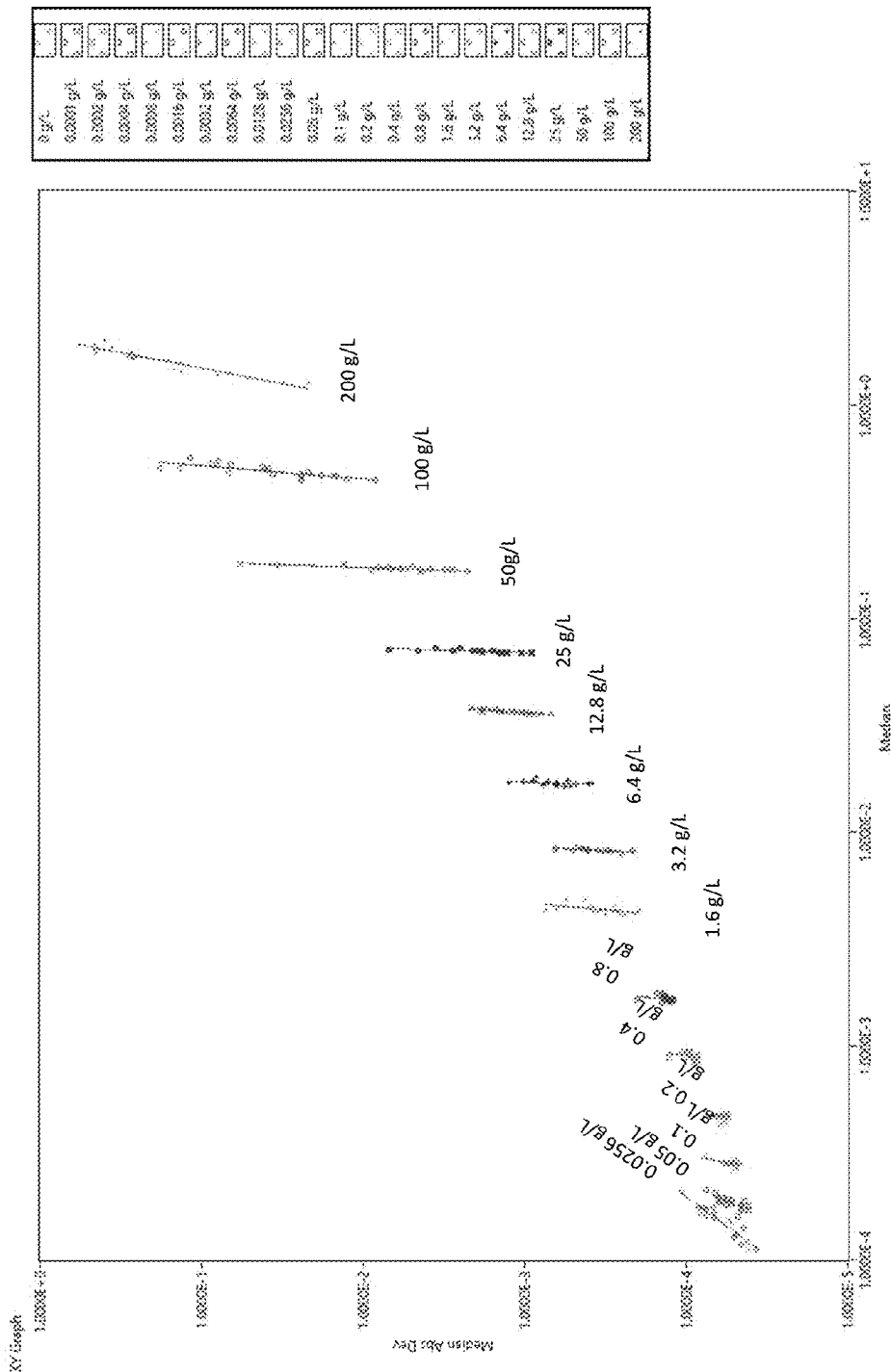
FIG. 7b is a graph of the same data as in FIG. 5f after decimating the data by a factor of two, and then truncating the data by a factor of four.

The minimum necessary bandwidth and number of data points were explored by decimating and/or truncating the data sets and then comparing the linear fitting errors for plots of the median absolute deviation versus the median, across a wide range of yeast concentrations. The results are summarized in Tables 3a and 3b, respectively, for the S1-D1 (1310 nm) and S2-D1 (1550 nm) source-detector pairs. FIGS. 7a and 7b show the fitting results for the S1-D1 and S2-D1 source-detector pairs, respectively, with the decimation factor set to 2 (500 Hz band width) and the truncation factor set to 4 (1250 data points). Compared to the results with no within-pulse averaging, at full bandwith (1 kHz) and no truncation (2×105 data points) (FIGS. 5e and 5f), the decimation and truncation have little apparent effect on the ability to accurately resolve biomass in the presence of bubbles. The dependence of the Net RMS Error on the truncation factor is relatively weak, and can be increased up to 64 while maintaining the Net RMS Error below 6%. FIGS. 7a and 7b respectively show the S1-D1 and S2-D1 fitting results for decimation factor 2 and truncation factor 64 (N=78). Loss of resolution is most evident in the low biomass range (compared to FIGS. 6e and 6f).

TABLE 3a

S1-D1: Comparison of fitting errors (median absolute deviation vs. median) after different levels of data decimation and truncation.

| Decimation Factor (D) | Truncation Factor (M) | Bandwidth (Hz) | Number of Points (N) | Net RMS Error | Resolveable Yeast Range (g/L) |
|---|---|---|---|---|---|
| 1 | 1 | 1000 | 10,000 | 2.77% | 0.01-200 |
| 2 | 1 | 500 | 5,000 | 3.11% | 0.01-200 |
| 4 | 1 | 250 | 2,500 | 3.86% | 0.02-200 |
| 8 | 1 | 125 | 1,250 | 5.16% | 0.05-200 |
| 1 | 2 | 1000 | 5,000 | 2.80% | 0.01-200 |
| 1 | 4 | 1000 | 2,500 | 2.89% | 0.01-200 |
| 1 | 8 | 1000 | 1,250 | 3.07% | 0.01-200 |

TABLE 3a-continued

S1-D1: Comparison of fitting errors (median absolute deviation vs. median) after different levels of data decimation and truncation.

| Decimation Factor (D) | Truncation Factor (M) | Bandwidth (Hz) | Number of Points (N) | Net RMS Error | Resolveable Yeast Range (g/L) |
|---|---|---|---|---|---|
| 1 | 16 | 1000 | 625 | 3.70% | 0.01-200 |
| 1 | 32 | 1000 | 312 | 4.19% | 0.01-200 |
| 1 | 64 | 1000 | 156 | 4.69% | 0.02-200 |
| 1 | 128 | 1000 | 78 | 12.2% | 0.05-200 |
| 2 | 2 | 500 | 2,500 | 3.15% | 0.01-200 |
| 2 | 4 | 500 | 1,250 | 3.17% | 0.01-200 |
| 2 | 8 | 500 | 625 | 3.23% | 0.01-200 |
| 2 | 16 | 500 | 312 | 4.04% | 0.02-200 |
| 2 | 32 | 500 | 156 | 4.71% | 0.02-200 |
| 2 | 64 | 500 | 78 | 5.11% | 0.02-200 |
| 2 | 128 | 500 | 39 | 12.2% | 0.05-200 |
| 4 | 16 | 250 | 156 | 4.78% | 0.02-200 |
| 4 | 32 | 250 | 78 | 5.65% | 0.02-200 |
| 4 | 64 | 250 | 39 | 5.96% | 0.05-200 |
| 4 | 128 | 250 | 19 | 13.7% | 0.1-200 |

TABLE 3b

S2-D1: Comparison of fitting errors (median absolute deviation vs. median) after different levels of data decimation and truncation.

| Decimation Factor (D) | Truncation Factor (M) | Bandwidth (Hz) | Number of Points (N) | Net RMS Error | Resolveable Yeast Range (g/L) |
|---|---|---|---|---|---|
| 1 | 1 | 1000 | 10,000 | 3.09% | 0.02-200 |
| 2 | 1 | 500 | 5,000 | 3.04% | 0.02-200 |
| 4 | 1 | 250 | 2,500 | 3.03% | 0.02-200 |
| 8 | 1 | 125 | 1,250 | 3.33% | 0.02-200 |
| 1 | 2 | 1000 | 5,000 | 3.08% | 0.02-200 |
| 1 | 4 | 1000 | 2,500 | 3.17% | 0.02-200 |
| 1 | 8 | 1000 | 1,250 | 3.61% | 0.02-200 |
| 1 | 16 | 1000 | 625 | 3.88% | 0.05-200 |
| 1 | 32 | 1000 | 312 | 4.68% | 0.05-200 |
| 1 | 64 | 1000 | 156 | 5.65% | 0.05-200 |
| 1 | 128 | 1000 | 78 | 9.12% | 0.05-200 |
| 2 | 2 | 500 | 2,500 | 3.21% | 0.02-200 |
| 2 | 4 | 500 | 1,250 | 3.12% | 0.02-200 |
| 2 | 8 | 500 | 625 | 3.61% | 0.02-200 |
| 2 | 16 | 500 | 312 | 3.67% | 0.02-200 |
| 2 | 32 | 500 | 156 | 4.71% | 0.02-200 |
| 2 | 64 | 500 | 78 | 5.55% | 0.05-200 |
| 2 | 128 | 500 | 39 | 9.43% | 0.05-200 |
| 4 | 16 | 250 | 156 | 3.88% | 0.02-200 |
| 4 | 32 | 250 | 78 | 5.19% | 0.05-200 |
| 4 | 64 | 250 | 39 | 6.56% | 0.05-200 |
| 4 | 128 | 250 | 19 | 10.5% | 0.05-200 |

Processing of the data in 2 steps could reduce the processing power and memory requirements of the apparatus. 2-stage methods for computing the central value and distribution are compared in Tables 4 and 5. In the first data processing stage, the central value was estimated by 3 methods (trimmed mean, median, and mode) and the distribution was estimated by 3 methods (range, interquartile "IQ" range, and median absolute deviation "MAD"). In the second data processing stage, each of the 3 central value methods was applied to each of the first stage estimates, resulting in 9 combinations of methods (the second stage method is shown in parentheses in the row and column labels). The distributions were computed in the second stage by applying the three central value estimation methods to the distributions computed in the first stage.

The results shown in Tables 4a and 4b were determined with the number of data points fixed at 32 and the trim percentages fixed at 25% in both stages. The lowest fitting errors resulted when the MAD method was used to estimate the distribution in the first data processing stage. All methods using the mode to estimate the central value gave significantly higher fitting errors compared to those employing the trimmed mean or median.

TABLE 4a

S1-D1: Comparison of 2 step data processing methods (N1 = 32, N2 = 32, Trim1 = 25%, Trim2 = 25%, 0.01-200 g/L, 400-900 rpm, 0-16 1pm).

|  | Tr. Mean (Tr. Mean) | Tr. Mean (Median) | Tr. Mean (Mode) | Median (Tr. Mean) | Median (Median) | Median (Mode) | Mode (Tr. Mean) | Mode (Median) | Mode (Mode) |
|---|---|---|---|---|---|---|---|---|---|
| Range (Tr. Mean) | 7.29 | 7.11 | 11.2 | 6.49 | 6.14 | 9.97 | 7.61 | 8.72 | 18.8 |
| Range (Median) | 6.71 | 6.55 | 10.6 | 5.97 | 5.65 | 9.73 | 8.20 | 7.76 | 18.8 |
| Range (Mode) | 9.07 | 8.74 | 11.4 | 7.98 | 7.52 | 10.0 | 11.1 | 11.0 | 18.6 |
| IQ Range (Tr. Mean) | 3.64 | 3.64 | 9.95 | 3.69 | 3.57 | 8.96 | 8.45 | 7.22 | 16.9 |
| IQ Range (Median) | 3.80 | 3.62 | 10.0 | 3.80 | 3.62 | 9.11 | 9.11 | 7.53 | 16.7 |
| IQ Range (Mode) | 11.9 | 11.4 | 10.5 | 10.4 | 9.85 | 12.2 | 17.4 | 15.7 | 19.5 |
| MAD (Tr. Mean) | 3.33 | 3.45 | 9.63 | 3.31 | 3.30 | 8.77 | 8.67 | 7.18 | 17.4 |
| MAD (Median) | 3.40 | 3.38 | 9.59 | 3.34 | 3.26 | 8.70 | 8.76 | 7.18 | 17.5 |
| MAD (Mode) | 11.1 | 10.6 | 8.04 | 9.62 | 9.06 | 6.86 | 17.4 | 15.1 | 19.9 |

TABLE 4b

S2-D1: Comparison of 2 step data processing methods (N1 = 32,
N2 = 32, Trim1 = 25%, Trim2 = 25%, 0.01-200 g/L, 400-900 rpm, 0-16 1pm).

|  | Tr. Mean (Tr. Mean) | Tr. Mean (Median) | Tr. Mean (Mode) | Median (Tr. Mean) | Median (Median) | Median (Mode) | Mode (Tr. Mean) | Mode (Median) | Mode (Mode) |
|---|---|---|---|---|---|---|---|---|---|
| Range (Tr. Mean) | 5.16 | 4.33 | 14.6 | 4.52 | 4.12 | 9.56 | 7.52 | 6.82 | 31.1 |
| Range (Median) | 5.32 | 4.44 | 14.6 | 4.64 | 4.22 | 9.52 | 9.02 | 6.51 | 32.1 |
| Range (Mode) | 6.72 | 5.79 | 15.4 | 5.90 | 5.37 | 10.1 | 14.0 | 9.52 | 20.7 |
| IQ Range (Tr. Mean) | 3.76 | 4.43 | 14.4 | 3.94 | 4.14 | 9.56 | 10.6 | 8.57 | 30.5 |
| IQ Range (Median) | 4.06 | 3.84 | 14.6 | 4.03 | 3.91 | 9.70 | 8.63 | 7.12 | 30.7 |
| IQ Range (Mode) | 7.80 | 6.81 | 10.3 | 6.87 | 6.21 | 11.6 | 17.3 | 11.4 | 35.2 |
| MAD (Tr. Mean) | 3.76 | 4.27 | 14.4 | 3.80 | 3.99 | 9.61 | 10.6 | 8.44 | 30.1 |
| MAD (Median) | 4.14 | 3.88 | 14.6 | 3.91 | 3.83 | 9.76 | 9.72 | 7.84 | 30.2 |
| MAD (Mode) | 7.34 | 6.58 | 12.4 | 6.53 | 5.97 | 7.67 | 16.6 | 11.3 | 37.3 |

Three of the methods giving the best results in Tables 4a and 4b were further explored by varying the number of data points (N1, N2) and trim percentages (Trim 1, Trim 2) in the two processing stages. The results (Tables 5a and 5b) show that the fitting is only weakly dependent on the ratio of N1 to N2 and the trim percentages. A more significant dependence is seen on the total number of data point (N1+N2).

TABLE 5a

S1-D1: Comparison of 2 step data processing methods (0.01-200 g/L, 400-900 RPM, 0-16 LPM).

| N1 | Trim 1 | N2 | Trim 2 | Tr. Mean (Tr. Mean): MAD (Tr. Mean) | Med. (Tr. Mean): MAD (Tr. Mean) | Med. (Med.): MAD (Med.) |
|---|---|---|---|---|---|---|
| 128 | 25 | 8 | 25 | 3.37 | 3.42 | 3.47 |
| 64 | 25 | 16 | 25 | 3.48 | 3.48 | 3.73 |
| 32 | 25 | 32 | 25 | 3.33 | 3.31 | 3.26 |
| 16 | 25 | 64 | 25 | 3.11 | 3.13 | 3.23 |
| 8 | 25 | 128 | 25 | 2.93 | 2.84 | 3.05 |
| 32 | 35 | 32 | 35 | 3.25 | 3.22 | 3.26 |
| 32 | 15 | 32 | 15 | 3.50 | 3.49 | 3.26 |
| 32 | 15 | 32 | 35 | 3.43 | 3.22 | 3.26 |
| 32 | 25 | 16 | 25 | 4.69 | 4.73 | 4.70 |
| 32 | 25 | 8 | 25 | 5.14 | 5.07 | 5.13 |
| 16 | 25 | 32 | 25 | 4.52 | 4.77 | 4.31 |
| 8 | 25 | 32 | 25 | 5.01 | 4.90 | 5.25 |
| 8 | 35 | 128 | 35 | 2.79 | 2.90 | 3.05 |

TABLE 5b

S2-D1: Comparison of 2 step data processing methods (0.02-200 g/L, 400-900 RPM, 0-16 LPM).

| N1 | Trim 1 | N2 | Trim 2 | Tr. Mean (Tr. Mean): MAD (Tr. Mean) | Med. (Tr. Mean): MAD (Tr. Mean) | Med. (Med.): MAD (Med.) |
|---|---|---|---|---|---|---|
| 128 | 25 | 8 | 25 | 3.64 | 3.67 | 3.82 |
| 64 | 25 | 16 | 25 | 3.76 | 3.78 | 4.05 |
| 32 | 25 | 32 | 25 | 3.76 | 3.80 | 3.83 |
| 16 | 25 | 64 | 25 | 3.82 | 3.80 | 3.99 |
| 8 | 25 | 128 | 25 | 4.06 | 4.10 | 4.29 |
| 32 | 35 | 32 | 35 | 3.79 | 3.84 | 3.83 |
| 32 | 15 | 32 | 15 | 4.24 | 3.80 | 3.83 |
| 32 | 15 | 32 | 35 | 3.89 | 3.84 | 3.83 |
| 32 | 25 | 16 | 25 | 4.63 | 4.86 | 5.47 |
| 32 | 25 | 8 | 25 | 5.84 | 5.70 | 5.60 |
| 16 | 25 | 32 | 25 | 4.39 | 4.40 | 4.71 |
| 8 | 25 | 32 | 25 | 6.35 | 6.22 | 6.17 |
| 8 | 35 | 128 | 35 | 4.13 | 4.21 | 4.29 |

Example 6. Extrapolation of Immersion Sensor Results to Non-Invasive Sensor Measurements The fiber immersion sensor results indicate that the widest biomass range and best biomass clustering across different bubbling conditions are obtained with the Source-Detector separation minimized (e.g., close-packed optical fibers). For non-invasive measurements, an intervening layer of glass or plastic (the container wall) will separate the sensor from the medium. The effect of this intervening layer on the source-detector overlap was modeled, with the approximation that the mean optical depth corresponds to the point of overlap of rays with maximum divergence from and to the center axis of the source and detector fibers, respectively.

The optical model is depicted in FIG. 8, and the results are summarized in Table 6. Configuration 1 in Table 6 corresponds to an immersion sensor, for which the source (D1) and detector (D2) fibers both have 0.2 mm core diameters and numerical apertures of 0.22. For this configuration, the wall thickness, T, was set to 0, and the edge-to-edge separation between the source and detector fiber cores, Y was set to 0.04 mm (closest-packing allowed for a fiber cladding diameter of 0.22 mm). The resulting source-detector overlap depth, X, within the medium, is 0.71 mm. All other configurations in Table 6 correspond to non-invasive measurements through a wall with thickness, T. For the non-invasive configurations, the overlap depth, X, was fixed at 0.71, and the resultant edge-to-edge separation between the fiber cores, Y, was determined. The closest point of intersection between the source and detector fiber cones, Z, within the container wall was also determined. A negative value of Z indicates that the source and detector cones will overlap within the container wall, with the result that back (specular) reflections could be observed from the wall-medium interface. In the case of configurations 2-10, the wall thickness is 2.1 mm. As shown for configuration 3 in Table 6, if the fiber size and type is kept the same as in the immersion sensor case (configuration 1), but the optical cones travel through an intervening glass wall that is 2.1 mm thickness, an edge-to-edge fiber core separation, Y=0.66 mm, will result in the same overlap depth within the medium as in the immersion sensor case.

Y scales linearly with the wall thickness, so for configuration 11 having a 1 mm wall thickness, Y=0.34 mm, while for a typical lab-scale glass fermentor (1-12 L volume) with 6 mm wall thickness (configuration 12), Y=01.8. If a sensor with the fiber edge-to-edge separation optimized for a vessel with 2.1 mm thickness (Configuration 3, Y=0.66 mm) was used on a larger vessel with a 6 mm wall, Z would be negative, indicating that the sensor would pick up back-reflections from the interface between the container wall and the medium. On the other hand, if a configuration optimized for a 2.1 mm wall thickness (Configuration 3) was used on vessel with a 1 mm thick wall (Configuration 11), the low and high biomass performance of the sensor would be compromised, due to the decreased overlap between the source and detector fibers.

The effects of varying the fiber diameter and numerical aperture are modeled in cases 2, 4-10, and 14-16 of Table 6. In general, use of smaller diameter or numerical aperture fiber decreases Y, but with attendant loss of light collection efficiency of the detection fiber. For devices employing a light source with small diameter and numerical aperture, such as many laser sources, the use of small diameter multi-mode or single mode fiber provides high light delivery efficiency, while allowing Y to be decreased. Therefore, in some embodiments of the present invention optimal performance is attained by the use of a laser source coupled to single mode optical fiber and one or more detectors coupled to multi-mode optical fibers.

TABLE 6

Source-Detector Overlap Calculations.

| | Inputs | | | | | | | Results | | |
|---|---|---|---|---|---|---|---|---|---|---|
| Configuration # | $D_1$ (mm) | $D_2$ (mm) | T (mm) | $NA_1$ | $NA_2$ | $n_g$ | $n_a$ | X (mm) | Y (mm) | Z (mm) |
| 1 | 0.2 | 0.2 | 0 | 0.22 | 0.22 | 1.5 | 1.33 | 0.715 | 0.040 | 0.04 |
| 2 | 0.1 | 0.1 | 2.1 | 0.22 | 0.22 | 1.5 | 1.33 | 0.715 | 0.763 | 0.14 |
| 3 | 0.2 | 0.2 | 2.1 | 0.22 | 0.22 | 1.5 | 1.33 | 0.715 | 0.663 | 0.04 |
| 4 | 0.4 | 0.4 | 2.1 | 0.22 | 0.22 | 1.5 | 1.33 | 0.715 | 0.463 | −0.16 |
| 5 | 0.6 | 0.6 | 2.1 | 0.22 | 0.22 | 1.5 | 1.33 | 0.715 | 0.263 | −0.36 |
| 6 | 0.1 | 0.2 | 2.1 | 0.22 | 0.22 | 1.5 | 1.33 | 0.715 | 0.713 | 0.09 |
| 7 | 0.1 | 0.2 | 2.1 | 0.22 | 0.39 | 1.5 | 1.33 | 0.715 | 1.066 | 0.19 |
| 8 | 0.1 | 0.2 | 2.1 | 0.22 | 0.48 | 1.5 | 1.33 | 0.715 | 1.268 | 0.25 |
| 9 | 0.1 | 0.2 | 2.1 | 0.39 | 0.39 | 1.5 | 1.33 | 0.715 | 1.420 | 0.29 |
| 10 | 0.1 | 0.2 | 2.1 | 0.48 | 0.48 | 1.5 | 1.33 | 0.715 | 1.822 | 0.40 |
| 11 | 0.2 | 0.2 | 1 | 0.22 | 0.22 | 1.5 | 1.33 | 0.715 | 0.337 | 0.04 |
| 12 | 0.2 | 0.2 | 6 | 0.22 | 0.22 | 1.5 | 1.33 | 0.715 | 1.819 | 0.04 |
| 13 | 0.2 | 0.2 | 12 | 0.22 | 0.22 | 1.5 | 1.33 | 0.715 | 3.598 | 0.04 |
| 14 | 0.1 | 0.2 | 1 | 0.22 | 0.39 | 1.5 | 1.33 | 0.715 | 0.607 | 0.19 |
| 15 | 0.1 | 0.2 | 1 | 0.39 | 0.39 | 1.5 | 1.33 | 0.715 | 0.827 | 0.29 |
| 16 | 0.1 | 0.2 | 1 | 0.48 | 0.48 | 1.5 | 1.33 | 0.715 | 1.079 | 0.40 |

X: Depth at which center cones of the source and detector fibers overlap within the medium.
Y: Edge-to-edge separation between the source and detector fiber cores.
Z: Closest point of intersection between the source and detector fiber cones within the container wall.

Example 7. Non-Invasive Fiber Optic Sensor for a Plastic Vessel

A fiber optic ferrule, as depicted in FIG. 14, was designed and constructed for making measurements through the bottom of a 1 mm thick clear plastic vessel. Vessels constructed from both Makrolon and Luran materials were tested. Source light was provided by a 1330 nm, 30 mW diode laser (Applied Optoelectronics, part number 01-05-1182 DFB-1330-BF-25-CW-SA-N182) with a songle mode fiber output that was split into 16 equal channels by a single mode fiber optic splitter (Neptec OS, Inc., part number SCSMDWCM). The light source penetration depth at this wavelength is limited to about 25 mm by water absorbance, allowing accurate reflectance measurements at low biomass even in shallow fluid depths. The sixteen fiber channels provide simultaneous light source excitation for up to sixteen fiber optic ferrules. The light source fibers (both in the splitter and in the ferrule) were single mode fibers (Corning Optical Fiber, part number SMF28e), while the detection fibers were 200 μm core multi-mode fibers (ThorLabs, part number FG200LC). The use of single mode optical fiber for source light conveyance has the benefit of lower cost for the fiber optic splitter compared to a multi-mode fiber splitter, as well as reducing the amount of specular reflectance from the vessel for a given source-detector separation and window thickness, compared to multi-mode fiber. The use of multi-mode optical fiber for detection allows capture of the diffusely reflected source light over a relatively large surface area, resulting in much higher collection efficiency compared to that provided by single mode fiber.

The detection fibers were individually detected, amplified, and multiplexed into a single analog-to-digital converter (ADC), as further described in Example 11. The multiplexing helps to reduce the overall system cost for monitoring multiple vessels simultaneously. The laser was modulated at approximately 781 Hz with a 75% duty cycle. The ADC output consisted of 16-bit integers streaming at a rate of 50 kHz. A Proportion-Integral-Derivative (PID) control loop was used to maintain the laser output power at the desired level by using the signal from a built-in laser monitoring diode as a feedback signal read by the microprocessor. Each laser modulation cycle consisted of 64 detector samples: 16 samples with the laser off followed by 48 samples with the laser on. Each measurement consisted of 2040 laser pulses (series lasting about 2.6 seconds). The first three points in the "laser off" and "laser on" periods were discarded and all remaining points were averaged and the resultant laser off signal was subtracted from the laser on signal to provide a demodulated reflectance signal. Table 7 summarizes the scheme for accomplishing this automatic sensitivity ranging, where the Analog-to-Digital Converter (ADC) count thresholds shown in the first column are user-controlled variables stored in instrument memory. If the ADC count is above a third threshold value, T3 (=40,000 in Table 7), the detector gain is decreased if it is not already at the minimum value. If the detector gain is already at the minimum value then the laser power is decreased by a factor, f. In this example f was selected to be 2. This process is repeated until the ADC counts fall below T3. On the other end of the scale, if the ADC counts are below a first threshold value, T1 (300 in Table 2), the laser power is increased if it is not already at a maximum allowed value. If the laser power is already at the maximum allowed value then the detector gain is increased. This process is repeated until the ADC counts are raised above T1. If the ADC counts fall between T1 and a second threshold, T2 (16,000 in Table 7), then the detector gain is maintained, but the laser power is increased by factors of f, until the ADC counts exceed T2. In this example, the sensitivity ranging was only activated when at least n sequential measurements indicated the need for adjustment, where n was set to 3. This helped prevent toggling of the sensitivity settings during noisy measurement periods. For optimal performance n could be decreased or increased depending on the amount of measurement noise. This scheme greatly increases the dynamic range of the instrument, as is necessary in many applications, such as biomass measurements ranging over many orders of magnitude of biomass. The median and median absolute deviation (MAD) of the demodulated reflectance signal were computed in two stages, as described in Example 5, above. The detector gain and laser power were automatically varied in order to keep the signals within a desired range of amplitudes. The median and MAD signals were normalized by the detector gain and laser power at which they were measured.

TABLE 7

Laser Power and Detector Gain Ranging Scheme

| ADC Counts | Laser Power | Detector Gain |
|---|---|---|
| 65536 | Decrease if detector gain is at minimum. | Decrease if not at minimum. |
|  | Decrease if detector gain is at minimum. | Decrease if not at minimum. |
| 40000 | Decrease if detector gain is at minimum. | Decrease if not at minimum. |
| 39999 | Maintain. | Maintain. |
|  | Maintain. | Maintain. |
| 16000 | Maintain. | Maintain. |
| 15999 | Increase if not at maximum. | Maintain. |
|  | Increase if not at maximum. | Maintain. |
| 300 | Increase if not at maximum. | Maintain. |
| 299 | Increase if not at maximum. | Increase if laser is at maximum. |
|  | Increase if not at maximum. | Increase if laser is at maximum. |
|  | Increase if not at maximum. | Increase of laser is at maximum. |

The "bubble calibration" shown in FIG. 15 was created by running 14 yeast concentrations under a variety of agitation and sparge conditions. A fixture was constructed to hold the fiber optic ferrule against the bottom of a 250 mL vessel. The vessel contained an agitator with two Rushton impellers, a sparge tube, and a pH probe. The yeast concentrations (shown in the legend of FIG. 15) ranged between 0.02 and 200 g/L dry cell weight; the agitation rate was varied between 1000 and 4500 rpm; and the room-air sparging ranged between 0 and 2 VVM (volume of gas per volume of medium per minute). The markers shown in FIG. 15 depict the measurements overlaid on which are linear fits.

This bubble calibration, consisting of the linear slopes, intercepts, and limits at each of the 14 yeast concentrations, was saved into instrument memory and then applied to subsequent measurements. The location of each new measurement, consisting of a median and MAD reflectance value, was determined on the bubble calibration map (FIG. 15), and the nearest 2 calibration lines were interpolated between to create a calibration line for the new measurement. The minimum reflectance of this interpolated calibration line was then reported as the "bubble-free" reflectance, $R_0$. FIG. 16 summarizes the testing results before (median reflectance) and after ($R_0$) bubble correction under a variety of yeast concentrations, and agitation and sparge conditions. As depicted in the top left graph of FIG. 16, within each of the 7 tested yeast concentrations, the agitation and sparge conditions were increased in 3 steps: (1) 1000 rpm, 0 VVM, (2) 2500 rpm, 1 VVM, and (3) 4000 rpm, 2 VVM. As can be seen by comparing the left and right sides of FIG. 16, the agitation and sparge rate caused significant increases in the measured median reflectance at all yeast concentrations, but after "bubble correction" these effects were largely removed.

Figure 17:
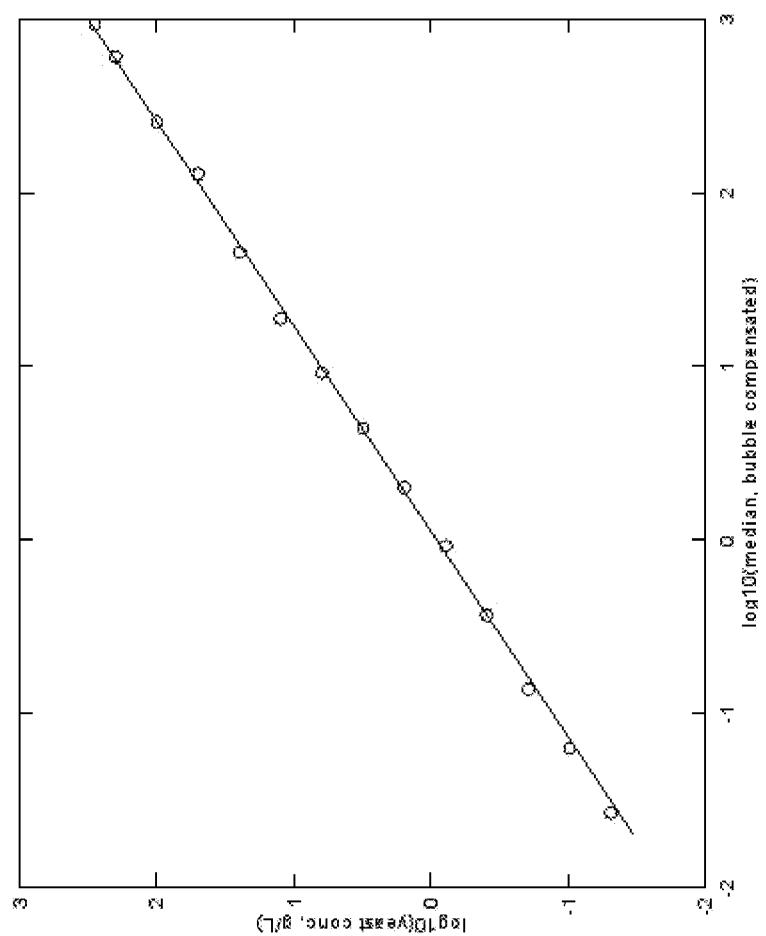
FIG. 17 provides an example of the linear relationship between biomass and bubble-compensated reflectance according to an embodiment of the present invention.

Bubble-compensation has the effect of improving the correlation between the bubble-compensated reflectance and biomass. In many cases this relationship can be accurately characterized by a linear fit in log-log space, such as shown in FIG. 17. These data were collected on a 15 mL Luran vessel filled with 12 mL of media. The linear relationship between biomass and bubble-compensated reflectance holds over more than 3 orders of magnitude of biomass concentration.

Example 8. Immersible Probe with Symmetrical Detectors

Another example of accurate biomass conversion in the presence of strong potential interference from bubbles was demonstrated using an immersible fiber optic probe. Three 200/220 µm core/cladding optical fibers were linearly close-packed, as depicted in FIG. 18. The center fiber was selected for the source, so that the two surrounding detection fibers were symmetrically positioned relative to the source. A 3 mW, 1310 nm diode laser (Xiamen Bely Communication Equip. Co., part number BLLD-RA-F3130B-1GR) was connected to the source fiber. The two detector fibers were connected to 1 mm diameter InGaAs detectors (Xiamen Bely Communication Equip. Co., part number BLPD-RA-1KAR-B). In some experiments, a bandpass interference filter centered near 1310 nm was added in front of the detector element, to discriminate against ambient light. Both the laser and detectors included fiber optic connectors, simplifying the coupling between the fibers and opto-electronic components. Except for the fiber optic apertures, the stainless steel exterior of the probe was coated with titanium nitride ("TiN"). This coating was found to reduce the adhesion of bubbles to the probe surface, as described in Example 12. The curvature of the sensor face (see "detail A" in FIG. 18) was also found to be effective at discouraging bubble adhesion. Comparison of the reflectance measured by the two symmetrically-placed detectors was found to be an effective method of eliminating measurements where interference was present. For example, by setting a threshold for agreement between the two detectors, measurements made during periods where one or more bubbles were present at the sensor tip could be easily rejected.

The response of the two detectors was normalized to each other using a quadratic polynomial correction in log-log space to the median reflectance measured by each detector over a wide range of biomass under conditions of no sparging and moderate agitation. This type of correction was also found to be effective at compensating for manufacturing differences between different sensors. Changes in optical coupling efficiency over time could be corrected with a linear correction based on measurements of a material having fixed reflectance properties.

Figure 19:
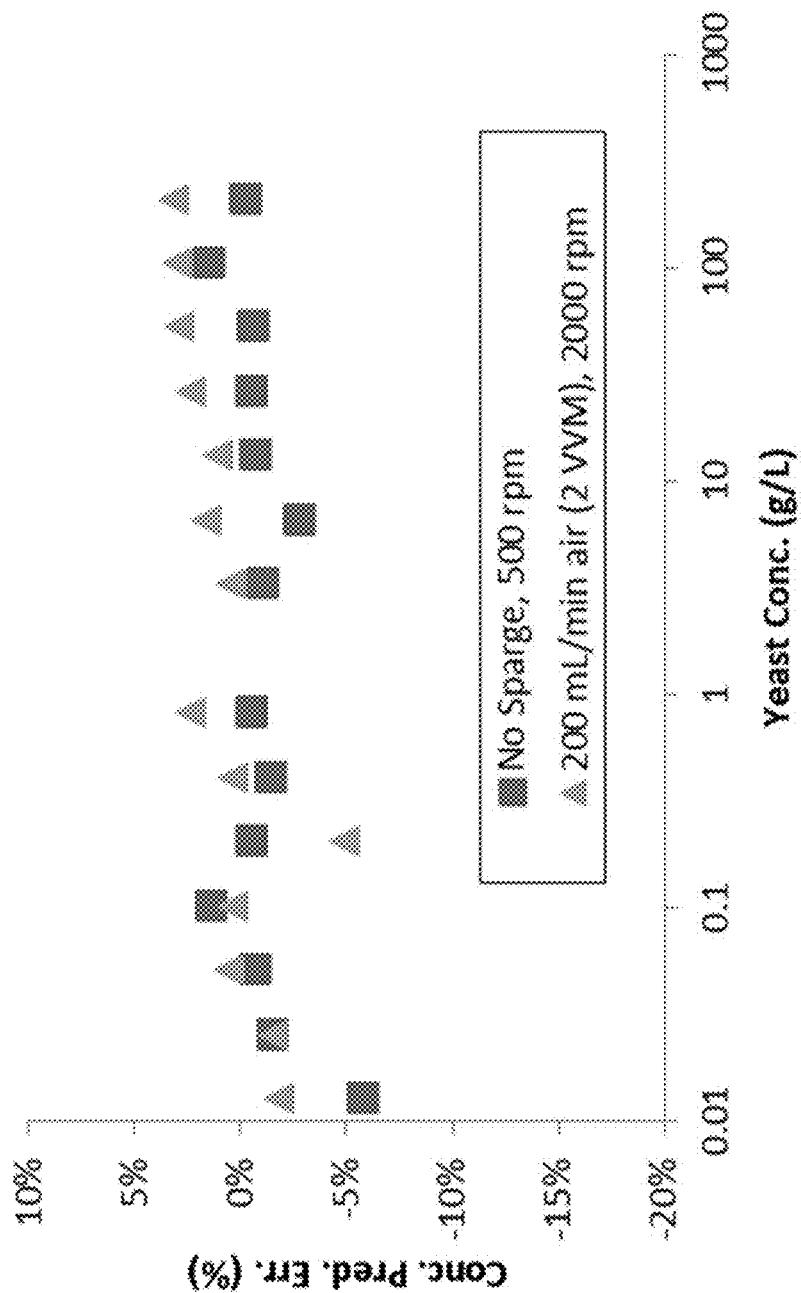
FIG. 19 provides an example of applying the bubble-correction methods of the present invention to provide accurate prediction of yeast concentration.

The probe was immersed in a 250 mL glass vessel containing 200 mL of media, dual Rushton impellers, a sparge tube, metal baffles, and several other probes (temperature, pH, dissolved oxygen). The tip of the probe was held at least 3 cm from the bottom of the vessel during all measurements. A bubble calibration was collected, following a similar process to that described in Example 7, except that additional measurements were collected at low biomass (to 0.001 g/L dry cell weight of yeast). The bubble calibration was tested under conditions of low and high bubbling, with the result shown in FIG. 19. Under both bubbling conditions, the concentration prediction error was less than 5% over more than 4 orders of magnitude of biomass (yeast dry cell weight 0.01-200 g/L).

Example 9. Applicability of Bubble Correction Across Different Organisms

The bubble calibration collected using yeast in Example 8 was applied without modification to subsequent measurements on a culture of *escherichia coli*. As can be seen in FIG. 20, the bubble-correction was effective over at least 4 orders of magnitude of biomass (*E. coli* dry cell weight), despite the large difference in the cell size and shape of the organism used to generate the bubble calibration (*saccharomyces cerevisiae*) and that used to test the bubble calibration (*e. coli*). This result demonstrates that the bubble correction method is not limited to the particular organism used to generate the bubble calibration.

Example 10. Effect of Dissolved Protein on Bubble Correction Mapping

Micro-organisms are frequently genetically engineered to express a particular protein of interest. In order to test the effect of protein expression on bubble calibration, Albumin (chicken egg white, Science Lab Supplies, part number C1210-30G) was added to yeast suspensions. Three yeast concentrations were tested: 0.2, 2, and 20 g/L dry cell weight. And at each yeast concentration, up to three levels of relative albumin concentration were tested: 1%, 5%, and 10%. The addition of albumin to the media resulted in greatly increased bubble retention under some conditions. As shown in FIG. 21, this increased bubble retention resulted in a non-linear shape to the MAD-Median mapping at the highest albumin concentrations. In order to compensate for bubbles in the presence of high protein concentrations a non-linear mapping may therefore be more effective than linear mapping. In some embodiments at least a $2^{nd}$ order polynomial fit is used for the bubble calibration, thereby extending the calibration to compensate for the types of extreme foaming that can be observed in the presence of high protein concentrations.

Example 11. Electrical Schematic for Single Sensor and Multiplexing Systems

Figure 22:
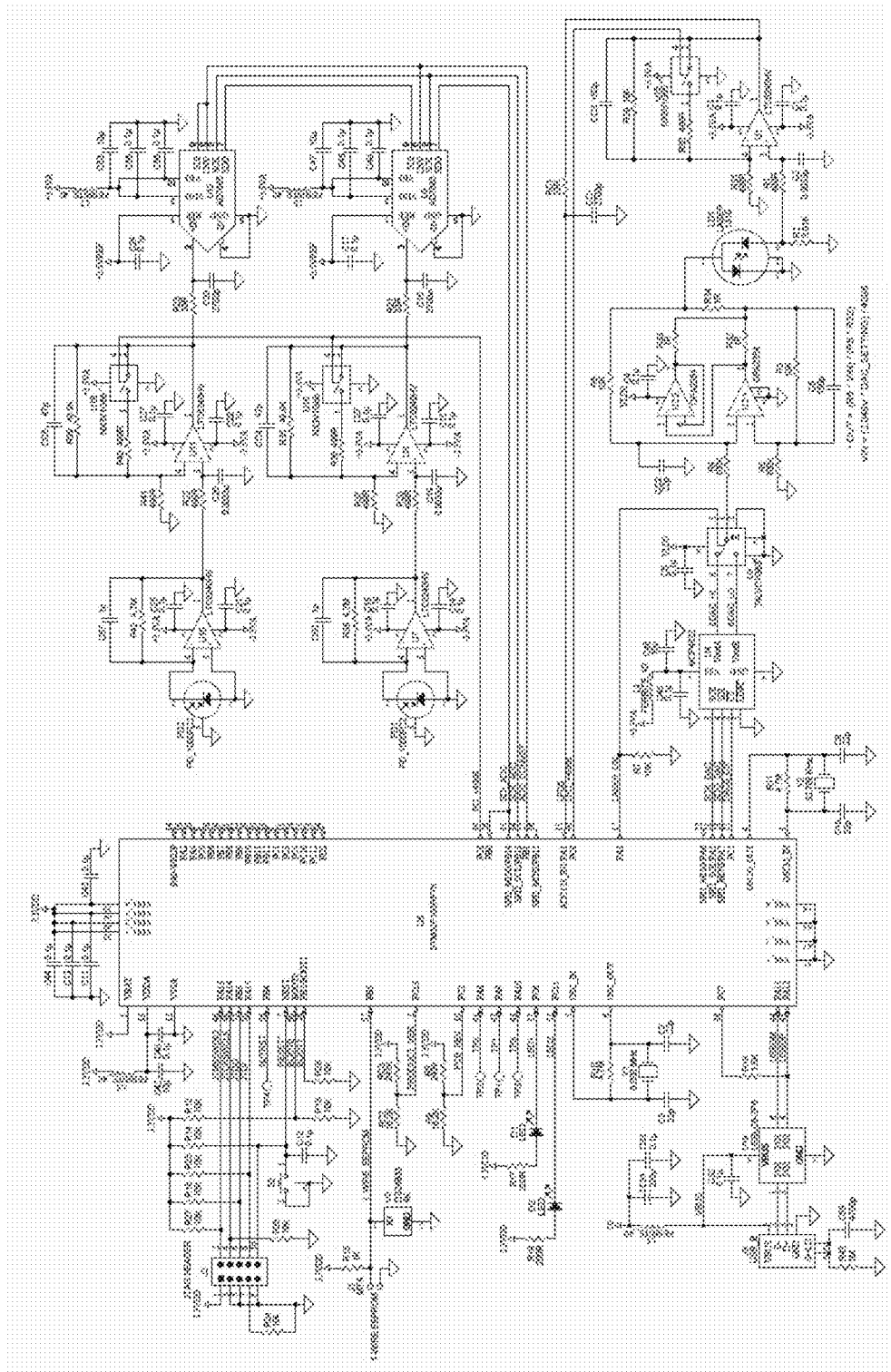
FIG. 22 provides an example embodiment of an electrical schematic of the present invention with one laser source and two detectors.

A schematic for an example embodiment of an electrical system of the present invention is shown in FIG. 22. A microprocessor U6 provides timing control of a laser LD1 and two detectors, PD1 and PD2. Digital laser control signals from the microprocessor are converted into an analog signal (voltage) by U4, switched between high and low states by U3, and converted to currents by U2:1 and U2:2 to power the laser. A laser monitoring diode is amplified by U1 and provided as a feedback to the microprocessor. The signals from the two detectors, PD1 and PD2, are first trans-impedance amplified by U7 and U10, and then further amplified with variable gain amplifiers U8 and U11. The gain level is controlled by digital communication between the microprocessor and gain switches U16 and U18. The amplified detector signals are digitized by analog-to-digital converters, U9 and U12. The microprocessor uses digital signals to compute median and MAD reflectance results, and applies corrections, normalizations, and calibrations, using stored coefficients. The coefficients that are most relevant to sensor performance are stored in a memory device within the sensor (J1, "1-wire EEPROM"). The microprocessor brings the measured reflectance signals into an optimal range by varying both the laser power and the detector gain. Communication between the microprocessor and other devices (e.g. a personal computer), is provided via a Universal Serial Bus (USB) interface within the microprocessor. Electrostatic discharge protection is provided by U19.

Figure 23:
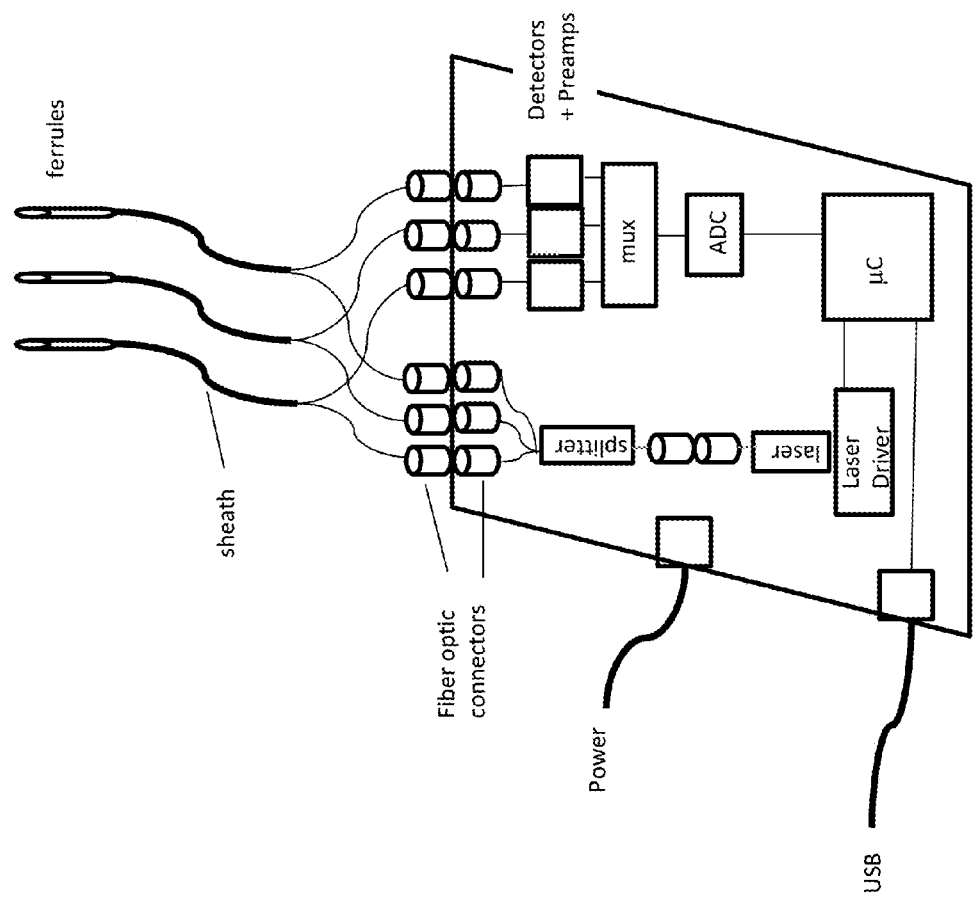
FIG. 23 provides an example embodiment of a schematic of the present invention providing the capability of monitoring the biomass in multiple vessels simultaneously.

A high-level schematic for a multiplexed embodiment of the present invention is depicted in FIG. 23. A single laser is split using a fiber optic splitter, providing light for multiple sensors simultaneously. The reflected source light captured by the detection fibers in the ferrules is individually detected and amplified, and then routed through a multiplexer before analog-to-digital (ADC) conversion. This arrangement provides a low-cost method for monitoring the biomass in multiple vessels simultaneously.

Example 12. Comparison of Uncoated and Coated Probes

Figure 24:
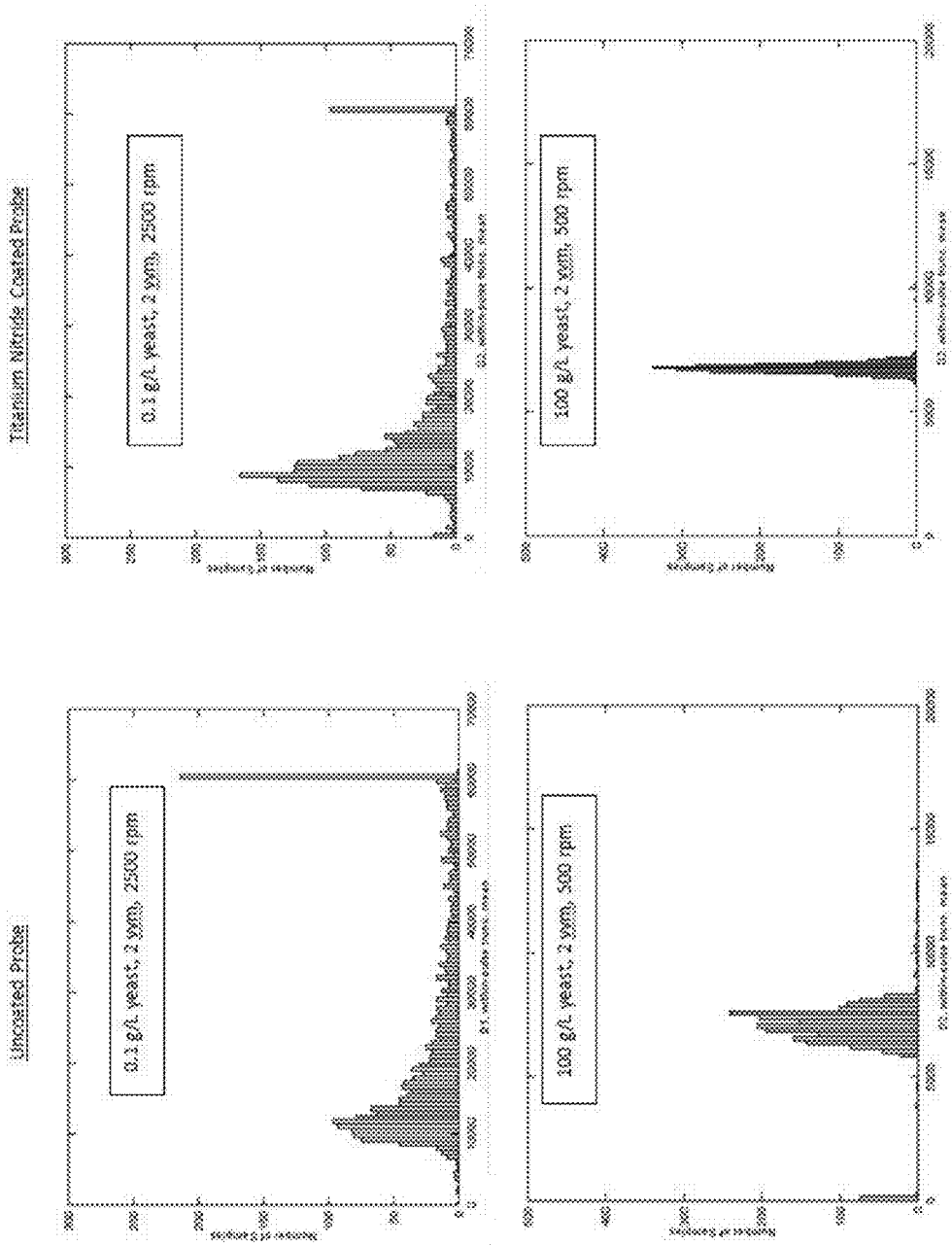
FIG. 24 shows reflectance signal histograms for uncoated and titanium nitride coated probes immersed in an aqueous medium containing yeast that is being stirred and sparged with room air.
Figure 25:
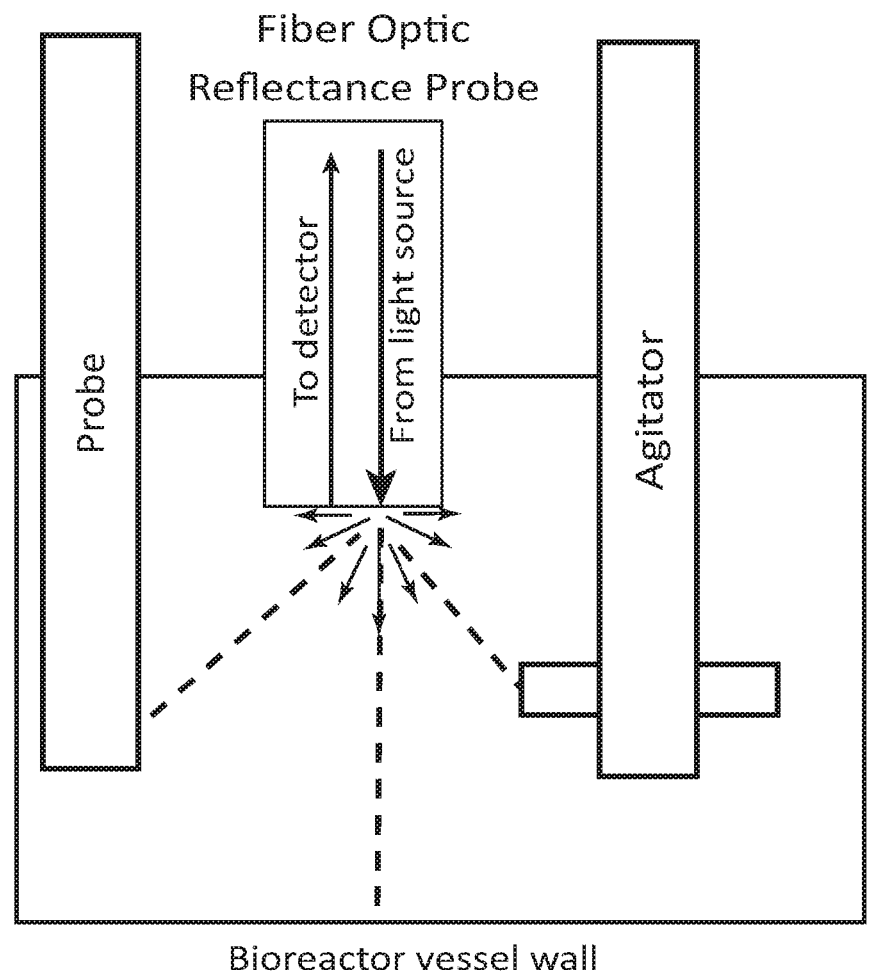
FIG. 25 depicts a fiber optic reflectance probe immersed in a medium contained in a bioreactor. Also immersed in the medium are an agitator and a second generic probe. The distance from the optical interface of the probe with the medium to other stationary objects in the medium is depicted by dashed lines.

Several probes were constructed of identical design to that described in Example 8, except that the titanium nitride coating was omitted, so that the outer surface of the probe tip surrounding the optical fibers was bare polished stainless steel instead of titanium nitride coated stainless steel. Testing was performed by immersing both uncoated and coated probes in the same plastic 250 mL bioreactor vessel filled with medium. Five yeast concentrations (0, 0.1, 1, 10, and 100 g/L) were tested under conditions of fixed 2 vvm room air sparging and variable agitation (500, 1500, and 2500 rpm) using a Rushton type impeller. Laser driving and data acquisition were as described in Example 8. Within each laser pulse a 25% truncated mean was computed from the data points collected during the period that the laser was on. The resulting measurements were sorted into histograms as shown in FIG. 24. Differences between the uncoated and coated probes were particularly evident under conditions of high biomass and sparging but relatively low agitation rates, such as shown in the bottom two graphs in FIG. 24. Under these conditions the signal distribution was substantially more narrow for the coated probe relative to the uncoated probe. These results demonstrate reduced susceptibility of the titanium nitride coated probe to bubble adhesion, under certain conditions. A more narrow signal distribution implies that the median value can be estimated with higher accuracy, leading to more accurate prediction of biomass.

Example 13. Envisioned Combinations of Device Elements

The typical device for measuring the concentration of particles in a media includes, e.g., one or more light sources to interrogate the media, one or more light detectors, a container holding media with one or more particle types. The light sources can emit light at one frequency, or in a range of frequencies, in a direction characterized by the optical axis (e.g., center of an illumination cone). The detectors can detect along an optical axis along which light is received into the detector.

Functional combinations of particle concentration assay devices can include several combinations of elements. For example, e.g., devices can include one light source and one detector; one light source and two detectors, two light sources and one detector, one light source and three detectors, one light source and four detectors, two light sources (having different emission wavelengths) and two detectors. Any of the above combinations can be used to analyze a media in a container (through a wall transparent to the light source wavelength(s)) or the detector and/or light source can be immersed in the media for interrogation and detection. Any of the above combinations can be used in combination with media containing one type of particle (e.g., a biologic cell) or two or more types of particles (e.g., gas bubbles, macromolecule aggregates, and/or relatively large inorganic particles). Any of the above combinations can be used in combination with alternate alignments of detector and/or light source central optical axes, such as parallel light/detector axes, converging light/detector axes, normal incident optical axis at the optical interface with media, and/or tilted orientation of light axis and/or detector axis at the media optical interface.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations and permutations, all of which cannot reasonably be recited individually in this document, but can be understood by one of skill in the art on review of this specification.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of using optical scattering to determine the concentration of particles, which method comprises:
    irradiating a medium with a first source of light comprising a first central optical axis, wherein the light absorption is characterized by an average absorption path length in the medium;
    selecting the wavelength of the light so that a distance between the optical interface with the medium and a stationary optically reflective object in the medium falling within an emission cone of the light source is greater than the average absorption path length of the light;
    detecting light scattered by the particles in the medium using a first detector comprising a second central optical axis;
    positioning the first central optical axis and second central optical axis so that a distance between the first and second optical axes at the optical interface with the medium is at least 2-fold less than the average absorption path length for the selected wavelength; and,
    correlating the detected light to the concentration of the particles;
    wherein the distance between the first central optical axis and the second central optical axis is further selected to minimize sensitivity to specular reflections from a window between the sensor and medium, while also maximizing the range of sensitivity to changes in the concentration of the particles.

2. The method of claim 1, wherein the medium is an aqueous medium.

3. The method of claim 1, wherein a container used for containing the medium is other than a cuvette or flow cell.

4. The method of claim 1, wherein a container used for containing the medium is selected from the group consisting of: a shaker flask, a T-flask, a centrifuge tube, a test tube, a roller bottle, a fermentor, a bioreactor, a stir flask, a carboy, a bag, a media bottle, a multiwell plate, a petri dish, a syringe and a pipette.

5. The method of claim 1, wherein the wavelength of light is an infrared (IR) wavelength.

6. The method of claim 1, wherein the wavelength of light ranges from about 700 nm to about 2000 nm.

7. The method of claim 6, wherein the wavelength is about 1310 nm.

8. The method of claim 6, wherein the wavelength is about 1330 nm.

9. The method of claim 6, wherein the wavelength is about 1550 nm.

10. The method of claim 1, wherein the optical interface of the first central optical axis with the medium is on the same side of the medium as the optical interface of the second central optical axis.

11. The method of claim 1, wherein detected light is scattered at an angle ranging from −45 degrees to +45 degrees from the light source to the particle to the detector.

12. The method of claim 1, wherein the light source central optical axis and detector central optical axis are aligned parallel to each other.

13. The method of claim 1, wherein the particles are selected from the group consisting of: bacteria, animal cells, plant cells, polymer particles, proteins, nanoparticles, a sol gel, and a virus.

14. The method of claim 1, further comprising providing a second detector positioned symmetric to the first detector with respect to the light source.

15. The method of claim 14, further comprising receiving signals from the two symmetrically positioned detectors and determining whether an interfering object is present in the vicinity of the sensor, which object interferes with accurate measurement of particle concentration.

16. The method of claim 1, further comprising reporting the particle concentration in units that are selectable by the user.

17. The method of claim 1, further comprising using at least one optical fiber to transmit the light from the light source towards the medium and/or to transmit the light scattered from the medium to the detector.

18. The method of claim 1, further comprising:
converting a signal from the detector into data;
computing a statistical measure of a central value and a distribution of the data; and,
determining the concentration of a first particle type substantially independent of a second particle type that is also present in the medium;
wherein the first particle type is biological and the second particle type is gas bubbles.

19. A device for determining the concentration of particles in a vessel, which device comprises:
a housing;
a sensor in the housing and comprising a first light source, wherein a wavelength emitted by the light source is absorbed by a medium of interest, which absorption is characterized by an average absorption path length;
the sensor further comprising a first detector positioned to detect a signal of the first light source wavelengths scattered by particles within the medium; and,
a processor configured to correlate the detected signal to the concentration of particles;
wherein a distance between a central optical axis of the first light source and a central optical axis of the first detector at an optical interface with the medium is at least 2-fold less than the average absorption path length; and,
wherein a distance between the optical interface with the medium and a non-biological optically reflective stationary object in the medium falling within the emission cone of the light source, is greater than the average absorption path length; and
wherein the distance between the central optical axis of the first light source and the central optical axis of the first detector is selected to minimize sensitivity to specular reflections from a window between the sensor and medium, while also maximizing the range of sensitivity to changes in the concentration of the particles.

20. The device of claim 19, further comprising a controller configured to control the light source, and to measure the detected signal.

21. The device of claim 20, further comprising a multiplexer that selects the detector channel to be routed into an analog-to-digital converter, thereby accommodating measurements in multiple vessels.

22. The device of claim 19, further comprising a fiber optic splitter or switcher, thereby accommodating measurements in multiple vessels.

23. The device of claim 19, wherein the light source or detector comprise fiber optical components which are optically linked to electro-optical components that are physically separated from the housing.

24. The device of claim 23, wherein a single mode optical fiber is used to convey the light from the light source and a multi-mode optical fiber is used to convey light to the detector.

25. The device of claim 19, wherein a portion of the housing that optically interfaces with the medium is coated with a material that discourages adherence of some types of particles.

26. The device of claim 25, wherein the coating is titanium or zirconium nitride.

27. The device of claim 19, further comprising a hybrid electro-optical connector on the sensor.

28. The device of claim 19, further comprising a collar for the sensor that helps determine the position of the sensor when inserted into the vessel containing the medium.

29. A method of using optical scattering to determine the concentration of particles, which method comprises:
irradiating a medium with a first source of light comprising a first central optical axis, wherein the light absorption is characterized by an average absorption path length in the medium;
selecting the wavelength of the light so that a distance between an optical interface of the light source with the medium and a stationary optically reflective object in the medium falling within an emission cone of the light source is greater than the average absorption path length of the light;
detecting light scattered by the particles in the medium using a first detector comprising a second central optical axis;
positioning the first central optical axis and second central optical axis so that a distance between the first and second optical axes at the optical interface with the medium is at least 2-fold less than the average absorption path length for the selected wavelength;
correlating the detected light to the concentration of the particles;
determining with a processor the concentration in the medium of a first particle type in the presence of a second particle type different from the first particle type;
wherein a detection bandwidth and measurement volume used in the method allow signal fluctuations due to the second particle type to be resolved, whereas the signal due to the first particle type is substantially constant at a given concentration;
and the method comprises a step of separating the signal fluctuations from the constant signal to determine the concentration of the first particle type;
whereby the concentration of the first particle type is determined with reduced error due to background reflectance signals from the second particle type in the medium.

30. The method of claim 29, wherein the number of particles within the measurement volume is at least 100-fold greater for the first particle type than for the second particle type.

* * * * *